(12) United States Patent
Perumal et al.

(10) Patent No.: US 9,233,110 B2
(45) Date of Patent: *Jan. 12, 2016

(54) PROTEIN NANOCARRIERS FOR TOPICAL DELIVERY

(76) Inventors: Omathanu P. Perumal, Brookings, SD (US); Ranjith Kumar Averineni, Brookings, SD (US); Satheesh K. Podaralla, Santa Clara, CA (US); Mohammed Alqahtani, Brookings, SD (US)

(*) Notice: Subject to any disclaimer, the term of this patent is extended or adjusted under 35 U.S.C. 154(b) by 947 days.

This patent is subject to a terminal disclaimer.

(21) Appl. No.: 13/404,536

(22) Filed: Feb. 24, 2012

(65) Prior Publication Data

US 2012/0195947 A1   Aug. 2, 2012

Related U.S. Application Data

(63) Continuation-in-part of application No. 12/991,872, filed as application No. PCT/US2009/002935 on May 11, 2009, now Pat. No. 8,669,225.

(60) Provisional application No. 61/127,134, filed on May 9, 2008, provisional application No. 61/446,934, filed on Feb. 25, 2011.

(51) Int. Cl.
| | |
|---|---|
| *A61K 31/505* | (2006.01) |
| *A61K 31/07* | (2006.01) |
| *A61K 35/12* | (2015.01) |
| *A61K 35/16* | (2015.01) |
| *C12N 15/87* | (2006.01) |
| *A61K 8/49* | (2006.01) |
| *A61K 8/64* | (2006.01) |
| *A61Q 7/00* | (2006.01) |
| *A61K 8/67* | (2006.01) |
| *A61Q 19/00* | (2006.01) |
| *A61K 8/98* | (2006.01) |
| *A61K 8/02* | (2006.01) |
| *A61K 9/00* | (2006.01) |
| *A61K 9/51* | (2006.01) |

(52) U.S. Cl.
CPC .............. *A61K 31/505* (2013.01); *A61K 8/0241* (2013.01); *A61K 8/4953* (2013.01); *A61K 8/64* (2013.01); *A61K 8/671* (2013.01); *A61K 8/983* (2013.01); *A61K 9/0014* (2013.01); *A61K 9/5169* (2013.01); *A61K 31/07* (2013.01); *A61K 35/12* (2013.01); *A61K 35/16* (2013.01); *A61Q 7/00* (2013.01); *A61Q 19/00* (2013.01); *C12N 15/87* (2013.01); *A61K 2800/412* (2013.01); *Y10T 428/13* (2015.01)

(58) Field of Classification Search
None
See application file for complete search history.

(56) References Cited

U.S. PATENT DOCUMENTS

| | | | |
|---|---|---|---|
| 5,254,673 A | 10/1993 | Cook et al. | |
| 5,271,961 A | 12/1993 | Mathiowitz et al. | |
| 5,330,778 A | 7/1994 | Stark et al. | |
| 5,356,467 A | 10/1994 | Oshlack et al. | |
| 5,679,377 A | 10/1997 | Bernstein et al. | |
| 8,669,225 B2 * | 3/2014 | Perumal et al. | 530/300 |
| 8,697,098 B2 * | 4/2014 | Perumal et al. | 424/400 |
| 2003/0232091 A1 | 12/2003 | Shefer et al. | |
| 2004/0241207 A1 | 12/2004 | Chauhan et al. | |
| 2006/0002852 A1 | 1/2006 | Saltzman et al. | |
| 2006/0260777 A1 | 11/2006 | Rashba-Step et al. | |
| 2007/0087061 A1 | 4/2007 | Drake et al. | |
| 2007/0178165 A1 | 8/2007 | Altreuter et al. | |
| 2008/0187595 A1 | 8/2008 | Jordan et al. | |
| 2008/0248122 A1 | 10/2008 | Rashba-Step et al. | |
| 2008/0268061 A1 | 10/2008 | Jordan et al. | |
| 2009/0074859 A1 | 3/2009 | Patel | |
| 2009/0239789 A1 | 9/2009 | Saltzman et al. | |
| 2009/0311407 A1 | 12/2009 | Lucey et al. | |
| 2010/0009007 A1 | 1/2010 | Darvari et al. | |
| 2011/0052682 A1 | 3/2011 | Fatmi et al. | |

FOREIGN PATENT DOCUMENTS

| | | |
|---|---|---|
| DE | 102005016873 | 10/2006 |
| WO | 2007018943 | 2/2007 |
| WO | WO 2009/137112 A1 | 11/2009 |

OTHER PUBLICATIONS

Lai et al., "Preparation of new 5-fluorouracil-loaded zein nanoparticles for liver targeting," Int. J. Pharm. (2011) 404: 317-23. Abstract.

Podaralla et al., "Preparation of zein nanoparticles by pH controlled nanoprecipitation," J. Biomed. Nanotechnol. (2010) 6 (4): 312-7.

Zhong et al., "Zein nanoparticles produced by liquid-liquid dispersion," Food Hydrovolloids (2009) 23 (8): 2380-2387. Abstract.

(Continued)

*Primary Examiner* — Anand Desai

(57) ABSTRACT

The invention encompasses nanoparticle assemblies and methods for preparing nanoparticle and compositions comprising such nanoparticles for use in topical or skin applications. The invention further encompasses methods of complexing various molecular and cellular entities to the nanoparticles using the resulting nanoparticles of the invention as delivery devices. The nanoparticles can be used for a variety of applications, such as treating cancer, targeting tumors, reducing the toxicity of a drug in vivo, increasing the efficacy of a complexed agent in vivo, protecting a complexed agent against degradation, increasing skin penetration and retention of drugs, and enhancing the water solubility/dispersibility of a drug or other agent.

20 Claims, 36 Drawing Sheets

(56) References Cited

OTHER PUBLICATIONS

International Search Report (Form PCT/ISA/210) for corresponding International Application No. PCT/US2012/026520 mailed Jun. 8, 2012.
Written Opinion (Form PCT/ISA/237) for corresponding International Application No. PCT/US2012/026520 mailed Jun. 8, 2012.
Patel, A., et al., Synthesis and characterization of zein-curcumin collodial particles. Soft Matter 2010, 6, 6192-6199.
Patel, A., et al., Sodium Caseinate Stabilized Zein Collodial Particles. J. Agric. Food Chem. 2010, 58(23), pp. 12497-12503.
Liu et al. Microspheres of corn protein. zein, for an invermectin drug delivery system. Biomaterials 26 (2005) 109-115.
Lopez et al. Zein microspheres as drug/antigen carriers: A study of their degradation and erosion, in the presence and absence of enzymes. J. Microencapsulation 23 (2006) 303-314.
Parris et al. Encapsulation of Essential Oils in Zein Nanospherical Particles. J. Agric. Food. Chemistry 53 (2005) 4788-4792.
Veronese et al. 'PEGylation, successful approach to drug delivery', Drug Discovery Today, vol. 10, No. 21. Nov. 2005. 1451-1458.
Cevc, Gregor. 'Lipid vesicles and other colloids as drug carriers in the skin', Advanced Drug Delivery Reviews, Mar. 2004, vol. 56 No. 5, pp. 675-711.
Cui F. et al. 'Biodegradable nanoparticles loaded with insulin?phospholipid complex for oral delivery: Preparation, in vitro characterization and in vivo evolution', Journal of Controlled Release, Aug. 2006, vol. 114, No. 2, pp. 242-250.
Leach WT. et al. 'Encapsulation of protein nanoparticles into uniform-sized microspheres formed in a Spinning Oil Film', AAPS PharmSciTech. 2005, vol. 6, No. 4, Article 75, pp. E605-E617.
Li S. et al. 'Pharmacokinetic characteristics and anticancer effects of 5-Fluorouracil loaded nanoparticles', BMC Cancer, Apr. 14, 2008, vol. 8, No. 103, pp. 1-9.(doi: 10.1186/1471-2407-8-103.).
Mason et al. 'Preparation of White Zein From Yellow Corn', Journal of Biological Chemistry.

* cited by examiner

PROTEIN NANOCARRIERS FOR TOPICAL DELIVERY

CROSS REFERENCE TO RELATED APPLICATION

This application is a continuation-in-part of U.S. application Ser. No. 12/991,872, filed Dec. 13, 2010, which is a national phase entry of PCT/US2009/002935, filed May 11, 2009, which claims the benefit of U.S. Provisional Application No. 61/127,134, filed May 9, 2008; this application also claims benefit of U.S. Provisional Application No. 61/446,934, filed Feb. 25, 2011. The disclosures of each of these applications are incorporated by reference herein in their entireties.

FIELD OF THE INVENTION

The present invention relates generally to drug delivery technologies, and more specifically to a nanoparticle drug delivery system, including methods for preparing such a system using a hydrophobic water insoluble protein, which nanoparticles may include prolamine to generate a topical drug delivery system.

BACKGROUND INFORMATION

Zein, a plant protein that can be isolated from corn or maize, belongs to a family of prolamines that are composed of high amounts of non-polar amino acids, such as proline, glutamine and asparagine. Zein is odorless, non-toxic, biodegradable and water-insoluble, and is therefore an attractive component for many applications.

Zein has been investigated or used as a polymer in the pharmaceutical, medical, food, cosmetic, adhesive and packaging industries. In the food and pharmaceutical industries, zein has been used, for example, to film-coat materials and to form particulate systems such as microparticles or nanoparticles (U.S. Pat. No. 5,679,377 (Bernstein et al.), herein incorporated by reference in its entirety; Liu et al., Biomaterials 26 (2005) 109-115; Lopez and Murdan, J Microencapsulation 23 (2006) 303-314; Zhong et al., Food Biophysics 3 (2008) 186-190; Parris et al., J Agric Food Chemistry 53 (2005) 4788-4792).

Various methods of forming zein particles have been proposed. For example, U.S. Pat. No. 5,330,778 (Stark; herein incorporated by reference in its entirety) describes a method for preparing microparticles using zein using pH alteration to form the zein microparticles. The method, however, produces zein particles with larger micron sizes and with a wide particle size distribution, which has significant drawbacks, for example, for in vivo use. A biomaterial used for human or animal applications needs to be safe and non-immunogenic. In general, upon in vivo administration (e.g., introduction into the body) of particles, phagocytic cells in the blood and tissues, which are responsible for immunological recognition and removal of foreign particles, can initiate an immune response depending on the physicochemical characteristics of the particles. The uptake by phagocytic cells is dependent upon both particle size and surface hydrophobicity of the foreign particle. Particles greater than about 500 nm in diameter are highly prone to phagocytosis. Additionally, particles with a hydrophobic surface are easily recognized by the phagocytic cells. For example, Lopez and Murdan reported that zein microspheres having a diameter of 1.36±0.036 µm are immunogenic and, consequently, are not suitable as a drug, vaccine or other therapeutic carrier (Lopez and Murdan, J Pharm Pharmacol 58 (2006) 769-774)

Accordingly, new methods are needed for preparing zein particles to render the particles useful for therapeutic and cosmetic applications. Also needed are new therapeutic carriers for the delivery of important therapeutic and cosmetic agents in a safe and effective manner, so as to overcome challenges associated with skin penetration, retention, stability, skin irritation, and follicular targeting.

SUMMARY OF THE INVENTION

Applicants have developed new prolamine based nanoparticulate topical formulations of retinol and related compounds. Nanoparticles have been developed using prolamine proteins such as zein, a protein derived hydrophobic plant protein. Because zein has similar characteristics to skin keratin, it is used as a model protein to test the skin irritation of excipients used in topical formulations (zein test). Due to its similarity to skin keratin, zein nanocarriers are excellent delivery vehicles for hydrophobic and hydrophilic compounds, for example, via application to the skin.

Accordingly, the invention provides a nanoparticle comprising a prolamine protein and a therapeutic or cosmetic agent, wherein the nanoparticle is biodegradable, biocompatible, and non-immunogenic, the therapeutic or cosmetic agent is a retinoid or an ester thereof, and the diameter of the nanoparticle is less than about 400 nm. The prolamine protein can be zein, gliadin, hordein, kafirin, or a combination thereof. In one embodiment, the prolamine protein is white zein. In some embodiments, the nanoparticles can encapsulate hydrophilic or hydrophobic compounds. In other embodiments, the nanoparticles may encapsulate retinoids.

The retinoid can be, for example, retinol, 13-trans-retinoic acid (tretinoin), 13-cis-retinoic acid (isotretinoin), 9-cis-retinoic acid (alitretinoin), retinaldehyde, etretnate, acitretin, α-carotene, β-carotene, γ-carotene, β-cryptozanthin, lutein, zeaxanthin, or a combination thereof. For example, the retinoid can include retinol esterified with a $(C_2\text{-}C_{22})$carboxylic acid or fatty acid, such as retinyl acetate or retinyl palmitate. The retinoid can also be retinoic acid esterified with a straight chain or branched $(C_1\text{-}C_{22})$alcohol.

The retinoid in the nanoparticle can be about 0.01 wt. % to about 0.3 wt. % of the prolamine of the nanoparticle. The diameter of the nanoparticle can be about 75 nm to about 300 nm, about 100 nm to about 280 nm, or about 180 nm to about 220 nm.

The surface of the nanoparticle can be crosslinked, and/or the prolamine protein of the nanoparticle can be PEGylated. The PEGylation can include PEGylating with PEG having a molecular weight of about 3 kDa to about 220 kDa, or about 4 kDa to about 20 kDa.

In embodiments, the nanoparticle may be complexed to other polymers, including, but not limited to, dextran, β-casein, and gum *Arabica*.

The nanoparticle can encapsulate or adsorb on its surface one or more additional active agents, a diagnostic agent, an imaging agent, or a combination thereof. The active agent can be an antioxidant, an anti-inflammatory agent, an anticancer drug, or a free-radical scavenger.

A surfactant to phospholipid ratio used when preparing the nanoparticles can significantly influence stabilization of the prolamine nanoparticles and prevent aggregation. Moreover, phospholipids and PLURONICS can also act as penetration enhancers to increase the skin penetration of prolamine nanoparticles. Additionally, the concentration of BHT or other antioxidant used when preparing the nanoparticles can significantly influence the stabilization of nanoparticles, and the BHT or other antioxidant can be located within the nanoparticles and/or on the nanoparticle surface.

The invention also provides a composition that includes a plurality of nanoparticles as described herein wherein the composition is in the form of a dry free flowing, colorless or white, non-hygroscopic powder. The invention further provides a pharmaceutical or cosmetic composition comprising a plurality of nanoparticles as described herein and a pharmaceutically or cosmetically acceptable diluent, excipient, or carrier. The pharmaceutical or cosmetic composition can be, for example, in the form of a dispersion, an aerosol formulation, a gel, an ointment, a cream, a lotion, or a shampoo. In some embodiments, the pharmaceutical or cosmetic composition cab be in the form of a water removable formulation.

The polydispersity index of the nanoparticles can be about 0.2 to about 0.5. The nanoparticles can enhance the stability of the encapsulated retinoid or other encapsulated agents.

The composition can effect greater skin penetration and retention by the retinoid when in contact with mammalian skin, compared to administration of the retinoid to mammalian skin in the absence of the nanoparticles. The formulation of nanoparticles can be less irritating to human skin than the same amount of the retinoid administered to human skin in a non-nanoparticle formulation.

The invention also provides a method of administering a therapeutic agent to a subject that includes administering to a subject suffering from a skin disease or skin condition a pharmaceutically or cosmetically effective amount of a nanoparticle composition described herein, thereby treating the disease or condition. Diseases or conditions that can be treated with the compositions described herein include acne, psoriasis, keratinization disorders, skin discoloration, and cutaneous malignancies (skin cancer and melanoma). The nanoparticle compositions can also be used to promote wound healing, and to reduce the appearance of wrinkles, cellulite, and/or the effects of photoaging. The composition can provide a prolonged release of the retinoid, for examples, over the course of a day or several days (e.g., one week).

In one embodiment, the invention provides a method to enhance the chemical stability of a retinoid comprising encapsulating the retinoid in a nanoparticle as described herein, thereby enhancing the chemical stability of the retinoid.

In another embodiment, the invention provides a method of increasing the shelf-life of a retinoid comprising formulating the retinoid in a nanoparticle as described herein.

In another embodiment, the invention provides a method to enhance the water solubility of a retinoid comprising encapsulating the retinoid in a nanoparticle as described herein, thereby enhancing the water dispersibility of the retinoid.

In another embodiment, the invention provides a method to enhance the water dispersibility of a retinoid comprising encapsulating the retinoid in a nanoparticle as described herein, thereby enhancing the water dispersibility of the retinoid.

In another embodiment, the invention provides a method to provide sustained release of a retinoid from a composition that includes encapsulating a retinoid in a nanoparticle as described herein and contacting mammalian skin with the encapsulated compound, wherein the retinoid is released from the nanoparticle over a period of about 1 hour to about 14 days.

In another embodiment, the invention provides a method to administer a retinoid to a subject in need thereof or a sample in a non-immunogenic and biocompatible formulation comprising contacting the subject or the sample with a nanoparticle as described herein or a composition as described herein, thereby providing the non-immunogenic and biocompatible formulation to the subject or the sample.

In another embodiment, the invention provides a method to increase the skin penetration of a retinoid comprising encapsulating the retinoid in a nanoparticle as described herein and contacting mammalian skin with a composition comprising the nanoparticle, thereby increasing the skin penetration of the retinoid compared to the skin penetration of the retinoid in the absence of the nanoparticle.

In another embodiment, the invention provides a method to enhanced accumulation of drug comprising encapsulated in a nanoparticle as described herein, for example, tumors of the skin, and administering to a subject in need thereof a plurality of the nanoparticles, wherein the encapsulated drug accumulates at the tumor to a greater degree than a drug that is administered to a subject in the absence of the nanoparticles, wherein the tumor is a skin cancer tumor and the administration is topical. In one embodiment, a therapeutic agent (e.g., cell, antibody, hormone, protein, peptide, growth factor, nucleic acid, and the like) may be adsorbed, complexed or conjugated to the surface of the nanoparticle.

In another embodiment, the invention provides a method to reduced drug accumulation in non-tumor bearing tissues in a mammal comprising encapsulating a drug in a nanoparticle as described herein, and administering to a subject that has a skin cancer tumor a plurality of the nanoparticles, wherein the administration is topical and the encapsulated therapeutic agent accumulates in non-tumor bearing tissues to a lesser degree than a therapeutic agent that is administered to a subject in the absence of the nanoparticles.

In another embodiment, the invention provides a method to increase the therapeutic or cosmetic efficacy of a therapeutic agent (e.g., retinoid) comprising administering a plurality of nanoparticles as described herein to a subject, wherein the efficacy of the therapeutic agent is increased compared to administration of the therapeutic agent in the absence of the nanoparticles.

In another embodiment, the invention provides a method to reduce the toxicity of a therapeutic agent comprising administering a plurality of nanoparticles as described herein to a subject, wherein the toxicity of the therapeutic agent is reduced compared to the toxicity of the therapeutic agent administered in the absence of the nanoparticles.

In yet another embodiment, the invention provides a method to reduce the skin irritation rating of a topically applied retinoid comprising administering a plurality of nanoparticles as described herein to a subject, wherein the skin irritation rating of the retinoid is reduced compared to administration of the retinoid in the absence of the nanoparticles.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 5(a) is a scanning electron microphotograph of blank zein nanoparticles. The particles are shown to be spherical and with a smooth surface. (Scale represents 1 mm=1.76 μm).

FIG. 5(b) is a transmission electron microphotograph of blank zein nanoparticles. (Scale represents 1 mm=8.038 nm).

FIG. 5(c) is a scanning electron microphotograph of coumarin loaded zein nanoparticles. (Scale represents 1 mm=0.87 μm).

FIG. 5(d) is a transmission electron microphotograph of 6,7-hydroxy coumarin-loaded zein nanoparticles. (Scale represents 1 mm=8.04 nm).

In FIGS. 19, 23-26, and 42, BHT refers to butylated hydroxyltoluene (2,6-di-tert-butyl-4-methylphenol).

FIG. 23 illustrates the solid state stability of retinol loaded nanoparticles when stored under ambient light. Free retinol and retinol nanoparticles were kept in clear glass vials and were exposed to room light for one week. The retinol remaining at different time points was measured by UV-visible spectrophotometry at 320 nm (mean±SD; n=3). The nanoparticles were prepared using the method as described in FIG. 19.

FIG. 24 illustrates the solid state stability of retinol loaded nanoparticles when stored in the absence of light. Free retinol and retinol nanoparticles were kept in a clear glass vials and stored in a dark cabinet for one week. The retinol remaining at different time points was measured by UV-visible spectrophotometry at 320 nm (mean±SD; n=3). The nanoparticles were prepared using the method as described in FIG. 19.

FIG. 25 illustrates the liquid state stability of retinol loaded nanoparticles when stored under normal room light. Free retinol and retinol nanoparticles were dispersed in phosphate buffer (pH 7.4) and stored in a clear glass vials in room light for one week. The retinol remaining at different time points was measured by UV-visible spectrophotometry at 320 nm (mean±SD; n=3). The nanoparticles were prepared using the method as described in FIG. 19.

FIG. 26 illustrates the liquid state stability of retinol loaded nanoparticles when stored protected from light in dark cabinet. Free retinol and retinol nanoparticles were dispersed in phosphate buffer (pH 7.4) and stored in a clear glass vials in a dark cabinet for one week. The retinol remaining at different time points was measured by UV-visible spectrophotometry at 320 nm (mean±SD; n=3). The nanoparticles were prepared using the method as described in FIG. 19.

FIG. 42 illustrates by means of a flow chart the general steps for preparing retinol loaded zein nanoparticles stabilized with casein, using a phase separation method, according to one embodiment.

DETAILED DESCRIPTION OF THE INVENTION

Figure 1:
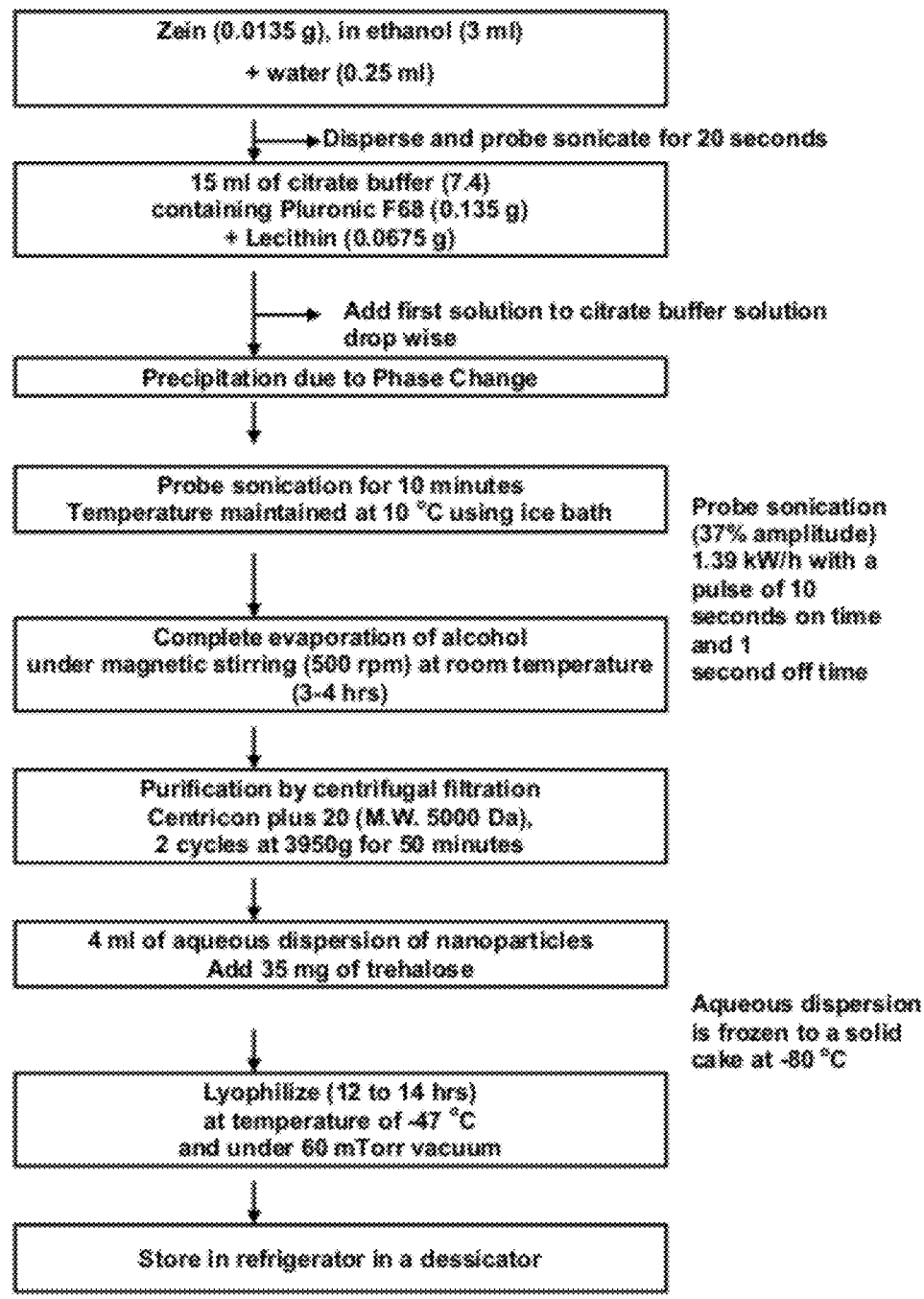
FIG. 1 illustrates by means of a flow chart the general steps of forming blank zein nanoparticles, according to one embodiment. The specific amounts recited in this and other figures are for illustration of a particular embodiment, and many variations can be applied to the procedures described herein, as would be readily recognized by one skilled in the art.

Novel nanocarriers for topical delivery of retinol through skin for treating various dermatological conditions and follicular disorders have been developed. Examples of such conditions include but are not limited to acne, psoriasis, keratinization disorders, skin discoloration, and cutaneous malignancies (skin cancer and melanoma), as well as for wound healing and photoaging (Orfanos et al., Drug 53:358-388, 1997). For example, the nanoparticles as described herein may be used for the delivery of protein drugs and the nanoparticles may be used with antibodies directed to IL-8 or anti-sense oligonucleotides which bind to intercellular adhesion molecule-1 mRNA. Other examples include cell composition such as platelet rich plasma (PRP), which can be used to administer various growth factors to select tissues, and small molecules such as retinoids.

Retinol (Vitamin A) and its derivatives (retinoids) are involved in various biological functions in the body including epidermal cell growth and differentiation, vision, immumomodulatory and anti-inflammatory effects (Summer, J Nutr 138:1835-1839, 2008). In particular, retinol and its derivatives are widely used for treating various dermatological conditions including acne, psoriasis, keratinization disorders, skin discoloration, and cutaneous malignancies (skin cancer and melanoma), as well as for wound healing and photoaging (Orfanos et al., Drug 53:358-388, 1997). Retinol is also used in cosmetic formulations to reduce wrinkles and treat cellulite (Orfanos et al., Drug 53:358-388, 1997). However, the use of retinol for cosmetic and dermatological applications is severely limited by its poor physicochemical properties and skin irritation potential (Melo et al., J Control Release 138: 32-39, 2009; Kim et al., Toxicol Lett 146:65-73, 2003).

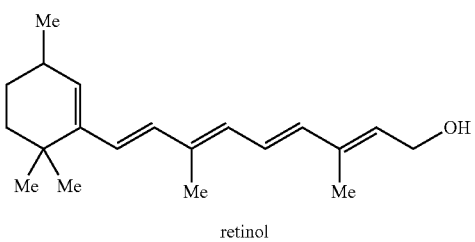 [SMILES: CC(/C=C/C1=CC(C)CCC1(C)C)=C\C=C\C(C)=C\CO]

retinol

Retinol is lipophilic molecule (Log P 6.20), with poor water solubility and limited skin permeability. Furthermore, it is highly unstable in presence of light and moisture (see U.S. Pat. No. 5,851,538 (Froix et al.), herein incorporated in its entirety). The topical application of retinol causes severe local irritation manifested as mild erythema and stratum corneum peeling, leading to non-compliance among users (Kim et al., Toxicol Lett 146:65-73, 2003). Applicants have successfully addressed the delivery issues of retinol by encapsulating retinol in novel protein based nanocarriers for topical application.

Novel nanocarriers have been developed from the corn protein zein, as described herein. Zein displays hydrophobicity similar to skin keratin (Deo et al., Langmuir 19:5083-5088, 2003) and hence is a promising carrier for skin applications. Because zein is hydrophobic, it can be used to encapsulate hydrophobic retinoids inside the nanoparticles as described herein, and zein can be used to encapsulate hydrophobic retinoids to provide a water removable formulation of a retinoid.

The nanoparticles provide flexibility in choice of retinol formulations for various topical applications. Applicants have prepared retinol loaded zein nanoparticles in the size range of about 100 nm to about 300 nm with an encapsulation efficiency of 76-100%. Retinol loaded nanoparticles are in the size range of 180-220 nm with an encapsulation efficiency of 79-91%. Encapsulation of retinol in the nanocarriers resulted in water dispersibility formulations.

Zein nanoparticles significantly enhanced the solid state and liquid state stability of retinol against moisture and light induced degradation. Retinol release was sustained up to a week from zein nanoparticles. Zein is a biodegradable US-FDA approved protein polymer with similar characteristics to skin keratin and is therefore a skin compatible nanocarrier. Nanoparticles also enhanced the skin penetration of retinol compared to free retinol aqueous dispersion. Zein nanoparticles can be used to retain retinol in the layers of the skin for cosmetic and dermatological applications.

A unique aspect of nanocarriers is the ability of the nanoparticles to address multiple market challenges for topical delivery of retinol. These challenges include providing 1) water soluble and water dispersible formulations of retinol, 2) enhanced stability of retinol against light and moisture induced degradation, 3) a freely flowing, colorless and non hygroscopic powder of retinol, 4) sustained release formulations of retinol, 5) higher skin penetration and higher skin penetration of retinol, and 6) non-irritating formulations of retinol.

Retinol water dispersibility is significantly increased after encapsulation in nanoparticles. The retinol release can be sustained from zein nanoparticles leading to lower dose and reduced frequency of application. The encapsulation of retinol in zein nanoparticles significantly increases the shelf-life of retinol formulations. Zein nanoparticles increase the flowability and dispersibility of retinol in solid and semi-solid formulations. Because retinol is a hygroscopic sticky powder, the encapsulation of retinol in nanoparticles can overcome the difficult handling and processing issues associated with retinol.

The stratum corneum (SC) is the top layer of the skin while the deeper layers of the skin include the viable epidermis and the dermis. Zein nanoparticles can enhance the skin penetration and retention of retinol in the layers of the skin for cosmetic and dermatological applications. Encapsulation of retinol in zein nanoparticles masks the yellow color of retinol. This improves the aesthetic appeal of retinol formulations and prevents yellow staining. The lyophilized zein nanoparticles can be easily incorporated into various topical formulation matrices, such as gels, creams, lotions and ointments.

The skin penetration studies were carried out with excised pig skin, which is similar to human skin in many important respects (Simon and Maibach, Skin Pharmacol. Appl. Physiol. 13:229-234, 2000.). In vivo studies in mice further demonstrate the ability of the nanoparticles to reduce the skin irritation of retinol. Advantages of using the nanoparticles in place of current commercial formulations include:

1. Solubilization. Retinol is a water insoluble hydrophobic compound. The encapsulation of retinol in zein nanoparticles is water dispersible. Hence nanoparticles can be used to develop water washable retinol formulation for topical applications. Generally water washable formulation is preferred for cosmetic and dermatological applications.

2. Stabilization. Retinol is highly unstable in presence of moisture and light. This limits the shelf-life of retinol formulations and efficacy of the formulation during application. Encapsulation of retinol in nanoparticles can significantly enhance the stability and shelf-life of retinol formulations.

3. Sustained Release. Retinol release can be sustained from zein nanoparticles. Release can be sustained for up to a week. This reduces the dose and frequency of application of retinol.

4. Skin penetration and retention. Retinol has poor skin penetration properties. Nanoparticles lead to enhanced skin penetration of retinol. Retinol can be retained in the layers of the skin using nanoparticles for various dermatological/cosmetic applications.

5. Cosmecutical applications. Retinol loaded nanoparticles can be used for cosmetic applications such as anti-aging, anti-wrinkle, and cellulite treatments.

6. Dermatological applications. Retinol loaded nanoparticles can be used for various dermatological conditions such as psoriasis, acne, wound-healing and cutaneous malignancies, such as skin cancer and melanoma.

7. Efficacious and safe formulation. Use of retinol loaded nanoparticles results in more efficacious treatments. Furthermore, the encapsulation of retinol in the nanoparticles can significantly reduce the skin irritation caused by retinol. Skin irritation of retinol is a major issue for non-compliance for cosmetic and dermatological applications of retinol.

8. Platform technology for encapsulation of other retinoids. Various retinoids including retinol, retinoic acid, and their derivatives (such as fatty acid esters), can be encapsulated in prolamine nanoparticles for cosmetic and dermatological applications. Examples of various retinoids suitable for encapsulation include, but are not limited to, retinol, retinoic acid (such as 13-cis-retinoic acid and/or 13-trans-retinoic acid), retinaldehyde, tretinoin, isotretinoin, etretnate, acitretin, retinyl acetate, retinyl palmitate, and carotenoids such as α-carotene, β-carotene, γ-carotene, β-cryptozanthin, lutein, and zeaxanthin.

9. Combination therapies. Retinol nanoparticles can be incorporated into other products, such as sunscreens, anti-psoriatic, anti-acne and skin-cancer products along with other drugs. Since retinol is encapsulated it will prevent the interaction with other agents. Other agents such as anti-oxidants, free-radical scavengers, anti-inflammatory agents can also be encapsulated along with retinol in nanoparticles. Such agents can include, but are not limited to, Vitamin E and its derivatives such as tocopheryl acetate, Vitamin C and its derivatives such as ascorbyl palmitate, green tree extract, aloe vera, Coenzyme Q10, hydroquinone, hyaluronic acid, sodium hyaluronate, bisabolol, glycolic acid, lactic acid, beta hydroxybutanoic acid, salicylic acid, 10-hydroxy decanoic acid, ferulic acid, pantethenol, biotic, arbutin, quercetin, hesperidin, and combinations thereof.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The terms "comprising," "including," "having," "containing," "characterized by," and grammatical equivalents thereof, are inclusive or open-ended terms that do not exclude additional, unrecited elements or method steps, but also include the more restrictive terms "consisting of and "consisting essentially of".

The singular forms "a," "an," and "the" include plural reference unless the context clearly dictates otherwise. Thus, for example, a reference to "a compound" (e.g., a drug) includes a plurality of such compounds, so that a compound X includes a plurality of compounds X. As an additional example, reference to "a nanoparticle" can include a plurality of such nanoparticles, and reference to a "molecule" is a reference to a plurality of molecules, and equivalents thereof. It is further noted that the claims may be drafted to exclude any optional element. As such, this statement is intended to serve as antecedent basis for the use of exclusive terminology, such as "solely", "only", and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" or "approximately" means reasonably close to, or a little more or less than, a recited number or amount. Thus, the term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless otherwise indicated herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value or identity within the range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "zein" refers to a member of the class of prolamine proteins. Prolamines are found in various grains such as corn, wheat, barley, rice, and sorghum, as well as in other plants and animals. Other examples of prolamines include gliadin, hordein and kafirin. These prolamines can be exchanged for zein in the various embodiments described herein. Zein is composed of a high proportion of non-polar amino acids, such as proline, glutamine and asparagine, and has a molecular weight of about 22-27 kDa (Shukla, Zein: the industrial protein from corn, Ind Crops Prod 13, 171-92; 2001), and can be a mixture of three distinct proteins with varying molecular weights. A typical sample of zein can have approximately 20% leucine, 10% proline, 21-26% glutamine, 5% asparagine, and 10% alanine, therefore at least about 61% of its amino acid composition is of hydrophobic amino acids. These hydrophobic amino acids render the protein water insoluble. Zein is a biodegradable US-FDA approved GRAS polymer (Fed Register (1985) 50:8997-8999).

Zein can be manufactured as a powder from corn gluten meal. Pure zein is odorless, tasteless, water-insoluble, and edible, properties which have rendered it an important component for processed foods and pharmaceuticals. Methods for isolating, processing, and using zein are known in the art. See for example, Lawton, Cereal Chem 2002, 79(1): 1-18, and WO2009/137112 (Perumal et al.), which are incorporated herein by reference in their entireties. A "grade" of zein refers to a variety of types or forms of zein, including white zein and yellow zein, derived by various means, such as is disclosed in U.S. Pat. No. 5,254,673 (Cook et al.), the contents of which are incorporated by reference in its entirety.

The term "biocompatible" means that the polymer or conjugate referred to does not cause or elicit significant adverse effects when administered in vivo to a subject. Examples of possible adverse effects include, but are not limited to, excessive inflammation and/or an excessive or adverse immune response, as well as toxicity. Zein is a biocompatible component.

The term "nanoparticle" is generally known to refer to a particle that is not more than 1000 nm in at least one dimension. However, the nanoparticles formed by the methods of the present invention will have a diameter of a specified value as defined herein. Further, the use of the term "nanoparticle" is also meant to refer generically to blank nanoparticles and nanoparticles loaded with a molecule and formed by methods of the present invention. As used herein, unless defined otherwise (i.e., FIG. 11), "blank nanoparticle" refers to nanoparticles that do not have a selected particle, molecule or material formed with or in conjugation with the nanoparticle.

The term "diameter" when used in the context of nanoparticle dimensions refers to the mean linear dimension of the particle for lines passing through the center of mass of the particle. Acceptable approximation of the diameter of non-spherical particles may be provided, for example, by taking the mean of the thickness of the particle along three orthogonal axes of a coordinate system, with one of the axes aligned with the longest dimension of the particle.

The term "hydroalcoholic solvent" refers to a solvent system that includes both water and an alcoholic solvent, such as methanol, ethanol, n-propanol, iso-propanol, or butanol (including 1-butanol, 2-butanol (sec-butanol), iso-butanol, and tert-butanol). Common hydroalcoholic solvent systems include 50%, 70%, 90%, and 92% ethanol in water.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro or in vivo.

The term "in vivo" means of or within the body of a subject, such as that of a patient, and includes administration of nanoparticles by a variety of means including, but not limited to, oral, intravenous, intratumorally, peritumorally, intraperitoneal, parenteral, subcutaneous, topical, ocular, pulmonary and nasal routes of administration.

The term "in vitro" refers to environments outside of the body of a subject or patient.

The term "in situ" refers to the original position; not having been moved or transferred to another location.

The term "associating" refers to the complexing of cargo or cargo molecules to the nanoparticles of the instant disclosure, and include but are not limited to, conjugation (covalent or non-covalent) to the surface or interior regions of the particle, adsorption, and encapsulation.

The term "complexing", including grammatical variations thereof, refers to the combination of various cellular or molecular entities with the nanoparticles of the present disclosure.

The term "administered" or "administration", when used in the context of therapeutic and diagnostic uses for nanoparticles, refers to and includes the introduction of a selected amount of nanoparticles into an in vivo or in vitro environment for the purpose of, for example, delivering a therapeutic agent to a targeted site.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a blank or drug loaded nanocarrier (i.e., nanoparticle) described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can includes both medical, therapeutic, and/or prophylactic administration, as appropriate.

The terms "subject" or "patient" both refer to or mean an individual complex organism, e.g., a human or non-human animal.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "therapeutic agent," and similar terms referring to a therapeutic or medicinal function, means that the referenced molecule, macromolecule, drug or other substance can beneficially affect the initiation, course, and/or one or more symptoms of a disease or condition in a subject, and may be used in conjunction with nanoparticles in the manufacture of medicaments for treating a disease or other condition. Suitable therapeutic agents for encapsulation in or absorption on the nanoparticles described herein include hydrophobic therapeutic agents, such as, but not limited to, retinoids, such as retinol and esters thereof, and derivatives of retinol, such as retinoic acid and retinal, small molecules, antibodies, nucleic acids, proteins, hormones, receptors, ligands, cells (e.g., platelet rich plasma (PRP)), growth factors, cell extracts, and the like.

The term "therapeutic agent," and similar terms referring to a therapeutic or medicinal function mean that the referenced molecule, macromolecule, drug or other substance can beneficially affect the initiation, course, and/or one or more symptoms of a disease or condition in a subject, and may be used in conjunction with nanoparticles in the manufacture of medicaments for treating a disease or other condition.

Retinol ($C_{20}H_{30}O$; 286.45 g/mol) is a diterpenoid alcohol that has important biological activity. Retinol has a melting point of 61-63° C., an activity of 3100 units/mg, and a Log P of 6.2. Retinol is practically insoluble in water, is soluble or partly soluble in ethanol, and is miscible with chloroform, ether and petroleum spirits. Retinol is a cosmecutical/therapeutic agent used for various skin conditions including photoaging, acne, wound healing, melasma psoriasis, skin cancer, melanoma and other skin conditions (Orfanos et al., Drug 53:358-388, 1997). Retinol has poor water solubility and poor photostability (Melo et al., J Control Release 138:32-39, 2009; U.S. Pat. No. 5,851,538 (Froix et al.), herein incorporated by reference in its entirety). In addition, it also causes skin irritation (Kim et al., Toxicol Lett. 146:65-73, 2003).

Nanoparticles and Preparatory Methods

The invention provides nanoparticles that can be formed from a hydrophobic water-insoluble protein such as prolamine, for example, zein. The nanoparticles can be employed to provide a nanoparticles formulation that lacks the immunogenicity experienced in the use of larger-sized nanoparticles or microparticles, including those formed from, for example, hydrophobic water-insoluble proteins. The non-immunogenic effect of the nanoparticles can be achieved by controlling the size of the particles, as well as the range of particle sizes.

FIG. 1 illustrates by means of a flow chart general steps for preparing non-immunogenic nanoparticles, according to one embodiment. The specific amounts used are for illustration, and many variations can be applied to the procedures described herein, as would be readily recognized by one skilled in the art. In an initial step or phase of the method, a water-insoluble protein (0.4 to 1.25% w/v) is dissolved in a hydroalcoholic solvent (e.g., a combination of ethanol and deionized water). The composition of the solvent may be, for example, 90%:10% v/v or 92%:8% v/v, alcohol to water. For methods where a selected molecule is to be encapsulated in the nanoparticle, the molecule (0.03 to 0.3% w/v) to be encapsulated is added to the solution of this first aqueous phase. The molecule to be encapsulated can be approximately to 50% w/w of the protein polymer.

The pH of the solution can be altered, for example, to bring the pH of the solution to between about pH 6 and about pH 7 by the addition of 0.01N NaOH or 0.01N HCl. If the water pH changes after addition of an acidic molecule, such as retinoic acid, or by a basic molecule, the pH can be readjusted to pH 6-7. The solution of the first phase can be processed, for example, by probe sonication, to aid is the dissolution of the protein.

In a subsequent step of the method, the aqueous solution of the initial step or phase can be added to a buffering agent, optionally under ultrasonic shear. Citrate buffer is suitable buffer. The choice of the buffering agent used for the second aqueous phase is significant for maintaining the pH during nanoparticle formation and for subsequent lyophilization of the formed nanoparticles, as described later in this disclosure. If no buffer is used, or if, for example, 0.1N HCl is used to adjust the pH of the second aqueous phase solution, the particles produced tend to be larger than those produced with the citrate buffer, and the particles tend to demonstrate a wider size range. Use of a citrate buffer produces some of the smallest particle diameter sizes, such as approximately 100 nm. Use of other buffers may produce particles in the same or similar diameter size range of approximately 100 nm to approximately 300 nm, but after the lyophilization step, the average size of the nanoparticles formed using other buffering agents have been know to increase by two to three times.

The pH of the second aqueous phase solution can be adjusted to be between about pH 6.8 and about pH 7.4 to obtain the desired size of nanoparticles. If the pH is outside of this range, the particle size tends to become larger, and the polydispersity index (PDI) of the particles produced becomes higher. The PDI is a measure of the distribution of the particles in different size ranges. The method thus can use the solubility difference of a protein, such as zein, in the hydroalcoholic solution and an aqueous solution with a selected pH of approximately 6.8 to approximately 7.4, close to the isoelectric point of zein (i.e., pI 5 to 9).

The addition of a buffering agent to the second aqueous phase solution may be performed under high ultrasonic shear or under high pressure homogenization, or a combination of both ultrasonic shear and high pressure homogenization. The ultrasonic energy and duration of ultrasonic shear may be particularly significant to the formation of particles in the desired diameter size ranges. The ultrasonic shear energy may be carried out, for example, from 0.6 kW/h to 1.39 kW/h, for a duration of approximately 2 to 10 minutes with a pulse on-time of from 5 to 10 seconds and an off-time of from 1 to 5 seconds. The ultrasonic processing may be significant to the production of particles in the desired size range. When employing high pressure homogenization, the process may be carried out using an orifice size of between 0.1 mm and 0.25 mm, and for a time period of between five to ten minutes at a pressure of from 5000 to 40,000 psi.

The buffering agent of the second phase may also preferably contain a surfactant and a phospholipid in a selected ratio. The ratio of surfactant to phospholipid may be approximately 2:1% w/w, which produces the highly suitable results. The ratio may also be 1:0.5% w/w or 1:1% w/w or 1:2% w/w. Significantly, the combination of a surfactant and a phospholipid is desirable to stabilize the particles produced and to help prevent aggregations of the particles.

The surfactant can be, for example, a poloxamer, such as PLURONIC® F68, and the phospholipid can be lecithin. Other surfactants that may be used in the methods include other nonionic surfactants such as poloxamers (PLURONIC®), polyoxyethylene alkyl ethers (BRIJ), sorbitan esters (SPAN), polyoxyethylene sorbitan fatty acid esters (TWEEN), and ionic surfactants such as sodium dioctyl sulfosuccinate, sodium lauryl sulfate, benzalkonium chloride, cetyl trimethyl ammonium bromide, N-dodecyl trimethyl ammonium bromide, and/or polymer such as polyvinyl alcohol, polyvinyl pyrrolidone. Other phospholipids that may be used in the methods include non-ionic and charged lipids or phospholipids such as egg lecithin, soy lecithin, phosphatidyl choline, phosphatidyl ethanolamine, 1,2-dioleoyl-3-trimethyl ammonium propane, casein, or a combination thereof.

A combination of poloxamer and lecithin (e.g., 0.9% w/w: 0.45% w/w) in the selected ratio has been found to produce nanoparticles in the desired diameter size range of about 100 nm to about 300 nm. Use of either of the surfactant or phospholipid alone has generally been found to result in larger particle sizes outside of the desired diameter size range. However, use of either a surfactant or a phospholipid in accordance with the methods described herein can result in nanoparticles of a desired size for non-immunogenicity.

In embodiments, zein nanoparticles may be stabilized by casein and gum *Arabica* using pH controlled nanoprecipitation. In other embodiments, zein nanoparticles may be complexed with dextran using DMSO to generate zein-dextran nanoparticles.

After the application of ultrasonic shear or/or high pressure homogenization to the solution of the second phase, the mixture can be stirred to evaporate the ethanol or other solvent to form the nanoparticles. In one embodiment, the stirring can be performed by, for example, a mechanical stirrer, at a rate of from approximately 300 rpm to approximately 500 rpm at room temperature (~23° C.) for approximately one to six hours, or about hours.

The nanoparticles can then be subjected to ultracentrifugal filtration for the purpose of separating the nanoparticles from any residual material. Ultracentifugation may be carried out using centrifugal filters of molecular weight cut-off of about 5 kDa (or other appropriate filters with a higher or lower Mwt cut-off than 5 kDa), and at between 2 kDa and 40 kDa, depending on the encapsulated molecule or drug, or on the particular treatment of the nanoparticles, such as PEGylation. The time of the ultracentrifugation can vary, for example, from about 20 to about 50 minutes. A cryoprotectant may then be added to the nanoparticles. For example, 2% w/v trehalose can be added as a cryoprotectant. Other cryo- or lyo-protectants can also be used, such as sugars, including glucose, sucrose, lactose, ficoll, betaine, or poyols such as mannitol or sorbitol. The nanoparticles can be maintained at, for example, −80° C. to form a solid cake, which can then be lyophilized, such as by drying the nanoparticles in a frozen state under high vacuum. The duration of ultrasonic energy, type of surfactant, concentration of surfactants, and buffer may be varied according to desired parameters, as would be readily recognized by one skilled in the art.

Accordingly, the range of particle diameter sizes of the nanoparticles described herein can be less than approximately 400 nm, or less than, approximately 300 nm. In some embodiments, the range of particle diameter sizes is approximately 100 nm to approximately 300 nm, or approximately 75 nm to approximately 300 nm. While size is discussed in terms of a diameter, the nanoparticles are not necessarily perfectly spherical in shape, although spherical shapes in the nanoparticles can be achieved and can be typical of some embodiments. The dimensions can be measured between opposite sides of the particle, for example, the largest dimension across the particle from opposite sides, or the average of the largest dimension across the particle from opposite sides and the smallest dimension across the particle from opposite sides.

Water-insoluble hydrophobic proteins use for the nanoparticles can be derived from a variety of sources including plant, animal and synthetic sources. In some embodiments, the protein can be from the family of prolamines, which are composed of high amounts of hydrophobic amino acids such as, for example, proline, glutamine and asparagine. These hydrophobic amino acids render the protein water-insoluble. Prolamines can be found in various grains such as corn, wheat, barley, rice, sorghum, and in other plants and animal sources. Some examples of suitable prolamines include, but are not limited to, zein, gliadin, hordein and kafirin.

In some embodiments, white zein can be used to produce suitable nanoparticles, such as those having a diameter of about 100 nm to about 400 nm. Yellow zein can produce particles with relatively larger diameter sizes, and can also produce particles with wider particle diameter size distribution. The pigments in yellow zein may affect the solubility of the yellow zein and nanoparticle formation using yellow zein.

Methods of preparing nanoparticles of a generally smaller diameter size and narrower diameter size range than would otherwise be possible are described herein. These smaller nanoparticles can be prepared by implementing a pH-controlled nanoprecipitation process using one or more particular grades of a base protein, such as zein, and by using various combinations of buffers, surfactants, and phospholipids that are selected to achieve nanoparticle sizes and diameters that render the nanoparticles non-immunogenic.

The nanoparticles can be prepared with a wide variety of “cargo” or “cargo molecules”. For example, particles or agents, having varying physicochemical properties, can be added in the preparation of the protein nanoparticles to provide encapsulated, adsorbed, complexed and/or conjugated materials with the nanoparticles. The particles can entrap small hydrophilic molecules, small hydrophobic molecules, and/or macromolecules. An encapsulation efficiency of approximately 60% to approximately 80% or greater can be achieved. The nanoparticles can provide sustained delivery of the encapsulated molecule one to seven days, or one to two weeks, in an in vitro or in vivo environment. In some embodiments (e.g., proteins/antibodies and the like), cargo may be adsorbed/complexed/conjugated to the surface of the nanoparticle.

In embodiments, cargo or cargo molecules are pharmaceutical materials. Such materials which are suitable for use with the present nanoparticles as encapsulated cargo or cargo molecules, complexed or conjugated cargo molecules or adsorbed cargo molecules include any materials for in vivo or in vitro use for diagnostic or therapeutic treatment of a subject which can be associated with the nanoparticle without appreciably disturbing the physical integrity of the nanoparticle, for example: drugs, such as antibiotics, analgesics, hypertensives, cardiotonics, steroids and the like, such as acetaminophen, acyclovir, alkeran, amikacin, ampicillin, aspirin, bisantrene, bleomycin, neocardiostatin, chloroambucil, hydroxycoumarin, chloramphenicol, cytarabine, daunomycin, 5-fluorouracil, cisplatin, carboplatin, fluorouracil, taxol, gemcitabine, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, trimethoprim, and valbanl; toxins, such as diphtheria toxin, gelonin, exotoxin A, abrin, modeccin, ricin, or toxic fragments thereof; metal ions, such as the alkali and alkaline-earth metals; radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, 90Y, $^{99}$mTc, $^{105}$Rh, $^{109}$Pd, $^{111}$In, $^{125}$I, $^{131}$I, $^{140}$Ba, $^{140}$La, $^{149}$Pm, $^{153}$Sm, $^{59}$Gd, $^{166}$Ho, $^{175}$Yb, $^{177}$Lu, $^{186}$Re, $^{188}$Re, $^{194}$Ir, and $^{199}$Au; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; chelated metal, such as any of the metals given above, whether or not they are radioactive, when associated with a chelant; signal absorbers, such as near infared, contrast agents (such as imaging agents and MRI agents) and electron beam opacifiers, for example, Fe, Gd or Mn; antibodies, including monoclonal or polyclonal antibodies and anti-idiotype antibodies; antibody fragments; aptamers; hormones; biological response modifiers such as interleukins, interferons, viruses and viral fragments; diagnostic opacifiers; and fluorescent moieties. Cargo molecules include scavenging agents such as chelants, antigens, antibodies, aptamers, or any moieties capable of selectively scavenging therapeutic or diagnostic agents.

In other embodiments, the cargo or cargo molecules are agricultural materials. Such materials which are suitable for use with the nanoparticles as described herein include any materials for in vivo or in vitro treatment, diagnosis, or application to plants or non-mammals (including microorganisms) which can be associated (i.e., encapsulated, conjugated or adsorbed) with the nanoparticles without appreciably disturbing the physical integrity of the nanoparticles. For example, the cargo molecules can be toxins, such as diphtheria toxin, gelonin, exotoxin A, abrin, modeccin, ricin, or toxic fragments thereof; metal ions, such as the alkali and alkaline earth metals; radionuclides, such as those generated from actinides or lanthanides or other similar transition elements or from other elements, such as $^{47}Sc$, $^{67}Cu$, $^{67}Ga$, $^{82}Rb$, $^{89}Sr$, $^{88}Y$, $^{90}Y$, $^{99m}Tc$, $^{105}Rh$, $^{109}Pd$, $^{111}In$, $^{125}I$, $^{131}I$, $^{140}Ba$, $^{140}La$, $^{149}Pm$, $^{153}Sm$, $^{59}Gd$, $^{166}Ho$, $^{175}Yb$, $^{177}Lu$, $^{186}Re$, $^{188}Re$, $^{194}Ir$, and $^{199}Au$; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such contrast agents and as electron beam opacifiers, for example, Fe, Gd, or Mn; hormones; biological response modifiers, such as gibberellins, cytokinins, auxins, ethylene, abscisic acid, viruses and viral fragments, plasmids, plastids; pesticides, including antimicrobials, algicides, arithelmetics, acaricides, insecticides, attractants, repellants, herbicides and/or fungicides, such as acephate, acifluorfen, alachlor, atrazine, benomyl, bentazon, captan, carbofuran, chloropicrin, chlorpyrifos, chlorsulfuron cyanazine, cyhexatin, cypermithrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam; pendimethalin, permethrin, picloram, propachlor, propanil, sethoxydin, temephos, terbufos, trifluralin, triforine, zineb, and the like. Cargo or cargo molecules include scavenging agents such as chelants, chelated metal (whether or not they are radioactive) or any moieties capable of selectively scavenging agricultural agents.

In another embodiment, the cargo or cargo molecules are immuno-potentiating agents. Such materials which are suitable for use with the nanoparticles as described include any antigen, hapten, organic moiety or organic or inorganic compounds which will raise an immuno-response which can be associated with (i.e., encapsulated, conjugated or adsorbed) the nanoparticles without appreciably disturbing the physical integrity of the nanoparticles. For example, the carried materials can be synthetic peptides used for production of vaccines against malaria (U.S. Pat. No. 4,735,799, herein incorporated by reference in its entirety), cholera (U.S. Pat. No. 4,751,064, herein incorporated by reference in its entirety) and urinary tract infections (U.S. Pat. No. 4,740,585, herein incorporated by reference in its entirety), bacterial polysaccharides for producing antibacterial vaccines (U.S. Pat. No. 4,695,624, herein incorporated by reference in its entirety) and viral proteins or viral particles for production of antiviral vaccines for the prevention of diseases such as AIDS and hepatitis.

The use of these nanoparticles as carriers for immuno-potentiating agents avoids the disadvantages of ambiguity in capacity and structure associated with conventionally known classical polymer architecture or synthetic polymer conjugates used to give a macromolecular structure to the adjuvant carrier. Use of these nanoparticles as carriers for immuno-potentiating agents, allows for control of the size, shape and surface composition of the conjugate. These options allow optimization of antigen presentation to an organism, thus resulting in antibodies having greater selectivity and higher affinity than the use of conventional adjuvants. It may also be desirable to connect multiple antigenic peptides or groups to the nanoparticle, such as attachment of both T- and B-cell epitopes. Such a design would lead to improved vaccines.

It may also be desirable to conjugate pesticides or pollutants capable of eliciting an immune response, such as those containing carbamate, triazine or organophosphate constituents, to a nanoparticle. Antibodies produced to the desired pesticide or pollutant can be purified by standard procedures, immobilized on a suitable support and be used for subsequent detection of the pesticide or pollutant in the environment or in an organism.

In embodiments, the cargo or cargo molecules include any materials other than agricultural or pharmaceutical materials which can be associated with these nanoparticles without appreciably disturbing the physical integrity of the nanoparticles, for example: metal ions, such as the alkali and alkaline-earth metals; signal generators, which includes anything that results in a detectable and measurable perturbation of the system due to its presence, such as fluorescing entities, phosphorescence entities, infrared, near infrared, and radiation; signal reflectors, such as paramagnetic entities, for example, Fe, Gd, or Mn; signal absorbers, such as contrast agents and an electron beam opacifiers, for example, Fe, Gd, or Mn; pheromone moieties; fragrance moieties; dye moieties; and the like. Cargo molecules include scavenging agents such as chelants or any moieties capable of selectively scavenging a variety of agents.

The cargo or cargo molecules may be bioactive agents. As used herein, "bioactive" refers to an active entity such as a cell (e.g., stem cells, platelet rich plasma, including microenvironment/scaffold for stem cells or cell culture), molecule, atom, ion and/or other entity which is capable of detecting, identifying, inhibiting, treating, catalyzing, controlling, killing, enhancing or modifying a targeted entity such as a protein, glycoprotein, lipoprotein, lipid, receptor, a targeted disease site or targeted cell, a targeted organ, a targeted organism [for example, a microorganism, plant or animal (including mammals such as humans)] or other targeted moiety. Also included as bioactive agents are genetic materials (of any kind, whether oligonucleotides, fragments, or synthetic sequences) that have broad applicability in the fields of gene therapy, siRNA, diagnostics, analysis, modification, activation, anti-sense, silencing, diagnosis of traits and sequences, and the like. These cargo molecules include effecting cell transfection and bioavailability of genetic material comprising a complex of a nanoparticle and genetic material and making this complex available to the cells to be transfected.

These nanoparticles may be used in a variety of in vivo, ex vivo or in vitro diagnostic or therapeutic applications. Some examples are the treatment of diseases such as cancer, autoimmune disease, genetic defects, central nervous system disorders, infectious diseases and cardiac disorders, diagnostic uses such as radioimmunossays, electron microscopy, PCR, enzyme linked immunoadsorbent assays, nuclear magnetic resonance spectroscopy, contrast imaging, immunoscintography, and delivering pesticides, such as herbicides, fungicides, repellants, attractants, antimicrobials or other toxins. Non-genetic materials are also included such as growth factors, hormones, chemokines, cytokines, interleukins, interferons, tumor necrosis factor, granulocyte colony stimulating factor, and other protein or fragments of any of these, antiviral agents.

The invention also provides therapeutic and/or cosmetic nanoparticles, such as nanoparticles containing an active agent (drug) or cosmetic agent. The nanoparticles can provide targeted delivery and temporal control of the release of the agent. The agent can be, for example, an agent effective to treat skin conditions or disorders, for example, retinol or retinoic acid, antibodies, oligonucleotides, cell formulations, and the like among other agents described herein.

The invention also provides a kit for the preparation of nanoparticles described herein. The kit can contain a selected amount of a water-soluble protein, one or more buffering agents, one or more surfactants, a hydroalcoholic solvent for dissolving the protein, or a combination thereof. The kit may also include one or more phospholipids, the amount of which may be sufficient to provide a selected ratio of phospholipids to surfactant.

The invention therefore provides nanoparticles encapsulating various agents and methods of preparing them. In one embodiment, the method can be for producing non-immunogenic nanoparticles. The method can include providing a hydrophobic water-insoluble protein; dissolving the protein with a hydroalcoholic solvent to provide a first aqueous phase solution; adding a buffering agent to the first aqueous phase solution in the presence of a surfactant and a phospholipid to produce a second aqueous phase solution having a pH of between approximately pH 6.8 and approximately pH 7.4; processing the second aqueous phase solution to effect a reduction in diameter size of particles within the dispersion; evaporating any residual solvent to produce nanoparticles having a diameter size of less than approximately 400 nm. The nanoparticles can then be centrifuges for isolation and collection.

The method can include lyophilizing the nanoparticles following centrifugation. The method can further include storing the nanoparticles under conditions that restrict exposure of the nanoparticles to atmospheric pressure. The base protein can be, for example, a selected grade of zein, such as white zein.

The buffering agent can be a citrate buffer. The surfactant can be a poloxamer and the phospholipid can be lecithin. The ratio of surfactant to phospholipid can be about 2:1. The processing of the second aqueous phase solution to effect a reduction in diameter size of particles can further include subjecting the nanoparticles to ultrasonic shear, high pressure homogenization, or a combination thereof. For other nanoparticle preparations, for example, surfactants may be absent (e.g., β-casein-dextran nanoparticles or zein-β-casein-gum Arabica nanoparticles) or other surfactants may be used (e.g., where sodium lauryl sulfate is used in addition to non-ionic surfactants to prepare zein nanoparticles).

The method can include adding to the protein in the formation of the first phase solution a molecule for nanoparticle encapsulation. The molecule can be a therapeutic substance selected for administration to a subject, to provide a therapeutically-active, non-immunogenic nanoparticle. The protein can also be PEGylated and/or cross-linked.

The invention further provides a therapeutic composition comprising a non-immunogenic nanoparticle formed by the encapsulation of a therapeutic molecule in a hydrophobic, water insoluble protein, the nanoparticle having a diameter of less than about 400 nm. In some embodiments, the diameter of the particles is about 100 nm to about 400 nm, or about 100 nm to about 300 nm. The invention also provides a pharmacologically therapeutic amount of a non-immunogenic nanoparticles comprising a therapeutic agent, the nanoparticles having average diameters of less than about 400 nm. The nanoparticles can be used for the manufacture of a medicament for use in the treatment of a disease or condition in a subject suffering from, or at risk of suffering from, the disease or condition that can be treated by the therapeutic agent (i.e., in need thereof).

Variations of Protein, Polymer, and Nanoparticle Components

Variations of the zein nanoparticles described herein can also be prepared. For example, in place of zein, other hydrophobic prolamine proteins, such as gliadin, hordein and kafirin may be used as the protein for nanoparticle formation. Accordingly, gliadin nanoparticles, hordein nanoparticles, and kafirin nanoparticles can be prepared and used similar to the zein nanoparticles described herein.

Additionally, the protein of the nanoparticles can be conjugated to moieties such as PEG to modify the surface of the nanoparticles. The surface modifying moiety can be PEG moieties or other water soluble polymers, such as polyvinylpyrrolidone (PVP), polyglycolic acid (PGA), polyvinyl alcohol (PVA), chitosan, dextran, polyethyleneimine (PEI), polysialic acid (PSA), polyacrylic acid (PAA), and the like. These water soluble polymers can be conjugated to any of the hydrophobic prolamine proteins, such as zein, gliadin, hordein and kafirin, to form surface modifications of the nanoparticles.

Similarly, hydrophobic polymers can be complexed, mixed or conjugated to a prolamine nanoparticle. Such polymers can include, for example, polycaprolactone, poly lactic acid-co glycolic acid, polypropylene oxide, polyaspartate, polyglutamate, spermine, polylysine, polyethylene imine or polyacrylates (for example, polymethacrylate, polydimethylamino ethyl acrylate, and the like). Natural polymers can also be complexed, mixed or conjugated to prolamine nanoparticle such as other protein polymers (albumin, caesin, gelatin, and the like), and carbohydrate polymers such as chitosan, dextran, gum *Arabica*, dextran-grafted casein, alginates or combinations thereof. Likewise, fatty acids can also be mixed, complexed or conjugated to a prolamine nanoparticles surface. Examples of such fatty acids can include stearic acid, palmitic acid, phosphatidyl ethanolamine, and/or oleic acid. These polymers and/or fatty acids can be conjugated to any of the hydrophobic prolamine proteins, such as zein, gliadin, hordein and kafirin, to form surface modified nanoparticles.

Because zein is a protein, a further advantage of using zein in formation of nanoparticles is realized in that zein has a large number of surface functional groups that can be used to attach targeting ligands, imaging agents, drugs and other polymers for drug targeting to specific tissues and other biomedical applications. Other or further modifications can be made to the prolamine hydrophobic core or to the nanoparticles surface. These may include conjugating stimuli responsive elements, such as polyhydroxyethylmethacrylate, to the nanoparticles to prepare pH sensitive nanoparticles or poly (N-isopropylacrylamide) to prepare thermosensitive nanoparticles. In addition, the prolamine nanoparticles can be cross-linked, for example, using cross-linkers such as glutaraldehyde, genipin, citric acid, polysialic acid (PSA), and the like, to control drug release and increase drug encapsulation yield and efficiency.

Zein nanoparticles formed using the methods described herein have particularly important uses outside of the body, e.g., for topical administration of a drug. For example, drug loaded zein nanoparticles can be used to encapsulate and sustain the release of molecules of interest, for example, to the cosmetic and pharmaceutical industries. The prolamine nanoparticles can be used to protect molecules from adverse environmental agents such as moisture, oxidation, light, and the like, and can also reduce the skin sensitivity of a patient to a particular drug. Prolamines can also be combined with other natural and synthetic polymers to design novel nanoparticles with unique properties for various topical applications, as described herein.

Pharmaceutical Formulations of Nanoparticles

The nanoparticles described herein can be used to prepare therapeutic pharmaceutical compositions. The nanoparticles may be added to the compositions in the form of an aqueous dispersion or as a dry powder of lyophilized nanoparticles. The nanoparticles can be formulated as pharmaceutical compositions and administered to a mammalian host, such as a human patient, in a variety of forms. The forms can be specifically adapted to a chosen route of administration, such as topical administration.

The nanoparticles described herein may be topically administered in combination with a pharmaceutically acceptable vehicle, such as an inert diluent or known topical carrier. Topical compositions and preparations typically contain at least 0.1 wt. % of an active therapeutic or diagnostic agent. The weight percentage of agent in the compositions and preparations can vary and may also conveniently be from about 2% to about 60% of the weight of a given unit dosage form. The amount of active compound in such therapeutically useful compositions containing nanoparticles is such that an effective dosage level can be obtained. Dispersions, aerosol formulations, gels, ointments, creams, lotions, shampoos and the like may also contain one or more of the following: binders such as gum tragacanth, acacia, corn starch or gelatin. A unit dosage form, in addition to materials of the above type, may include a liquid carrier, such as a vegetable oil or a polyethylene glycol. Various other materials may be present to modify the physical form a unit dosage form. A topical formulation may contain the nanoparticles, in addition to methyl and propyl parabens as preservatives, and optionally a dye to add color. Any material used in preparing a unit dosage form should be pharmaceutically acceptable and substantially non-toxic in the amounts employed. In addition, the nanoparticles dispersion or lyophilized nanoparticles may be incorporated into additional sustained-release preparations and devices.

Dispersions of the nanoparticles can be prepared in water, optionally mixed with a buffer, or in other pharmaceutically acceptable solvents, or mixtures thereof. Under ordinary conditions of storage and use, preparations may contain a preservative to prevent the growth of microorganisms. The ultimate dosage form should be sterile, fluid and stable under the conditions of manufacture and storage. The liquid carrier or vehicle can be a liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride in some formulations.

Sterile solutions can be prepared by incorporating the nanoparticles in the required amount in an appropriate solvent with various of the other ingredients enumerated above, as required, followed by filter sterilization. In the case of sterile powders for the preparation of sterile solutions, methods of preparation can include vacuum drying and freeze drying techniques, which yield a powder of the nanoparticles plus any additional desired ingredient present in the previously sterile-filtered solutions, gels, creams, lotions, ointments, and the like.

For topical administration, it will generally be desirable to administer the nanoparticles to the skin as a composition or formulation, for example, in combination with a dermatologically acceptable carrier, which may be a solid, liquid, gel, cream, ointment, or paste. Useful solid carriers include finely divided solids such as talc, clay, microcrystalline cellulose, silica, alumina, and the like. Useful liquid carriers include water, or water-alcohol/glycol/dimethyl sulfoxide (DMSO) blends, in which a nanoparticles can be dispersed at effective levels, optionally with the aid of non-toxic surfactants. Adjuvants such as fragrances and additional antimicrobial agents can be added to optimize the properties for a given use. Fluid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents (e.g., agent loaded nanoparticles) to the skin are known to the art; for example, see U.S. Pat. No. 4,608,392 (Jacquet et al.), U.S. Pat. No. 4,992,478 (Geria), U.S. Pat. No. 4,559,157 (Smith et al.), and U.S. Pat. No. 4,820,508 (Wortzman), each of which is incorporated by reference in their entireties. Such dermatological compositions can be used in combinations with the nanoparticles formulations described herein.

Useful dosages of drug loaded nanoparticles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.), incorporated by reference in its entirety. The amount of a compound, or an active salt, prodrug, or derivative thereof, loaded into a nanoparticle required for use in treatment will vary not only with the particular compound or salt selected but also with the route of administration, the nature of the condition being treated, and the age and condition of the patient, and will be ultimately at the discretion of an attendant physician or clinician.

The therapeutic agent loaded nanoparticle can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The drug loaded nanoparticles described herein can be effective anti-inflammatory agents and have higher potency and/or reduced toxicity as compared to non-nanoparticles encapsulated anti-inflammatory agents. The invention provides therapeutic methods of treating inflammation in a mammal, which involve administering to a mammal having inflammation (e.g., of the skin) an effective amount of a composition or formulation described herein. A mammal includes a primate, human, rodent, canine, feline, bovine, ovine, equine, swine, caprine, bovine and the like.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Nanoparticles according to various embodiments, such as those having average diameters of about 75 nm to about 400 nm were prepared and characterized as described in the examples below.

Example 1

Zein Nanoparticle Preparation

In a first aqueous phase, 13.5 mg of white zein was dissolved in a mixture of 3 mL of ethanol and 0.25 mL of water. The concentration of zein or solvent combination used was optimal; however, nanoparticles in the desired different size range can be produced by modifying the zein concentration or solvent composition. Dissolution of the zein was aided by the application of probe sonication for about 20 seconds. The resulting solution of the first aqueous phase was then added drop-wise into a 15 mL solution of citrate buffer, with a pH 7.4, and a combination of lecithin (0.45% w/v) and PLURONIC® F68 (0.9% w/v) under constant application of ultrasonic energy (1.39 kW/h, 37% amplitude) for 10 minutes with a pulse on time of 10 seconds and off time of 1 second. During the ultrasonic shearing process, the dispersion was kept in an ice bath to maintain the temperature at about 10° C. The dispersion was then placed on a magnetic stirrer at between 300 to 500 rpm, at room temperature (~23° C.), until the ethanol was completely evaporated. After complete evaporation of the ethanol, the nanoparticles were purified to remove any residual materials and/or surface active agents.

Purification was accomplished by repeated washing with deionized pH 7.4 citrate buffer and ultracentrifugation using centrifugal filters of MWt cut off of 5000 Da, at 3950 g for 50 minutes. To 4 mL of the resulting aqueous suspension (pH 7.4 citrate buffer) of zein nanoparticles was added 2% w/v trehalose as a cryoprotectant, and the nanoparticles were then kept at −80° C. to form to a solid cake. The material was then lyophilized at −47° C. and at 60 mTorr vacuum for 12 to 14 hours. The nanoparticles were then stored in a refrigerator at 10° C. in a dessicator. See FIG. 1. Additional methods for preparing zein nanoparticle are described by WO 2009/137112 (Perumal et al.), which is incorporated herein by reference.

In an alternative method, the ultrasonic shear of the second phase solution can be supplemented or replaced by high pressure homogenizer by passing the dispersion under high pressure through a narrow orifice for reducing the particle size. This is especially useful to produce nanoparticles in the smaller size range when a high concentration of zein is used. Also, high pressure homogenization can be used as a scale-up method for preparing zein nanoparticles. An example of this method is described in Example 2 below.

Example 2

Zein Nanoparticle Preparation Using a High Pressure Homogenizer

An amount of 0.65% w/v white zein was dissolved in a mixture of 6 mL of ethanol and 0.50 mL of water. The composition of the resulting solution of the first aqueous phase was altered to obtain a desired pH of about pH 6 to about pH 7. Dissolution of the zein was aided by the application of probe sonication for about 20 seconds. The resulting solution of the first aqueous phase was then added drop-wise into a 30 mL solution of citrate buffer, having a pH 7.4, and a combination of lecithin (0.45% w/v) and PLURONIC® F68 (0.9% w/v) under Constant application of ultrasonic energy (1.39 kW/h, 37% amplitude) for 2 minutes with a pulse on time of 10 seconds and off time of 1 second. During the ultrasonic shearing process, the dispersion was kept in an ice bath to maintain the temperature at about 10° C. The resulting coarse suspension was then passed through a high pressure homogenizer (NANO DEBEE®, USA) having an orifice size of between 0.1 and 0.25 mm for five minutes at 20,000 psi. During the high pressure homogenization process the temperature is maintained at approximately 10° C. by circulating water in the high pressure homogenizer using a chiller. Subsequently, the dispersion was kept on a magnetic stirrer at 300 to 500 r.p.m and at room temperature until the ethanol was completely evaporated. After complete evaporation, the nanoparticles were purified to remove any residual materials or surface active agents.

Purification was accomplished by repeated washing with pH 7.4 citrate buffer and ultracentrifugation using centrifugal filters of MWt cut off of 5000 Da, at 3950 g for 50 minutes. Four milliliters of aqueous suspension (pH 7.4 citrate buffer) of nanoparticles was mixed with 35 mg of 2% w/v trehalose, and was kept at −80° C. to form a solid cake. The cake was then lyophilized at −47° C. and 60 mTorr vacuum for 12 to 14 hours.

Figure 2:
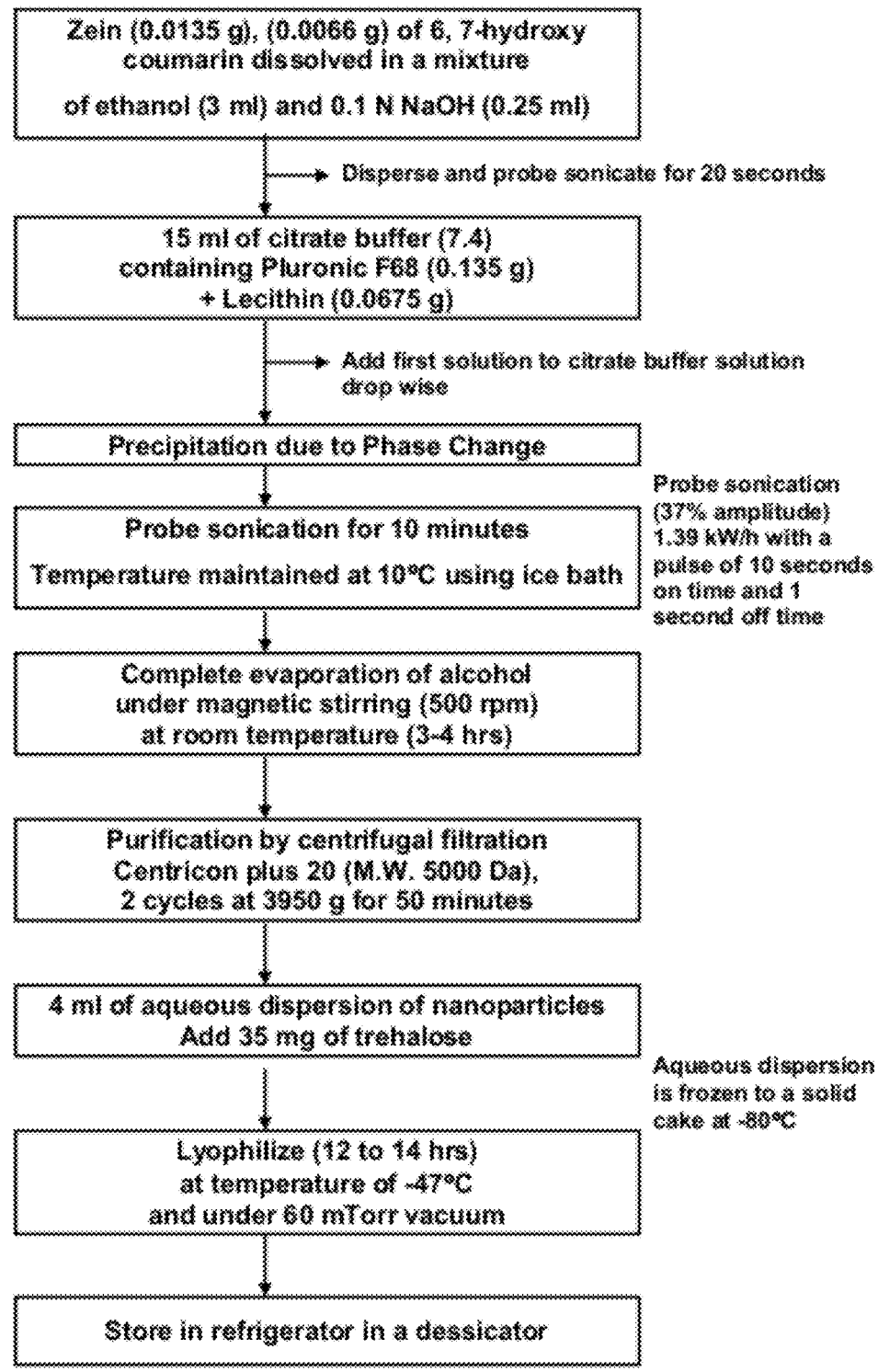
FIG. 2 illustrates by means of a flow chart the steps of forming 6,7 hydroxy coumarin loaded nanoparticles, according to one embodiment.

The methods described in Examples 1 and 2 can be adapted for the formation of nanoparticles where a selected molecule, such as a therapeutic drug, is encapsulated within a nanoparticle (e.g., see FIG. 2). The therapeutic drug can be, for example, coumarin, retinol, retinoic acid, or an ester thereof, as described herein.

Figure 3:
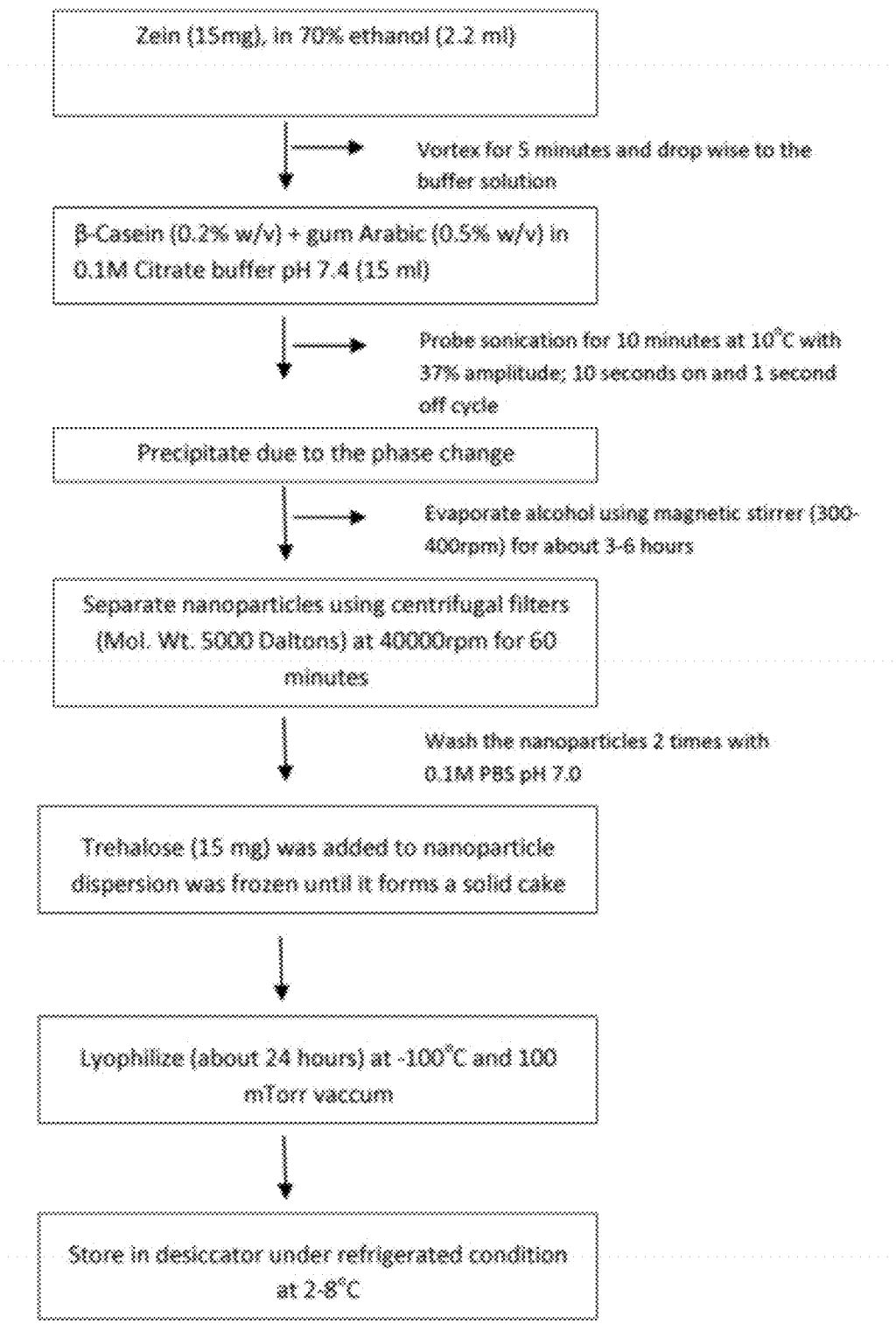
FIG. 3 illustrates steps for the preparation of zein nanoparticles stabilized by β-casein and gum Arabic using pH controlled nanoprecipitation, according to one embodiment.
Figure 4:
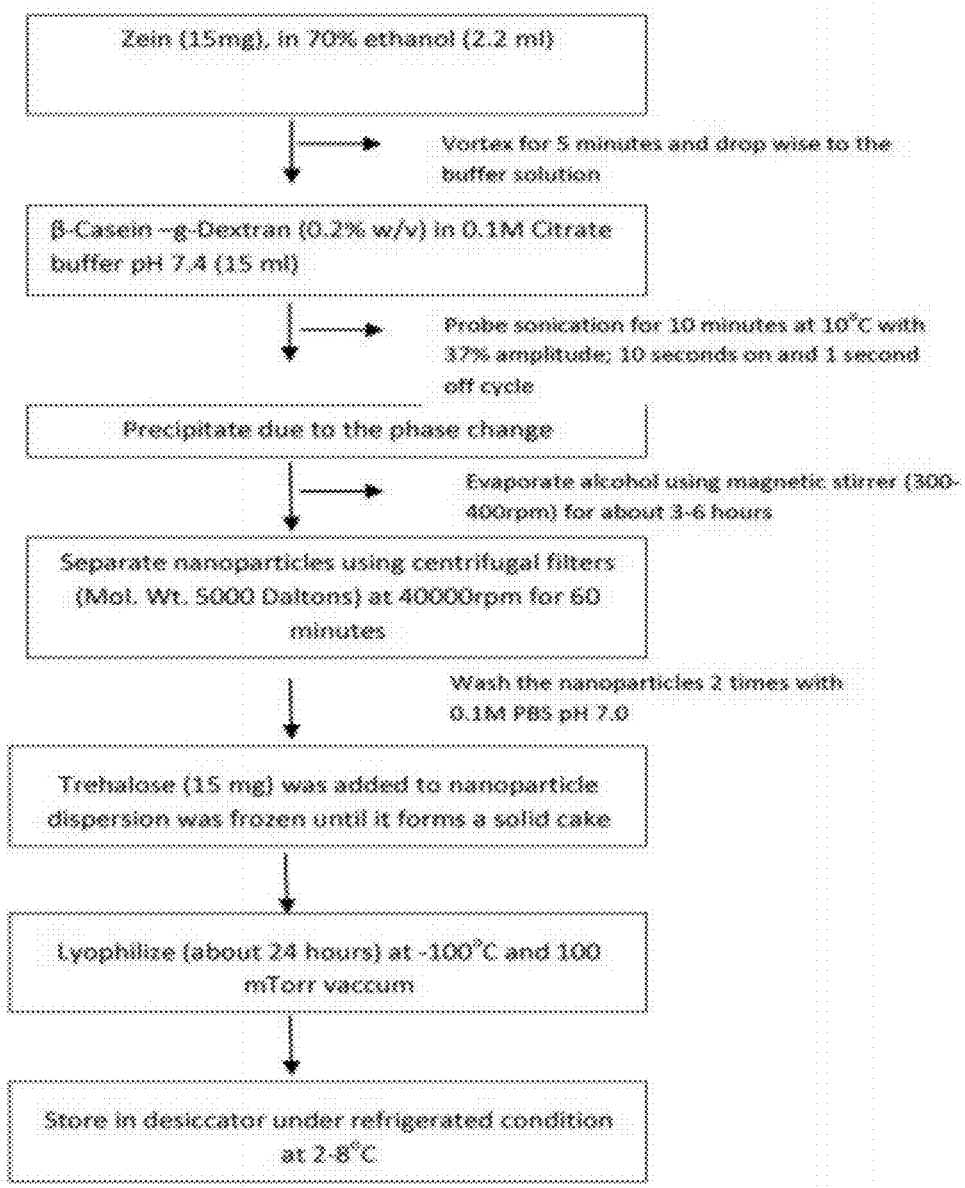
FIG. 4 illustrates the steps for the preparation of zein nanoparticles stabilized by β-casein grafted dextran, according to one embodiment.

Other variations on zein particle preparation can be seen in FIGS. 3 and 4. In the first method, zein particles are stabilized by β-casein and gum *Arabica* using pH controlled nanoprecipitation (see FIG. 3). In the second method, the reducing end (aldehydes) of dextran is conjugated to the α-amino acid casein. In brief, 40 mg of β-casein was mixed with 100 mg of dextran (11 kDa) in 20 ml of citrate buffer (pH 7.4) in a beaker. The beaker was covered with aluminum foil and stirred overnight at 70° C. The dextran-grafted β-casein was used as a stabilizer to prepare zein-dextran-casein nanoparticles as shown in FIG. 4.

In addition, nanoparticles may be prepared which include zein and casein (see Example 11, below).

Zein-Dextran nanoparticles. In a further variation, 50 mg of Zein and Dextran (11 kDa) were dissolved in 10 mL of Dimethyl sulfoxide (DMSO). The solution was stirred at room temperature for 24 hours. After stirring, the solution was introduced into the dialysis bag (molecular cutoff 10,000) and dialyzed against one liter of distilled water for 2 days during which the distilled water was exchanged every two hours for the first day to remove organic solvent completely. The resulting suspension was used for analysis or freeze-dried. This method relies on the interaction of proteins with polysaccharides.

TABLE 2.1

Characteristics of modified zein nanoparticles.

| Sample name | Average | PI |
| --- | --- | --- |
| Zein-casein-gum *Arabica* nanoparticles | 71.2 nm | 0.48 |

TABLE 2.1-continued

Characteristics of modified zein nanoparticles.

| Sample name | Average | PI |
|---|---|---|
| Zein-casein-dextran nanoparticles | 114 nm | 0.12 |
| Zein-dextran nanoparticles | 101 nm | 0.28 |

Example 3

Preparation of Agent Encapsulating Zein Nanoparticles

An example of a method for forming a molecule-encapsulated nanoparticle is as follows. White zein in the amount of 13.5 mg was dissolved in a mixture of 3 mL ethanol and 0.25 mL of 0.01N NaOH to adjust the pH between 6 and 7. To the solution was added 6.6 mg of 6,7 hydroxycoumarin and the mixture was subjected to probe sonication for 20 seconds to assure dissolution. In various embodiments, the 6,7-hydroxycoumarin can be replaced with about 0.03 mmol to about 0.05 mmol of a different agent described herein, such as retinol or a derivative thereof. In some embodiments, about 0.1% w/w to about 2% w/w, or about 0.3% w/w to about 1% w/w of an active agent, such as retinol, can be employed. The resulting solution was added drop-wise into 15 mL of citrate buffer (pH 7.4) containing 67.5 mg of lecithin and 135 mg of PLURONIC® F68 under constant ultrasonic energy at 1.39 kW/h and 37% amplitude for 10 minutes, with a pulse on-time of 10 seconds and an off-time of 1 second. During the sonication process, the solution was kept in an ice bath to maintain the temperature around 10° C. Subsequently, the dispersion was placed on a magnetic stirrer at 300 to 500 r.p.m and at room temperature until the ethanol was completely evaporated. Following complete evaporation of the alcohol, the nanoparticles were purified to remove any excess drug and/or surface active agents.

Purification was accomplished by repeated washing with pH 7.4 citrate buffer and ultracentrifugation using a centrifugal filter of MWt cut off of 5000 Da, at 3950 g for 50 minutes. Four milliliters of the aqueous suspension (pH 7.4 citrate buffer) of coumarin-loaded nanoparticles were added with 35 mg of trehalose and was kept at −80° C. to form a solid cake. The solid cake was then lyophilized at −47° C. and 60 mTorr vacuum for 12 to 14 hours.

Figure 5:
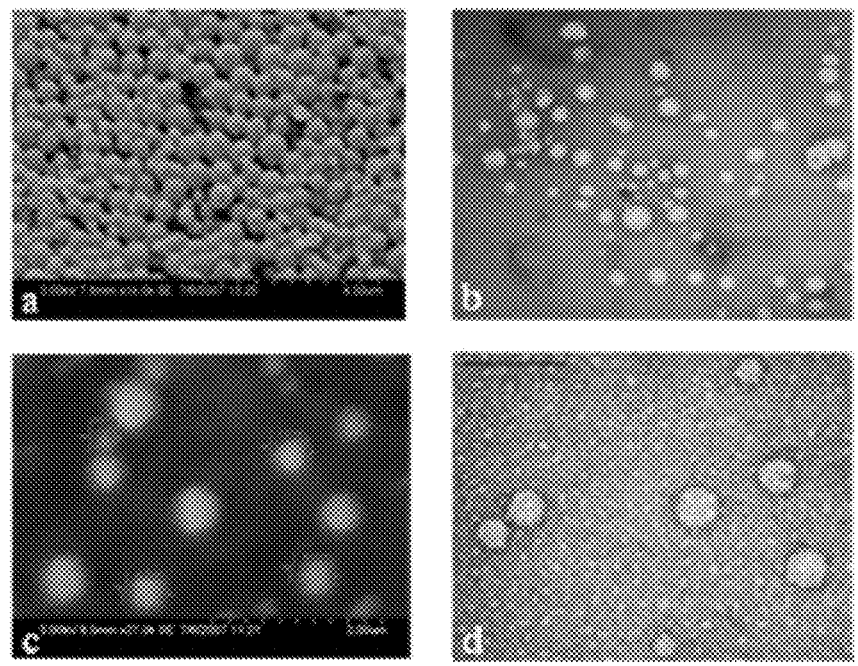
FIG. 5 depicts various electron microscopy microphotographs of zein nanoparticles.
Figure 6:
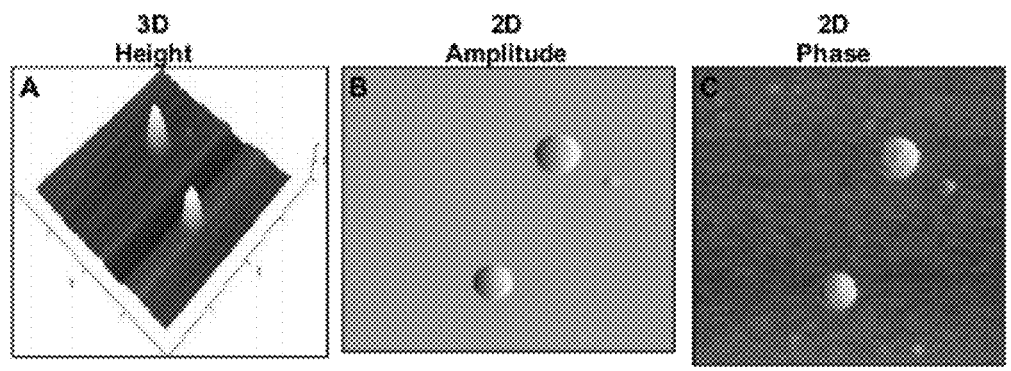
FIG. 6 depicts atomic force microscopy (AFM) images of blank zein nanoparticles in the tapping mode in air. Left to right are height (FIG. 6(a)), amplitude (FIG. 6(b)), and phase images (FIG. 6(c)) of a representative sample with z-scale of 14.19 nm, 22.2 V, and 45°, respectively. The scan size is a 1.14×1.14 gm. The average particle size among 50 particles measured in AFM is 185 nm.

It has been shown that white zein can be used as a suitable base protein. White zein gives reproducible nanoparticles in a desired narrow size range of approximately 100 nm to approximately 400 nm, while yellow zein gives larger particles with wider particle size distribution. This difference is illustrated in Table 3-1 and Table 3-2, below. Table 1 provides data of nanoparticles made from yellow zein by the method of Example 1 and Example 3, above. Both blank and coumarin-loaded nanoparticles are shown. It can be seen that the particle size of each is approximately 460 nm and 610 nm, respectively. By comparison, as shown in Table 2 below, blank and coumarin-loaded nanoparticles made from white zein by the method of Example 1 and Example 3 are smaller. FIGS. 5 and 6 show electron microscopic and atomic force image of the blank and coumarin-loaded zein nanoparticles.

TABLE 3-1

| Model compound | Particle Size (nm) | Polydispersity index (PDI) | Zeta Potential (mV) | Encapsulation Efficiency (%) |
|---|---|---|---|---|
| Blank zein nanoparticles | 460 ± 63 | 0.46 ± 0.06 | −10.28 ± 2 | Not applicable |
| 6,7-Hydroxy coumarin | 610 ± 123 | 0.62 ± 0.08 | −16.28 ± 3 | 98 ± 1.5 |

Each value is an average of three experiments with ±SD.

TABLE 3-2

| Model compound | Particle Size (nm) | Polydispersity index (PDI) | Zeta Potential (mV) | Encapsulation Efficiency (%) |
|---|---|---|---|---|
| Blank zein nanoparticles | 224 ± 20 | 0.31 ± 0.06 | −16 ± 3 | Not applicable |
| 6,7-Hydroxy coumarin | 266 ± 30 | 0.44 ± 0.08 | −11.34 ± 1.8 | 62 ± 17 |

Each value is an average of three experiments with ±SD.

The pigments in yellow zein appear to affect the solubility of zein and the formation of nanoparticles of the desired size distribution. It has been found to be particularly challenging to prepare particles using natural polymers, such as proteins, that are consistently within a desired small size range. However, the methods described herein produce nanoparticles consistently in the desired size range using a suitable grade of protein, such as white zein. Significantly, the methods described herein can produce, and have produced, nanoparticles with a diameter size as low as 80 nm to 100 nm. If part of the ultrasonic shear is replaced by high pressure homogenization, as described in Example 2, above, the resulting particle size of blank nanoparticles is also similar to the particle sizes shown in Table 2 above, namely having a particle size of approximately 220±15 nm and a PDI of 0.4±0.07.

The yield of nanoparticles produced by the nanoprecipitation methods that are in the desired size range has been found to be greater than approximately 60%. The methods are significant in that the particles produced have diameters that primarily measure in a range of less than approximately 400 nm, and typically with a relatively narrow diameter size distribution of approximately 100 nm to approximately 300 nm, to avoid an immunogenic reaction when administered into the body. Advantageously, zein nanoparticles in the diameter size range of approximately 100 to approximately 400 nm, such as are produced by the methods described herein, are not taken up by phagocytic cells, while larger particles of a diameter size greater than approximately 400 nm are rapidly taken up by phagocytic cells when tested in vitro using porcine blood. This indicates that nanoparticle phagocytosis is avoided by controlling the particle diameter size of zein nanoparticles in the smaller size range.

Immunogenicity studies in mice showed that zein nanoparticles of about 100 to about 400 nm in diameter are non-immunogenic, while zein nanoparticles having a diameter greater than about 400 nm produced a significant immune response (anti-zein antibodies were two- to four fold higher compared to saline control). These results show that preparing and using nanoparticles having diameters less than about 400 nm is important to avoid any significant immunogenicity caused by the hydrophobic proteins of the particles.

The ability to control size of the nanoparticles is achieved in part by controlling the pH of the solution in the second aqueous phase of the method. The data in Table 3-3 below illustrates that smaller sizes of nanoparticles, with a low PDI, are achieved at a pH of between about 6.8 and about 7.4.

TABLE 3-3

| pH of the aqueous phase | Particle Size (nm) | Polydispersity index |
|---|---|---|
| 1.5 | 362 ± 24 | 0.392 |
| 3 | 291 ± 15 | 0.45 |
| 6.8 | 208 ± 10 | 0.289 |
| 7.4 | 232 ± 7 | 0.260 |
| 10 | 256 ± 20 | 0.317 |
| 12 | 368 ± 10 | 0.438 |

Each value is an average of three experiments with ±SD

A further important factor in controlling the size of nanoparticle formation is the combination of surfactant and phospholipids used to stabilize the nanoparticles and prevent particle aggregation. A combination of a poloxamer and lecithin, such as in a 2:1 ratio (e.g., 0.9:0.45%, w/w), produces nanoparticles in the desired size range. If either the surfactant or the phospholipid is used alone, larger particles are obtained, as indicated by the data of Table 3-4, below.

TABLE 3-4

| Surfactant (% w/v) | Particle size (nm) | PDI |
|---|---|---|
| PLURONIC ® (0.9) | 516 ± 75 | 0.57 ± 0.07 |
| Lecithin (0.9) | 335 ± 45 | 0.52 ± 0.05 |
| PLURONIC ® (0.9) and Lecithin (0.45) | 274 ± 36 | 0.46 ± 0.02 |

Each value is an average of three experiments with ±SD. 10 * Lyophilization resulted in a sticky powder.

Figure 7:
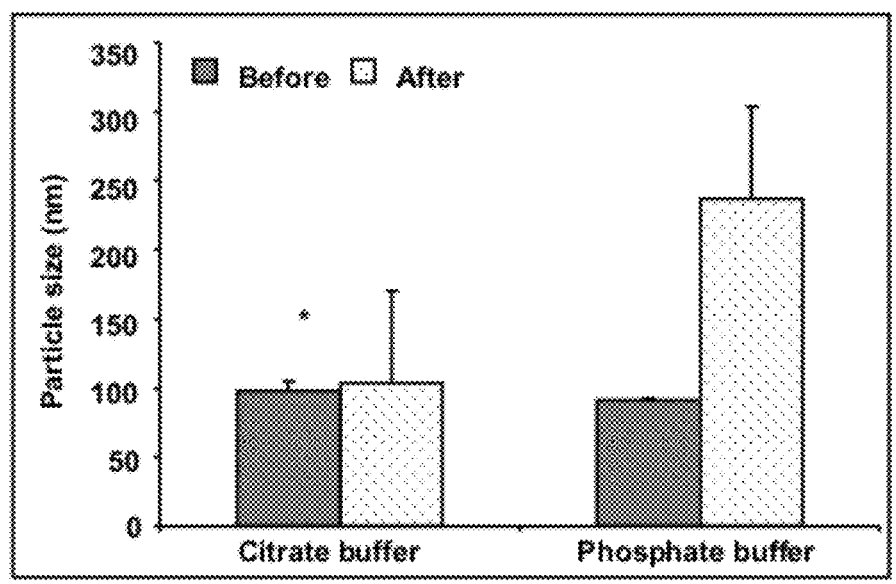
FIG. 7 is a graph illustrating the influence of buffer type on the particle size of coumarin-loaded zein nanoparticles according to one embodiment, before and after lyophilization. Use of citrate buffer in the precipitation method produced consistently smaller sizes of nanoparticles following lyophilization as compared with the use of phosphate buffer. (* $p<0.05$). Each point on the graph represents the mean±SD (n=3). Citrate buffer was composed of citric acid (0.0153 g/L) and sodium citrate (2.91 g/L) in deionized water. Phosphate buffer was composed of dibasic sodium phosphate (1.44 g/L), monobasic potassium phosphate (0.25 g/L) and sodium chloride (10 g/L) in deionized water. Both buffers were used to maintain the second aqueous phase at pH 7.4.

The choice of buffering agent for the second aqueous phase is not only important to maintaining the optimum pH during nanoparticle formation, but is also important for subsequent lyophilization. For example, if no buffering agent is used in the second aqueous phase solution, or if 0.1N HCl is used to adjust the pH, the resulting nanoparticles are larger in size, with a wider size range or PDI. As shown in FIG. 7, the use of citrate buffer provided the smallest particle size (109±12 nm). The use of other buffering agents, particularly phosphate, results in the particle size of zein nanoparticles being increased by two to three times after lyophilization.

The graph of FIG. 7 illustrates that zein nanoparticles prepared by the method using phosphate as the buffering agent in the solution from the second aqueous phase and obtained after lyophilization produced much larger particles as compared to nanoparticles prepared using citrate buffer as the buffering agent in the second aqueous phase. The particle size increase in phosphate buffer could be due to the crystallization and precipitation of buffer at the freeze-drying temperatures caused by the pH drop (Shalaev et al., Pharm Res 19 (2002) 195-201). This problem is solved using citrate buffer, which effectively resists the changes in pH during freeze-drying temperatures. The amino groups in zein can be cross-linked by citric acid, which can also stabilize the zein nanoparticles (Reddy et al., Biotechnol. Prog. 25 (2009) 139-146).

It is notable that zein is a biodegradable protein and is also more biocompatible than synthetic polymers. Zein is listed as a GRAS (Generally Regarded As Safe) polymer by FDA standards (Wheat gluten, corn gluten and zein film: affirmation of GRAS status, Fed Register 50 (1985) 8997-8999). The methods described herein are, therefore, suitable for preparing zein nanoparticles with encapsulated cargo molecules or drugs of different physiochemical properties. Table 3-5 below illustrates various molecules that may be encapsulated by nanoparticles using the methods described herein, according to various embodiments. The number or type of molecules that may be used in the nanoparticle encapsulation are not limited to those noted herein.

TABLE 3-5

| Model compound | Particle Size (nm) | Zeta potential | Encapsulation efficiency (%) |
|---|---|---|---|
| 6,7-hydroxy coumarin | 173 ± 20 | −16 ± 3 | 68 ± 6 |
| Doxorubicin | 171 ± 45 | −21 ± 2 | 61 ± 16 |
| Dextran FITC (4000 Da) | 89 ± 12 | −15 ± 2 | 79 ± 8 |
| pDNA (GFP) | 185 ± 12 | −17 ± 0.4 | 86.2 ± 3 |

Each value is a mean of three experiments with ±SD.

Figure 8:
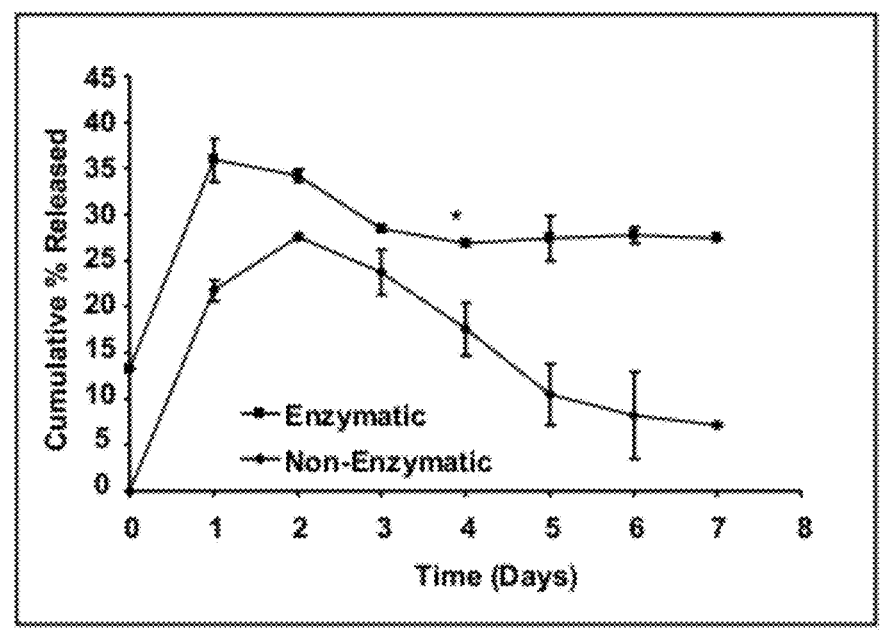
FIG. 8 illustrates an in vitro release profile of 6,7-hydroxy coumarin-loaded zein nanoparticles in phosphate buffered saline (pH 7.4). Coumarin-loaded zein nanoparticles (10 mg/mL) prepared by the methods described in Example 2 were placed in a dialysis membrane (SPECTRAPOR™, M.wt. 5000 Da) and incubated in phosphate buffered saline (pH 7.4) in the absence (non-enzymatic) or presence (enzymatic) of trypsin (10 mg/mL). Ethanol (20% v/v) was added to the media to maintain sink conditions, and sodium azide (0.005% w/v) was used as an anti-microbial agent. The solution was maintained at 37° C. in a horizontal shaker waterbath at 50 rpm. An aliquot (1 mL) of the dialysate was removed at different time points for 7 days and replaced with fresh media to maintain the sink conditions. Dialysate was analyzed for coumarin released from the zein nanoparticles using spectrofluorimetry ($\lambda_{max}$=490 nm; $\lambda_{em}$=520 nm). Each data point is a mean of three experiments (±SD). Enzymatic release was higher compared to non-enzymatic release at all time points ($p<0.05$).

Thus nanoparticles formed with various cargo molecules, such as 6,7-hydroxycoumarin, have been successfully prepared with control over particle size and immunogenicity. An example of the preparation of 6,7-hydroxy coumarin-loaded particles is described in above and its preparation is illustrated in FIG. 8, according to one embodiment.

Zein nanoparticles prepared as described herein provide a beneficial and/or advantageous sustained release of the encapsulated molecule or drug due in part to the water insolubility of zein nanoparticles that enable the particles to sustain the drug release over a period of time. For example, FIG. 8 depicts the in vitro release profiles for coumarin-loaded nanoparticles made in accordance with the methods described in Example 2 above. The data indicates that in vitro, there is a sustained release of the drug over a period of up to seven days, with a higher release rate being observed in the presence of enzymes. The data shows that the zein nanoparticle release is mediated by slow diffusion of drug out of the nanoparticle and slow enzymatic breakdown of zein nanoparticles. Other examples of encapsulated drugs showed a mixed order with an initial burst followed by a sustained release after approximately 24 hours.

The drug release profiles for various encapsulated molecules indicate that zein nanoparticles can be used as a versatile and safe drug delivery vehicle by parenteral and non parenteral routes of administration, including oral, buccal, transdermal, nasal, pulmonary and ocular routes of delivery. Many other molecules, particles and drugs may be encapsulated as well, including but not limited to, pharmaceutical and cosmetic substances (e.g., vitamin A (retinol), Vitamin C and its derivatives such as ascorbyl palmitate, Vitamin E and its derivatives such as tocopheryl acetate, Coenzyme Q10, minoxidil, green tree extract, aloe vera, hydroquinone, hyaluronic acid, sodium hyaluronate, bisabolol, glycolic acid, lactic acid, beta hydroxybutanoic acid, salicylic acid, 10-hydroxydecanoic acid, ferulic acid, pantethenol, biotic, arbutin, quercetin, hesperidin, and the like, or a combination thereof) for therapeutic, diagnostic and aesthetic applications or therapies. Further, due to the relatively smaller size of the nanoparticles formed by the methods described herein, molecule-loaded (e.g., drug-loaded) zein nanoparticles can circulate in the body for prolonged periods without being recognized and eliminated by phagocytic cells.

Figure 9:
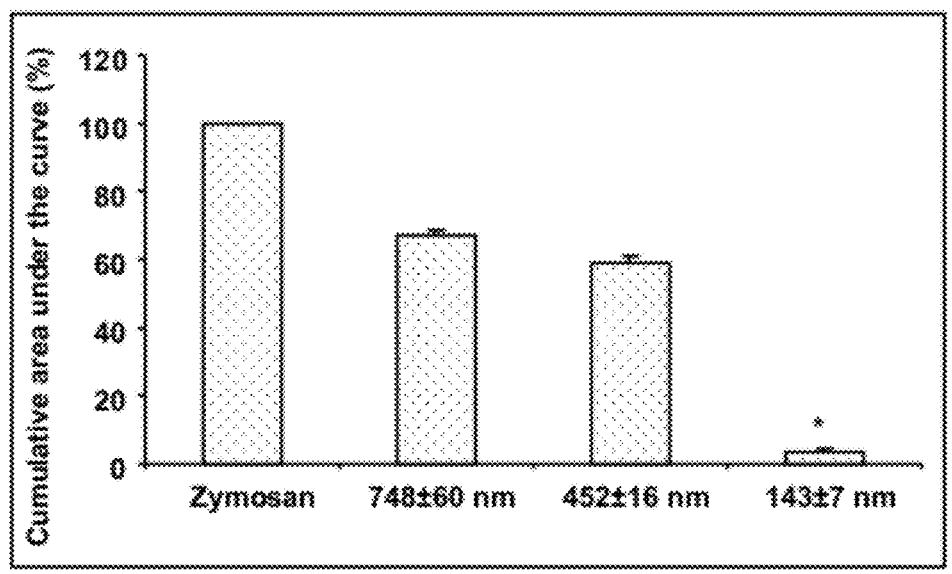
FIG. 9 illustrates the influence of particle size on uptake of zein nanoparticles by porcine polymorpho-nuclear cells. The figure shows the percent area under the curve for luminal chemiluminescence (over 90 minutes) in the presence of zein particles and positive control zymosan. Each experiment is an average of four experiments (±SEM). Uptake is significantly lower in smaller particles ($p<0.05$) compared to other groups.
Figure 10:
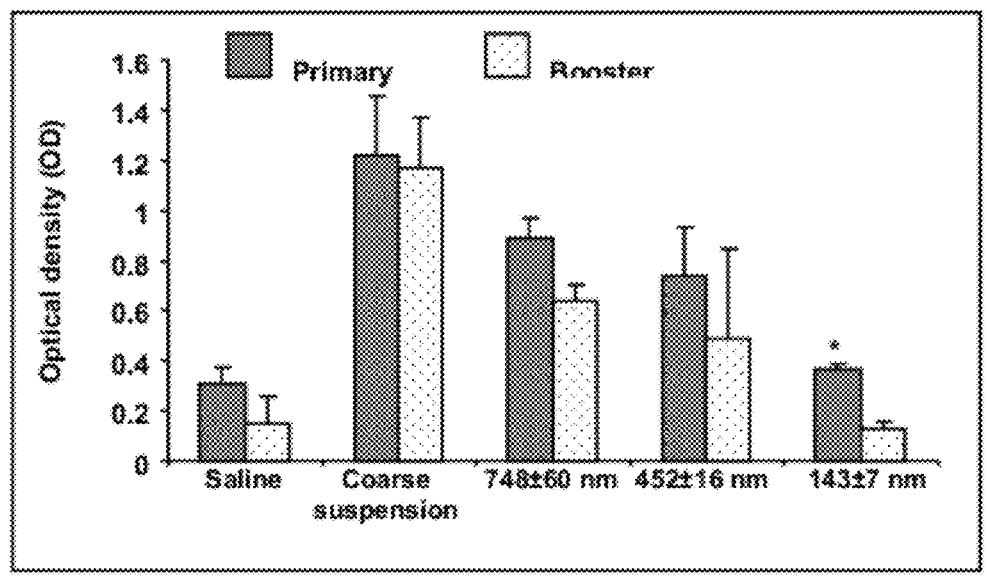
FIG. 10 illustrates anti-zein antibodies (optical density) measured after the third and fifth weeks of primary and booster subcutaneous injections of zein particles, respectively. Each value is represented as mean±SEM (n=4). Both the primary and booster titres were statistically not significant ($p>0.05$) compared to the saline group. A coarse zein suspension or zein particles in saline (equivalent to 100 μg/50 μL) were injected subcutaneously in female BALB/C mice. Blood was withdrawn from the orbital plexus and the anti-zein antibody levels in the diluted serum (1/16) were measured using a mouse ELISA kit.

The data of FIG. 9 illustrate that zein nanoparticles in the size range of 100-400 nm are not taken up by the blood phagocytic cells, while larger particles in the size of >400 nm are rapidly taken up by phagocytic cells when tested in vitro using porcine blood. Thus, it can be shown that phagocytic uptake is avoided by controlling the particle size of zein nanoparticles in the smaller size range. Immunogenicity studies in mice showed that zein nanoparticles in the size range of 100 nm to 400 nm are non-immunogenic. On the other hand, zein nanoparticles having a size>400 nm produced a significant immune response (two- to four-fold) compared to the control, as shown in FIG. 10.

Figure 11:
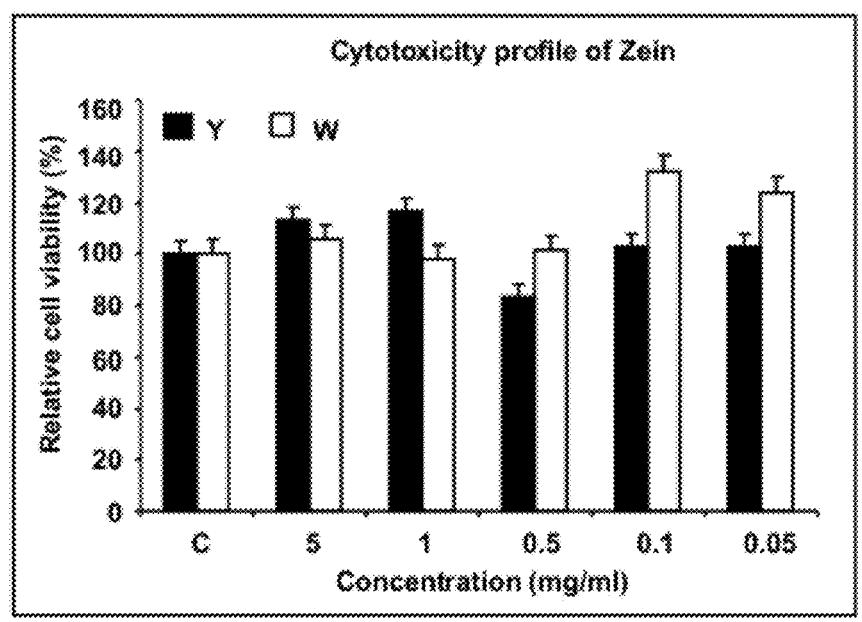
FIG. 11 is a graph illustrating the influence of yellow zein (Y) and white zein (W) on cell viability of porcine intestinal epithelial cells (IPEC-J2 cells) (at 20,000 cells/well) expressed as the relative activities of mitochondrial dehydrogenase after four hours of treatment using a dimethylthiazol-2-yl-2,5-diphenyltetrazolium bromide (MTT) assay. The plate without any treatment was used as a control and was considered to be 100% viable. Zein powder was dissolved in 55% v/v ethanol and subsequent dilutions were made from 5 mg/mL stock in serum-free media. At all concentrations, both yellow and white zein do not differ significantly from the control with no treatment (* $p<0.05$). Each data point is an average of three experiments±SEM.

The cytotoxic effects of the zein used for making the nanoparticles were investigated in cell proliferation studies using porcine intestinal epithelial cells (IPEC-J2). The results of an exemplary cytotoxicity studies is shown in FIG. 11. No significant degree of cytotoxicity was observed between white zein and yellow zein, as compared to control treatment with buffer at any concentration.

Example 4

Crosslinked Nanoparticles

Figure 12:
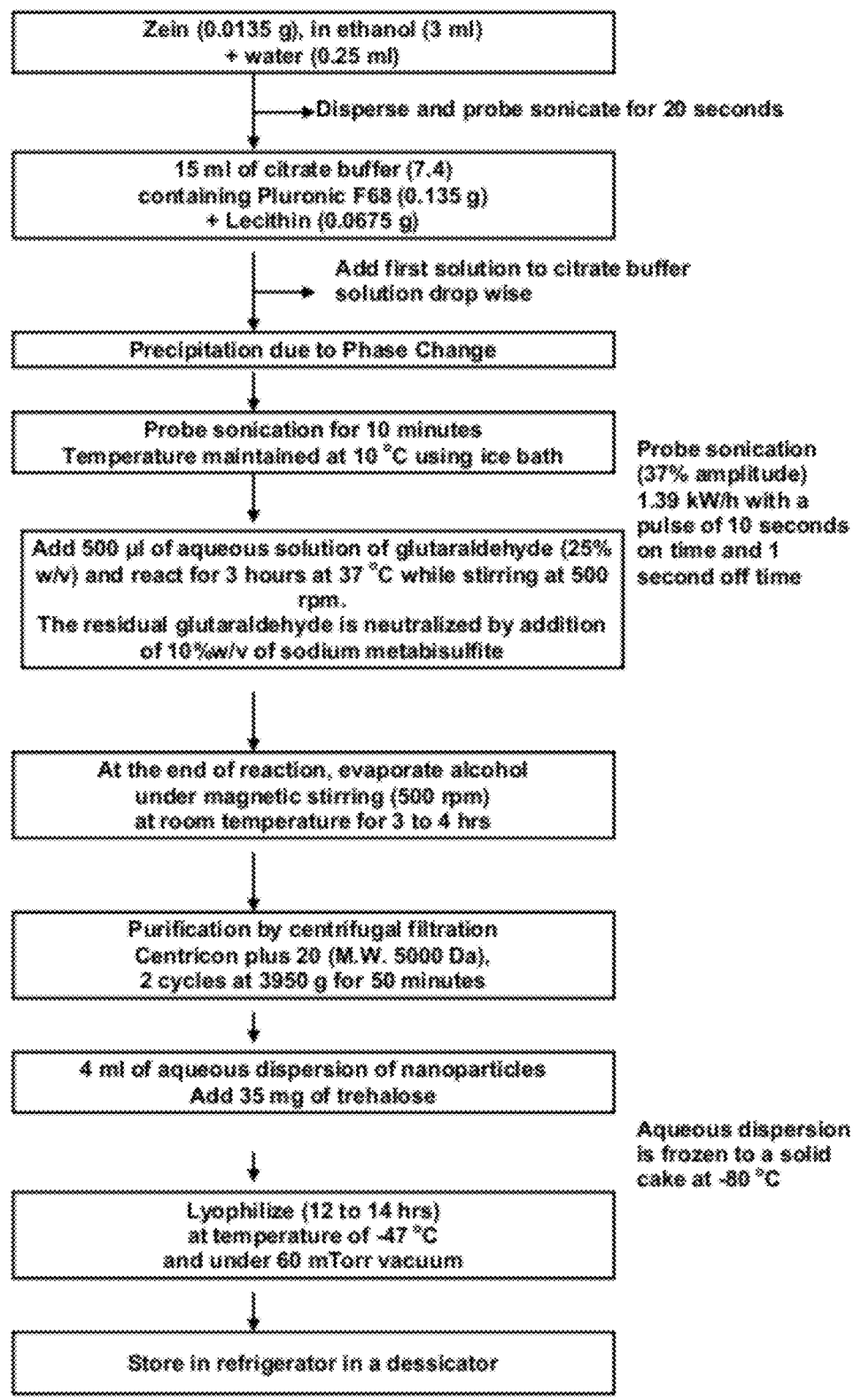
FIG. 12 illustrates, by means of a flow chart, a method for preparing cross-linked blank zein nanoparticles, according to one embodiment.

The enzymatic stability of the nanoparticles prepared as described herein can be further enhanced by cross-linking FIG. 12 illustrates the general method for preparation of cross linked blank zein nanoparticles using glutaraldehyde as the cross-linking agent. A specific example of such preparation is as follows.

Blank zein nanoparticles were prepared using the nanoprecipitation method described above. A cross linking agent was added following probe sonication of the second aqueous phase. Nanoparticles were further incubated for 24 hours. At the end of incubation time, the nanoparticles were purified using centrifugal filtration and were then lyophilized. White zein (0.0135 g) was dissolved in a mixture of 3 mL of ethanol and 0.25 mL of water. The first phase solution was then added drop-wise into 15 mL of citrate buffer having a pH 7.4 and containing a combination of 0.45% w/v lecithin and PLURONIC® F68 (0.9% w/v) under constant application of ultrasonic energy at 1.39 kW/h and 37% amplitude for 10 minutes with a pulse on-time of 10 seconds and off-time of 1 second. During the sonication process, the solution was kept in an ice bath to maintain the temperature at about 10° C. To the solution was added 0.5 mL of glutaraldehyde of 25% w/v and the solution was incubated for 3 to 24 hours at 37° C. while stirring at 300 to 500 rpm. The residual glutaraldehyde was neutralized with 10% w/v metabisulfite. Subsequently, the dispersion was placed on a magnetic stirrer at 300 to 500 rpm and at room temperature until the ethanol was completely evaporated. After complete evaporation of the alcohol, the nanoparticles were purified to remove the residual material.

Purification was accomplished by repeated washing with pH 7.4 citrate buffer and ultracentrifugation, using centrifugal filter of MWt cut off of 5000 Da, at 3950 g for 50 minutes. To the aqueous suspension of nanoparticles was added 35 mg of trehalose and the solution was kept at −80° C. to form a solid cake. The material was then lyophilized at −47° C. and 60 mTorr vacuum for 12 to 14 hours. Notably, for other cross-linking agents such as EDC/NHS and genipin, when used in the method of FIG. 12, the reaction time can vary from 24 to 72 hours.

Figure 13:
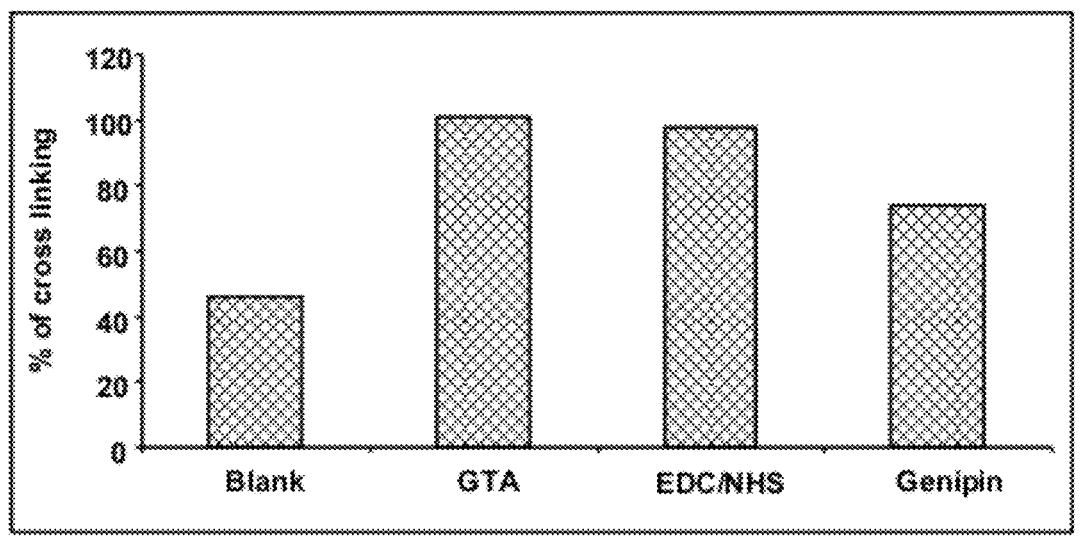
FIG. 13 is a graph demonstrating the extent of cross-linking of zein nanoparticles as a function of cross-linking agent for 24 hours. The extent of cross-linking was determined using a TNBS assay. The cross-linking agents used were: Glutaraldehyde (GTA) (500 μL of a stock solution of 25% w/v), 1-ethyl-3-[3-dimethylaminopropyl]carbodiimide (EDC) (0.6% w/v), and N-hydroxyl succinimide (NHS) (0.6% w/v). The concentration of genipin used was 0.05% w/v. "Blank" represents zein nanoparticles without any cross-linking agent. Data is a mean of two experiments.

The surface amino groups in zein are involved in cross-linking Trinitro benzene sulfonic acid (TNBS) was used to estimate the free amino groups in zein before and after cross-linking. A standard curve was generated with increasing concentration of non-cross linked and cross-linked zein versus absorbance at 440 nm wavelength. Cross linking efficiency was calculated using the formula:

% of Cross linking efficiency=$[a-b/a] \times 100$ where a=the slope of the concentration of non-cross linked zein versus absorbance, and b=the slope of the concentration of cross-linked zein versus absorbance. The concentration range of zein used for constructing the standard curve is 0.357 mg/mL to 12 mg/mL, and correlation coefficient is 0.9994. The extent of cross-linking in zein nanoparticles using different cross-linking agents is shown in FIG. 13. The cross-linking efficiency varied from approximately 70% to approximately 100%. The extent of cross-linking can be varied by changing the reaction time to range from approximately 3 hours to 3 days depending on the cross-linking agent. The cross-linking agent shown here are only examples and the methods described herein are not limited to the use of just the disclosed cross-linking agents. Other cross-linking agents can be used such as polycarboxylic acids (citric acid or 1,2,3,4-butanetetracarboxylic acid).

Example 5

Crosslinked Rhodamine-Encapsulating Nanoparticles

Figure 14:
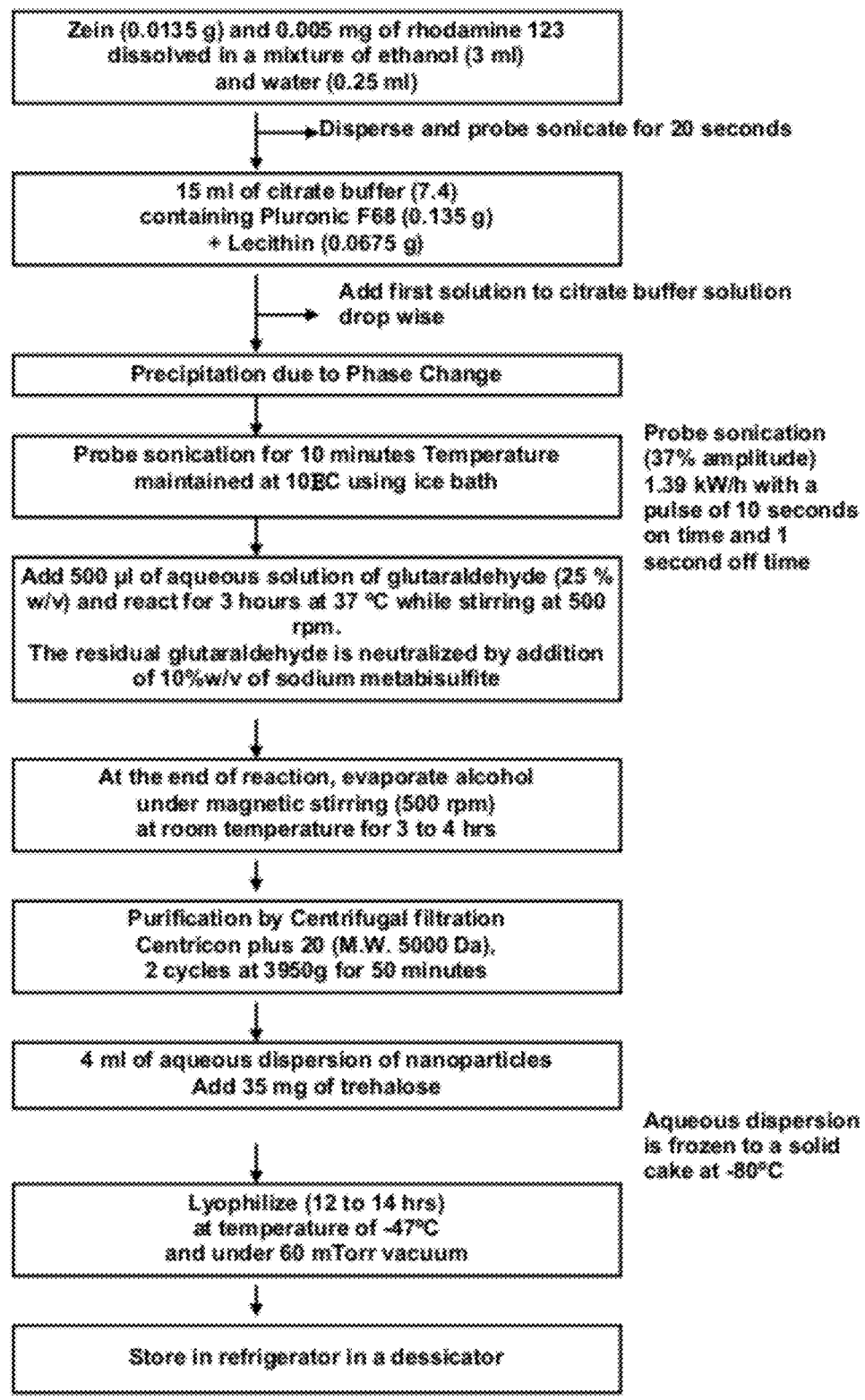
FIG. 14 illustrates, by means of a flow chart, a method for preparing rhodamine-123-loaded cross-linked zein nanoparticles, according to one embodiment.

The example above illustrated the preparation of blank zein nanoparticles, cross-linking can also be carried out in the formation of nanoparticles containing specific molecules. A specific example of preparing rhodamine, a water soluble dye, in a nanoparticle is as follows (see FIG. 14). This method can be used for encapsulating other compounds, such as retinol and related compounds described herein.

Rhodamine 123 has a molecular weight of 380.82 and a Log P of 1.2. It is a green fluorescent dye that is slightly soluble in water and completely soluble in methanol, dimethyl sulfoxide and dimethylformamide.

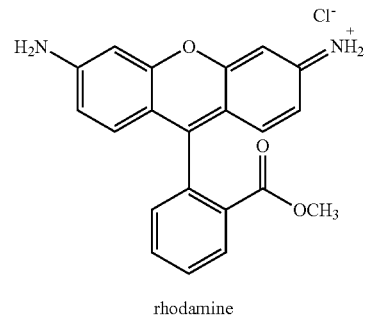 [SMILES: [Cl-] ; COC(=O)c1ccccc1-c1c2ccc(=N)cc-2oc2cc(N)ccc12]

rhodamine

White zein (0.0135 g) was dissolved in a mixture of 3 mL of ethanol and 0.25 mL of water (0.25 mL). To the first aqueous solution was added 0.0005 g of rhodamine-123. The resulting solution was added drop-wise into 15 mL of citrate buffer having a pH 7.4 and containing a combination of 0.0675 g of lecithin and (0.135 g) of PLURONIC® F68 under constant application of ultrasonic energy at 1.39 kW/h and 37% amplitude for 10 minutes with a pulse on time of 10 seconds and off-time of 1 second. During the sonication process, the solution was kept in an ice bath to maintain the temperature at about 10° C. Then 0.5 mL of glutaraldehyde (25% w/v) was added and incubated for 3 hours at 37° C. while stirring at 300 to 500 rpm. The residual cross-linking agent was neutralized with 10% w/v sodium metabisulfite. Subsequently, the dispersion was placed on a magnetic stirrer at 300 to 500 rpm at room temperature until the ethanol was completely evaporated. After complete evaporation of the alcohol, the nanoparticles were purified ultracentrifugation.

Purification was accomplished by repeated washing with pH 7.4 citrate buffer and ultracentrifugation using centrifugal filter of MWt cut off of 5000 Da, at 3950 g for 50 minutes. To the aqueous suspension (pH 7.4 citrate buffer) of rhodamine-loaded nanoparticles was added 35 mg of trehalose and the solution was kept at −80° C. to form a solid cake, which was then lyophilized at −47° C. and 60 mTorr vacuum for 12 to 14 hours.

The particle size, polydispersity index and zeta potential of non-cross linked and cross-linked (using glutaraldehyde as a cross-linking agent) rhodamine particles are shown in Table 5-1.

TABLE 5-1

| Sample No. | Rhodamine (% w/w) | Particle size (nm) | PDI | Zeta potential (mV) | Encapsulation efficiency (%) |
|---|---|---|---|---|---|
| Non Cross Linked | | | | | |
| 1. | 0.0296 | 283.7 ± 8.59 | 0.237 ± 0.098 | −8.93 ± 2.1 | 25.2 ± 3.26 |
| 2. | 0.0370 | 243 ± 12 | 0.37 ± 0.007 | −9.16 ± 2.8 | 22.40 ± 5.0 |
| Cross Linked | | | | | |
| 1. | 0.0370 | 356 ± 8.9 | 0.198 ± 0.0.03 | −11.41 ± 3.13 | 6.23 ± 7.0 |

Each value is a mean of three experiments (±SD).

Figure 15:
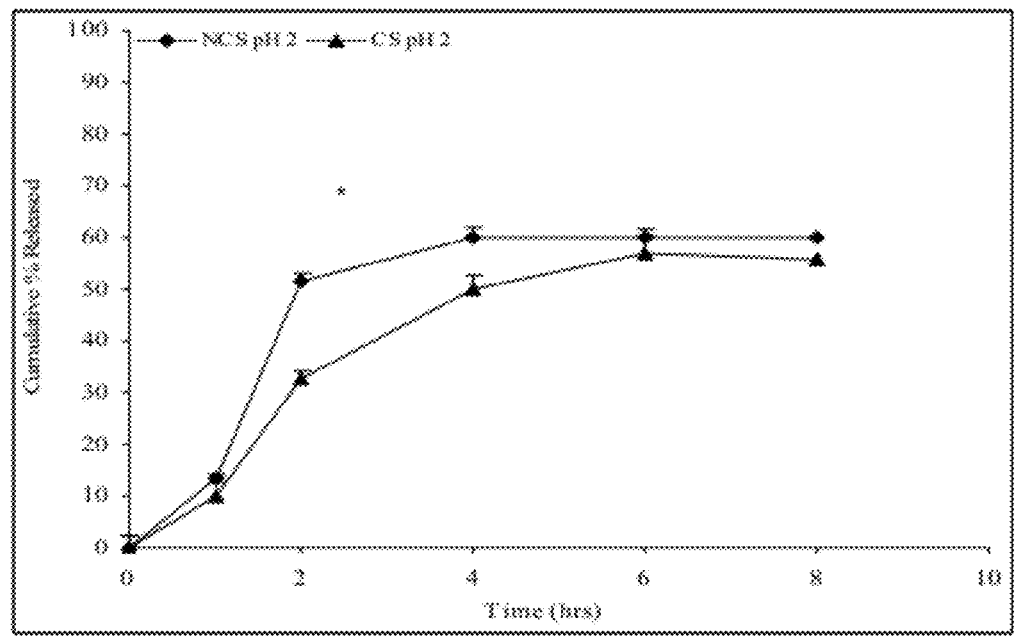
FIG. 15 illustrates the in vitro release profile of rhodamine-123 from zein nanoparticles in citrate buffer pH 2. Results represent mean±SEM (n=4). NCS=non-cross linked particles; CS=cross linked particles. Rhodamine release from cross-linked nanoparticles was significantly ($p>0.05$) lower than the non cross-linked nanoparticles. Rhodamine-loaded zein nanoparticles (20 mg) prepared by the methods described herein were placed in a dialysis membrane (SPECTRAPOR™, M.wt. 10,000 Da) and incubated in 10 mL of citrate buffer (pH 2). The solution was maintained at 37° C. in a horizontal shaker water bath at 100 rpm. An aliquot (1 mL) of the dialysate was removed at different time points over 48 hours and replaced with fresh media to maintain the sink conditions. Dialysate was analyzed for rhodamine release from the zein nanoparticles using spectrofluorimetry ($\lambda_{max}$=485 nm; $\lambda_{em}$=530 nm) (* indicates that the difference is significant at $p<0.05$).
Figure 16:
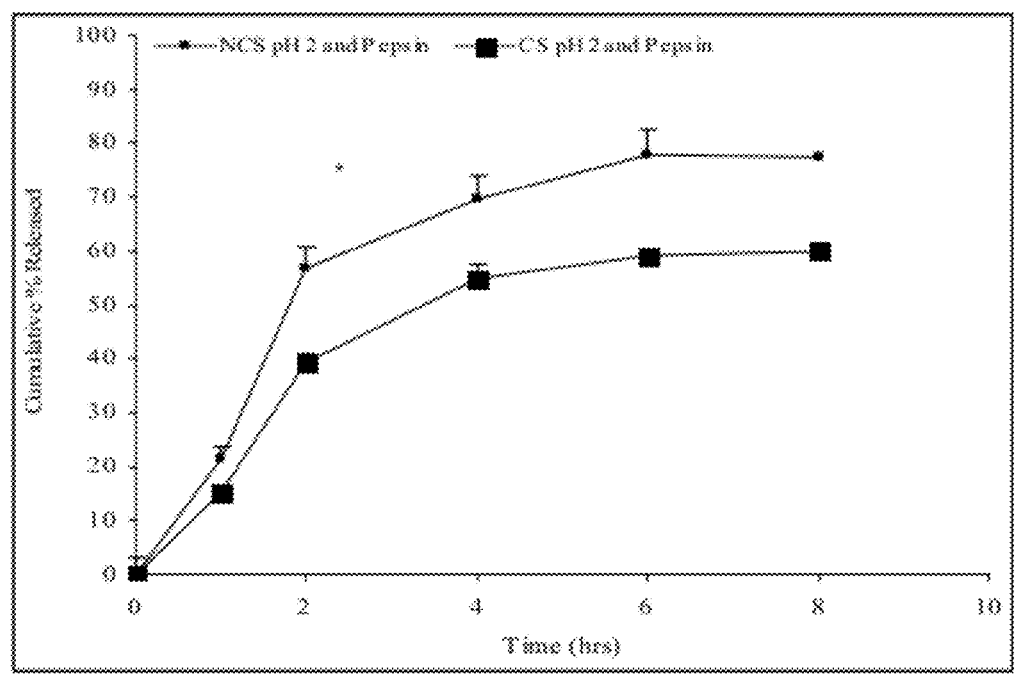
FIG. 16 illustrates the in vitro release profile of rhodamine-123 from zein nanoparticles in the presence of pepsin at pH 2. Results represent mean±SEM (n=4). NCS=non-cross linked particles; CS=cross linked particles. The drug release from cross-linked nanoparticles was significantly (p>0.05) lower than the non cross-linked nanoparticles. Rhodamine-123-loaded zein nanoparticles (20 mg) prepared by the methods described herein were placed in a dialysis membrane (SPECTRAPOR™, M.wt. 10,000 Da) and incubated in 10 mL of citrate buffer (pH 2) containing 3.2 mg/mL of pepsin. The solution was maintained at 37° C. in a horizontal shaker water bath at 100 rpm. An aliquot (1 mL) of the dialysate was removed at different time points over 48 hours and replaced with fresh media to maintain the sink conditions. Dialysate was analyzed for rhodamin-123 released from the zein nanoparticles using spectrofluorimetry ($\lambda_{max}$=20 485 nm; $\lambda_{em}$=530 nm) (* indicates that the difference is significant at p<0.05).

The in vitro drug release at pH 2 is slower when the zein nanoparticles were cross-linked (FIG. 15), and similarly the enzymatic release was also slower (FIG. 16). The cross-linking of the free amino groups on the surface of zein nanoparticles reduced the particle size, reduced the access of solvent, and slowed the enzymatic degradation of the nanoparticles. The cross-linking also significantly reduced the burst effect. Thus cross-linking can further stabilize the nanoparticles and sustain cargo release from the nanoparticles.

Example 6

PEGylated Zein Nanoparticles

The therapeutic activity and efficacy of the nanoparticles produced by the methods described herein can be further enhanced by attaching polyethylene glycol (PEG) to the nanoparticles. Among the added benefits of PEGylation is an increase in the circulation half-life of the nanoparticles. An additional advantage of PEG is that it can serve as a spacer to link the targeting ligands, drugs, and imaging agents to zein nanoparticles, if direct conjugation is not readily synthetically feasible.

Figure 17:
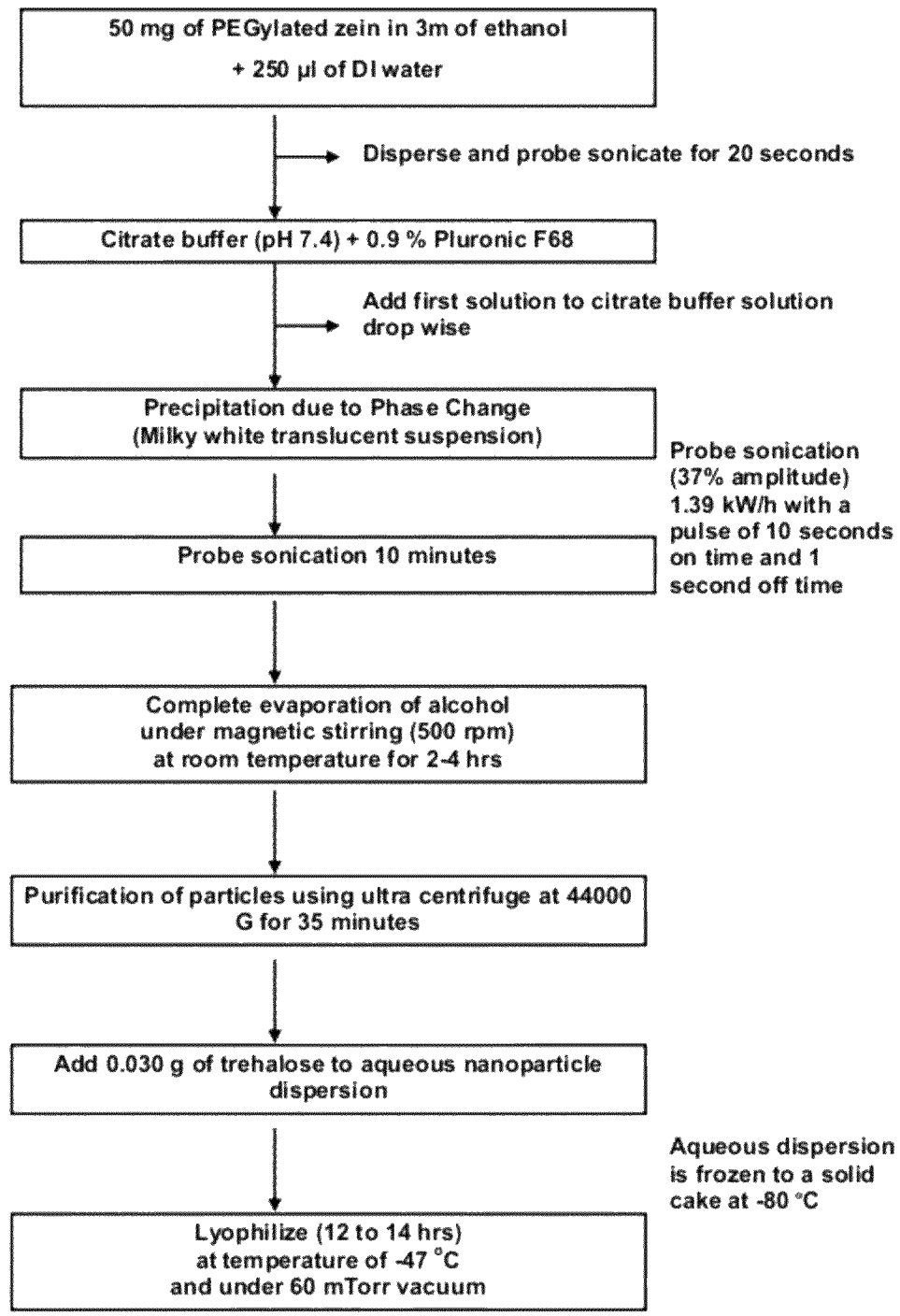
FIG. 17 illustrates in a flow chart the general methods for preparation of blank PEGylated zein nanoparticles, according to one embodiment.

FIG. 17 illustrates a method of preparing PEGylated zein nanoparticles in accordance with another embodiment. An advantage of PEGylated zein for making nanoparticles is that it can be made using only a surfactant, such as PLURONIC® F68, as opposed to the use of a combination of a surfactant and phospholipids for non-PEGylated zein. A specific method of forming PEGylated zein nanoparticles is as follows.

PEGylated zein was produced by adding 0.1 g of methoxy PEG-succinimidyl succinate (Mwt 5000 Da) to 0.1 g of white zein in 5 mL of 90% ethanol. The mixture was incubated for 3-24 hours at 37° C. The solution was then dialyzed (Mwt cut off 10 kDa) against water in a magnetic stirrer (magnetic stir bar stirred at 100 rpm) at room temperature for 24 hours to remove any residual materials. The resulting product was then frozen to −80° C. followed by freeze drying at −47° C. at 60 mTorr vacuum for 12 to 14 hours. The efficiency of PEGylation observed over various incubation times is shown in Table 6-1 below, where the efficiency percentages were determined using a TNBS assay procedure, as described above.

Other molecular weight PEGs, such as from 500 to 5000 Da, can be used. Similarly PEG derivatives such as methoxy PEG-N-hydroxyl succinate ester or other derivatives can also be used.

TABLE 6-1

| Incubation time (hrs) | Zein:mPEG ester ratio | PEGylation Efficiency (%) |
|---|---|---|
| 24 | 1:1 | 65 |
| 24 | 1:2 | 93 |
| 3 | 1:1 | 52 |

Fifty milligrams of PEGylated white zein were dissolved in a mixture of 3 mL ethanol and 0.25 mL deionized water. The PEGylated zein solution containing was then added drop wise into 15 mL of citrate buffer having a pH 7.4 and containing PLURONIC® F68 (0.9% w/v) under constant application of ultrasonic energy at 1.39 kW/h and 37% amplitude for 10 minutes with a pulse on-time of 10 seconds and off-time of 1 second. During the sonication process the solution was maintained in an ice bath to maintain the temperature at about 10° C. Subsequently, the zein suspension was placed on a magnetic stirrer at 300 to 500 rpm at room temperature until the ethanol was completely evaporated. When evaporation was complete, the nanoparticles were purified.

Figure 18:
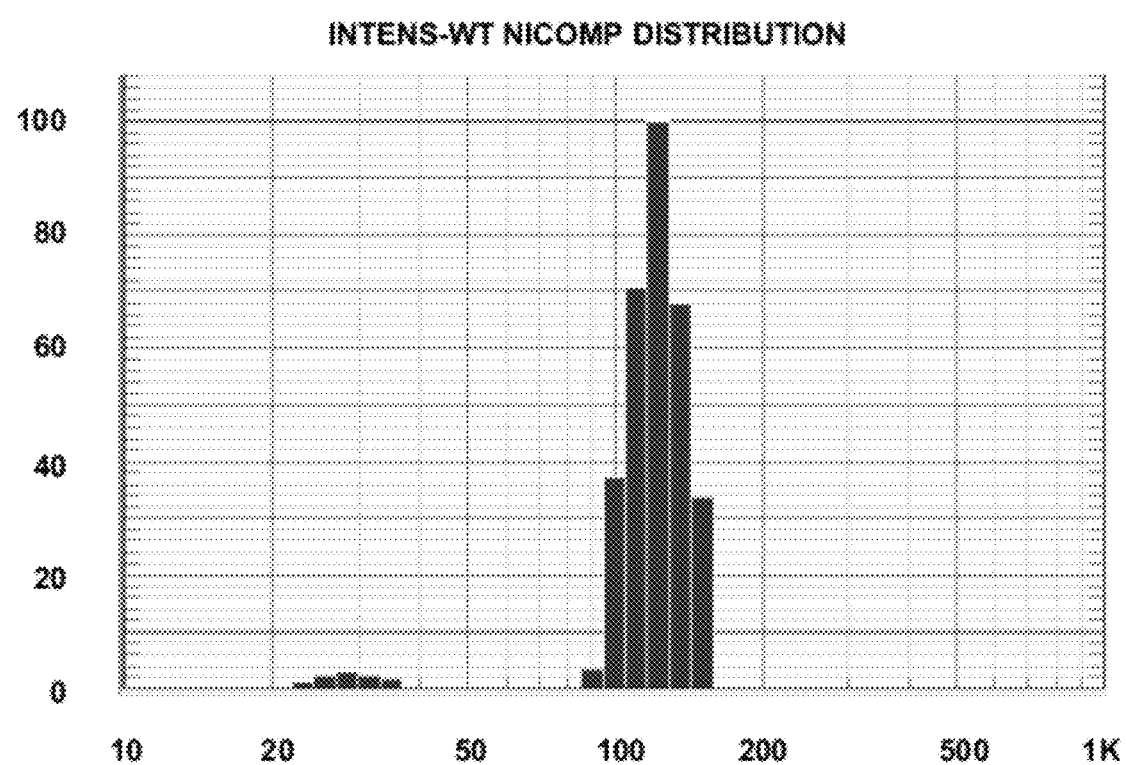
FIG. 18 is a graph illustrating an intensity weighted size distribution of PEGylated nanoparticles. The x-axis shows the particle size in nm and the y-axis corresponds to intensity. The particle size of PEGylated zein nanoparticles was 131±1 nm (n=3), with a Polydispersity Index (PDI) of 0.282±0.01 (n=3).

Purification was accomplished by repeated washing with pH 7.4 citrate buffer and ultracentrifugation using centrifugal filter of MWt cut off of 10000 Da, at 44,000 g for 35 minutes. To the aqueous suspension (pH 7.4 citrate buffer) of PEGylated zein nanoparticles was added 30 g of 2% w/v trehalose and the solution was kept at −80° C. to form to solid cake, which was then lyophilized at −47° C. and 60 mTorr vacuum for 12 to 14 hours. The PEGylation process disclosed above may be carried out using high pressure homogenization as disclosed in Example 2, above. The size distribution of the PEGylated nanoparticles is shown in FIG. 18.

Example 7

Retinol Loaded Zein Nanoparticles

This example describes the preparation and characterization of retinol loaded zein nanoparticles, the improved solubility of retinol using zein nanoparticles, the improved stability of retinol by encapsulating in zein nanoparticles, the sustained release of retinol from zein nanoparticles, the ability of zein nanoparticles to enhance skin penetration and skin retention of retinol, and the lack of or reduced skin irritation of the retinol nanoparticulate formulations compared to retinol itself.

1. Preparation and characterization of retinol loaded zein nanoparticles. Zein nanoparticles were prepared using a phase separation method where zein, retinol and butylated hydroxyl toluene (BHT) (an antioxidant) was dissolved in 90% ethanol. This solution was added to a citrate buffer (pH) containing lecithin and PLURONIC as stabilizers. The alcohol was evaporated to form nanoparticles and then the nanoparticles were separated by centrifugation followed by lyophilization. Radiolabeled ($^3$H) retinol along with 'cold' retinol was used in the analysis. In some embodiments, other suitable antioxidants that can be used in place of, or in combination with, BHT include vitamin E, vitamin C, glutathione, ubiquinone, coenzyme Q-10, idebenone, lycopene, green tea, and silymarin.

Figure 19:
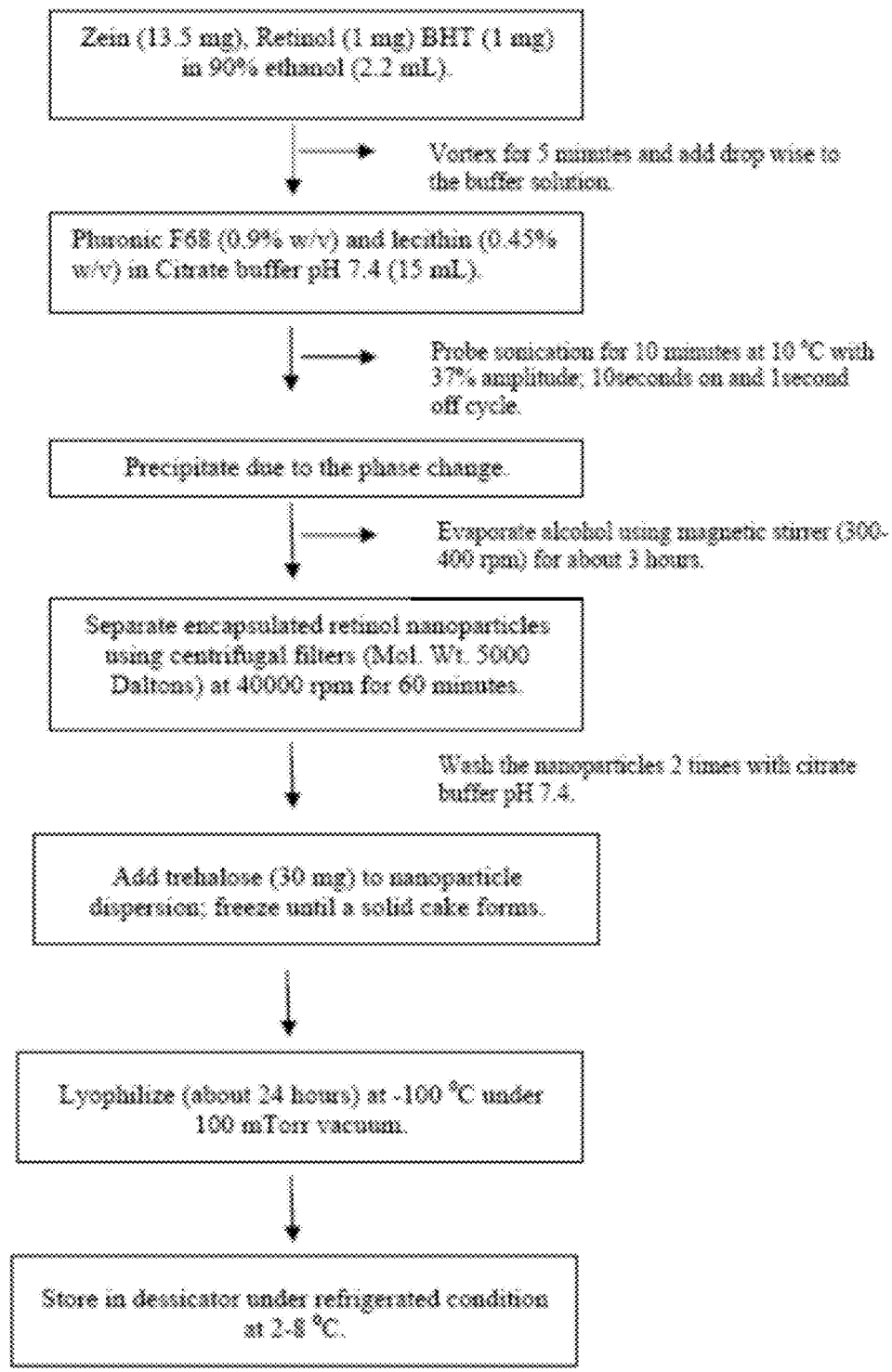
FIG. 19 illustrates by means of a flow chart the general steps to prepare retinol loaded zein nanoparticles using a phase separation method, according to one embodiment.

The particle size of retinol loaded zein nanoparticles was about 170-290 nm and the encapsulation efficiency was 76-100%. The particle size and encapsulation efficiency was optimized by altering the drug/polymer ratio and the concentration of BHT. In the absence of BHT, the encapsulation efficiency was <50%. Table 7-2 provides data for the characterization of retinol-loaded zein nanoparticles. See FIG. 19 for a flow chart that provides an example of the preparation of retinol-loaded zein nanoparticles.

TABLE 7-1

Characteristics of retinol-loaded zein nanoparticles prepared using the phase separation method.

| S. No | Retinol (% w/w) | BHT | Particle size (nm) | PDI | Encapsulation Efficiency (%) |
|---|---|---|---|---|---|
| 1 | 0.074 | ... | 298.5 ± 7.9 | 0.228 ± 0.02 | 46.3 ± 6.2 |
| 2 | 0.074 | 0.074 | 287.0 ± 11.2 | 0.241 ± 0.11 | 85.4 ± 4.1 |
| 3 | 0.148 | 0.296 | 221.7 ± 9.6 | 0.289 ± 0.07 | 75.5 ± 3.9 |
| 4 | 0.074 | 0.148 | 189.5 ± 10.1 | 0.433 ± 0.09 | 96.2 ± 3.3 |

Results are representative of triplicate samples (average ± SD); PDI = polydispersity index.

Figure 20:
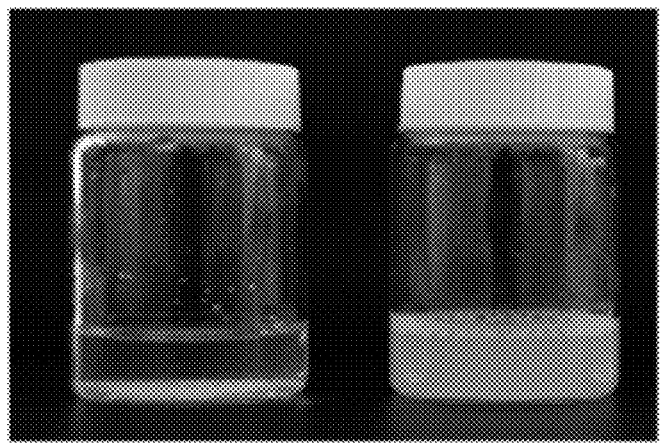
FIG. 20 illustrates the water dispersibility of free retinol and retinol loaded nanoparticles from left to right. The nanoparticles were prepared using the method as described in FIG. 19.

2. Increased solubility/dispersibility of retinol in aqueous solution. Free retinol was not dispersible in water and settled at the bottom of the vial after attempted dispersion of the agent (FIG. 20). On the other hand, retinol loaded zein nanoparticles easily dispersed in water. The solubility of retinol in phosphate buffer (pH 7.4) was significantly enhanced after encapsulation in nanoparticles. A 10 µg/mL sample of retinol (retinol equivalent) nanoparticles in phosphate buffer (pH 7.4) showed comparable UV absorbance (320 nm) to 10 µg/mL of free retinol in 20% methanol. Very little absorbance was observed in the 10 µg/mL dispersion of retinol in phosphate buffer (pH 7.4).

Figure 21:
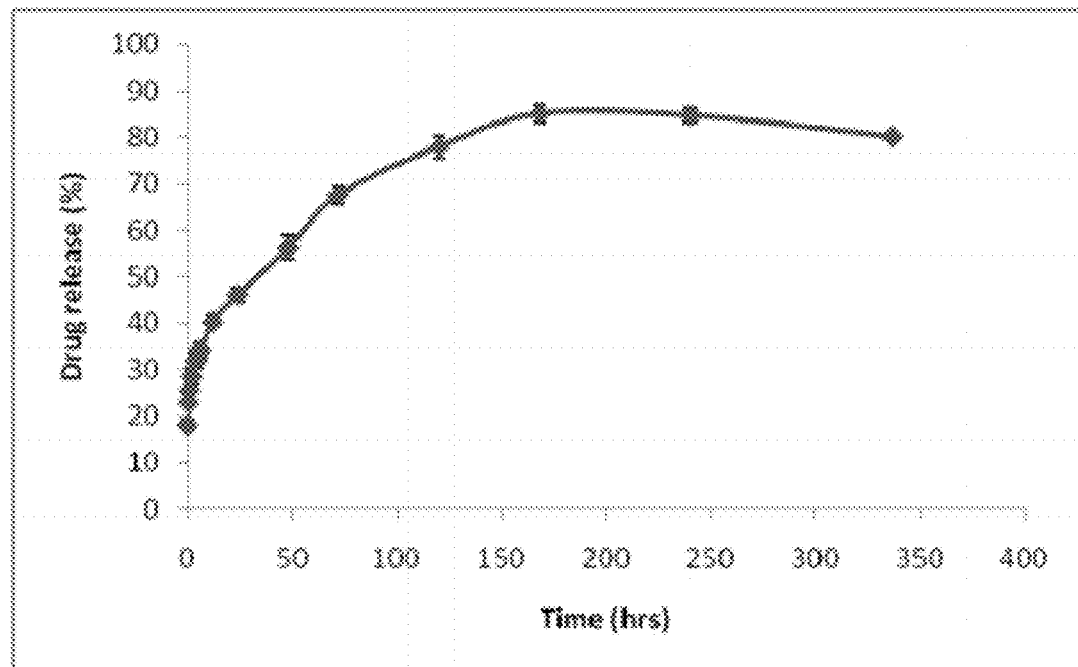
FIG. 21 illustrates the in vitro release of retinol from zein nanoparticles in phosphate buffer (pH 7.4). The retinol concentration was measured by UV-visible spectrophotometry at 320 nm (mean±SEM; n=3). The nanoparticles were prepared using the method as described in FIG. 19.

3. Release of retinol from zein nanoparticles. Release studies of the retinol from nanoparticles were carried out in phosphate buffer saline (PBS; pH 7.4). The concentration of retinol was analyzed using UV Spectrophotometer at 320 nm, and the release studies were carried out in triplicate. Retinol release was sustained for days from zein nanoparticles, as shown in FIG. 21.

Figure 22:
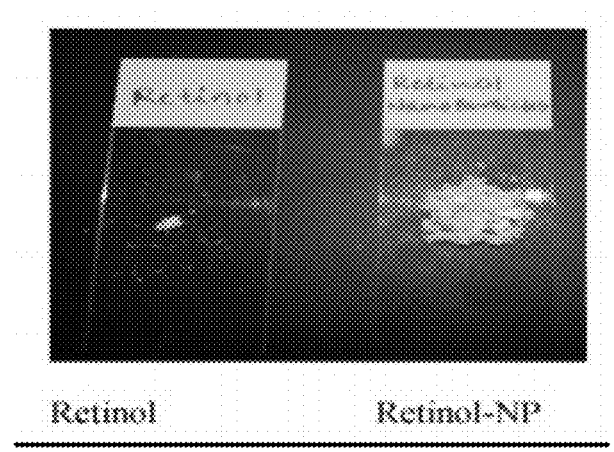
FIG. 22 illustrates free retinol and lyophilized retinol nanoparticles, from left to right. The figure shows the hygroscopic nature of pure retinol and that the retinol nanoparticles are non-hygroscopic free flowing powders. The nanoparticles were prepared using the method as described in FIG. 19.
Figure 23:
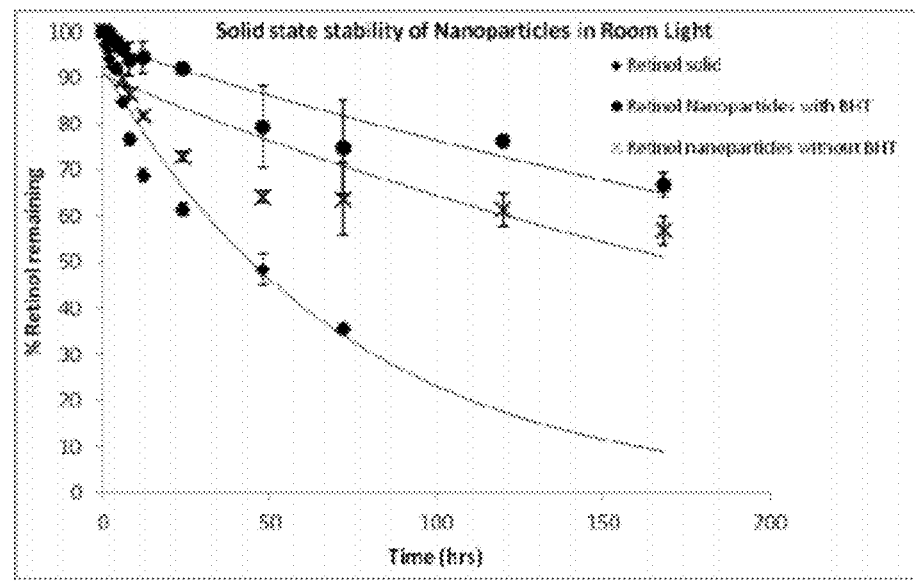
Figure 24:
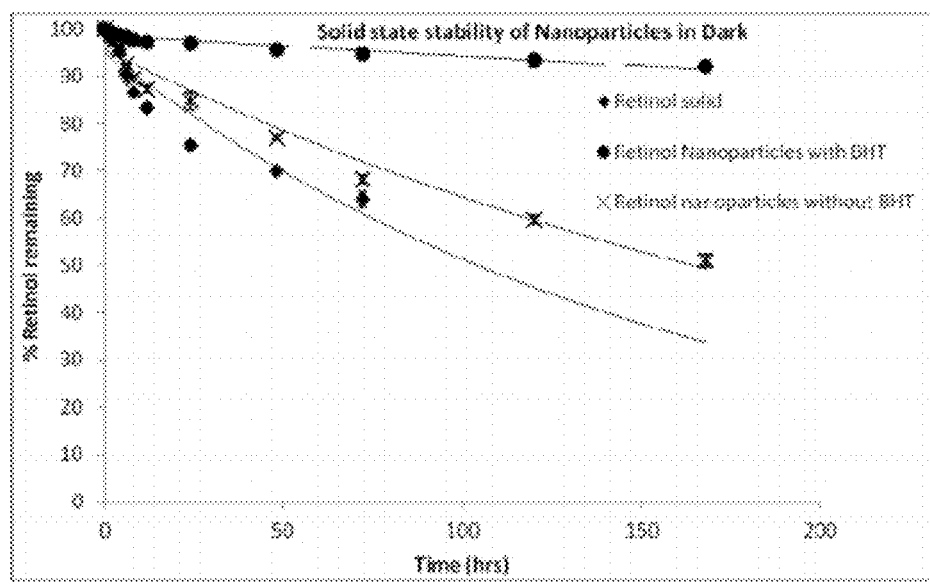
Figure 25:
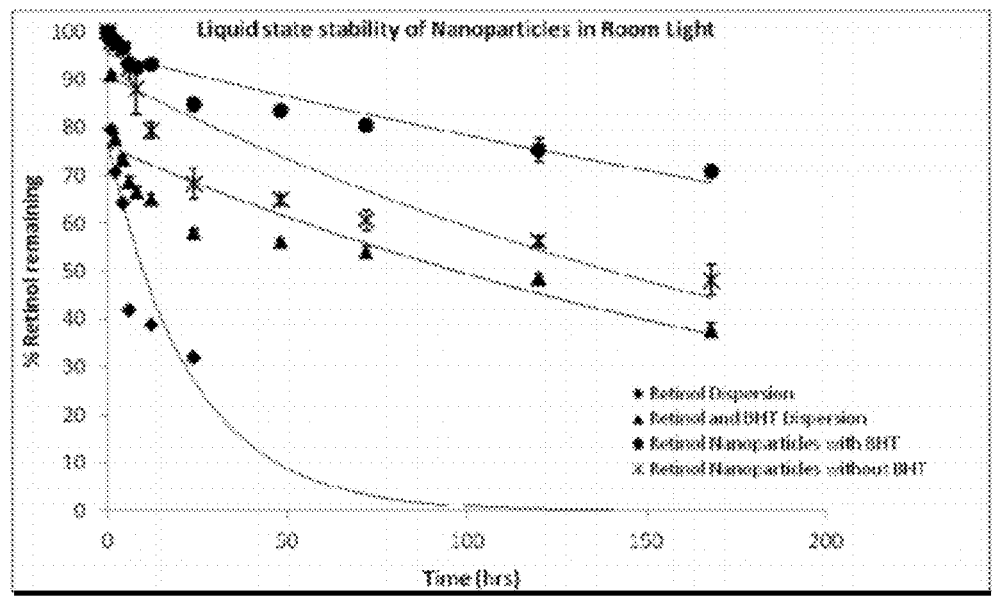
Figure 26:
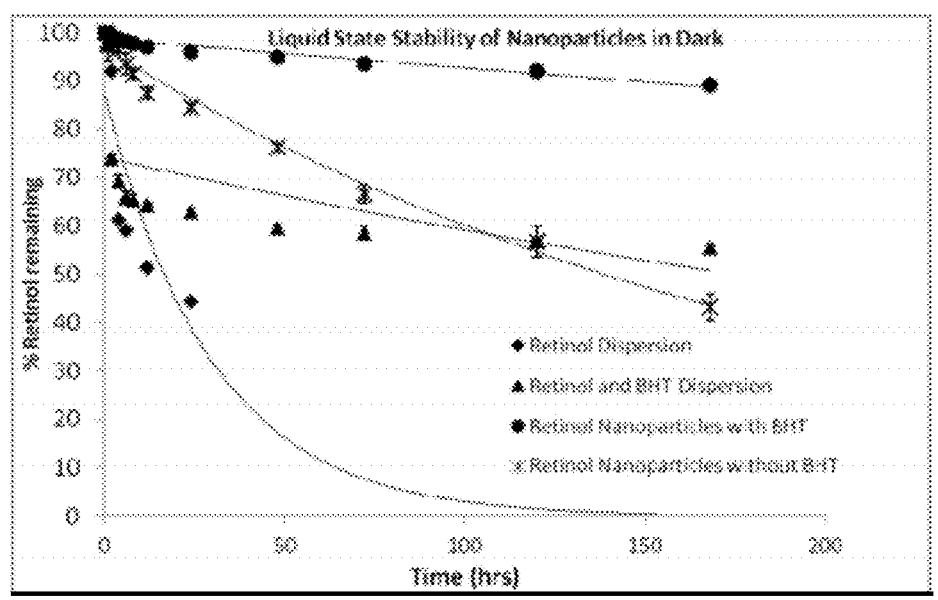

4. Stability of retinol loaded zein nanoparticles. Retinol is a yellow colored powder. It is hygroscopic at ambient conditions and quickly becomes sticky. The encapsulated retinol is colorless and free flowing, and is far less hygroscopic (FIG. 22). The retinol sample shown in FIG. 22 was bright yellow and the nanocarrier formulation was white, demonstrating that encapsulation masks the bright yellow color of retinol. The nanocarrier formulations also resulted in a more free flowing powders than pure retinol.

The stability of retinol formulations under ambient conditions and in dark was studied for a period of one week. The solid stability of retinol and retinol loaded nanoparticles (lyophilized powder) were also studied for one week. For liquid state stability, free retinol or retinol loaded nanoparticles was dispersed in phosphate buffer (pH 7.4) and the retinol concentration was measured for a week using a UV spectroscopy method (at 320 nm). Retinol was found to follow first order kinetics and the half-life was determined. The following results were obtained as shown in Tables 7-2 and 7-3 and FIGS. 23-26.

Zein nanoparticles protected retinol against photodegradation and moisture induced degradation. The encapsulated retinol showed enhanced stability compared to free retinol in the solid state and in liquid state. Inclusion of BHT as an antioxidant further enhanced the stability of encapsulated retinol. Finally, the shelf-life of retinol was significantly enhanced by encapsulation in zein nanoparticles.

TABLE 7-2

Solid state stability of free and encapsulated retinol.

| Substance | Light ($t_{1/2}$ in hrs) | Dark ($t_{1/2}$ in hrs) |
|---|---|---|
| Retinol solid | 52.75 | 63 |
| Retinol nanoparticles | 153 | 92.66 |
| Retinol nanoparticles with BHT | 346.5 | 1386 |

TABLE 7-3

Liquid state stability of free and encapsulated retinol in phosphate buffer (pH 7.4).

| Substance | Light ($t_{1/2}$ in hrs) | Dark ($t_{1/2}$ in hrs) |
|---|---|---|
| Retinol | 16.11 | 20.83 |
| Retinol + BHT | 35.25 | 43.42 |
| Retinol nanoparticles | 42 | 94.81 |
| Retinol nanoparticles with BHT | 110.1 | 347 |

Figure 27:
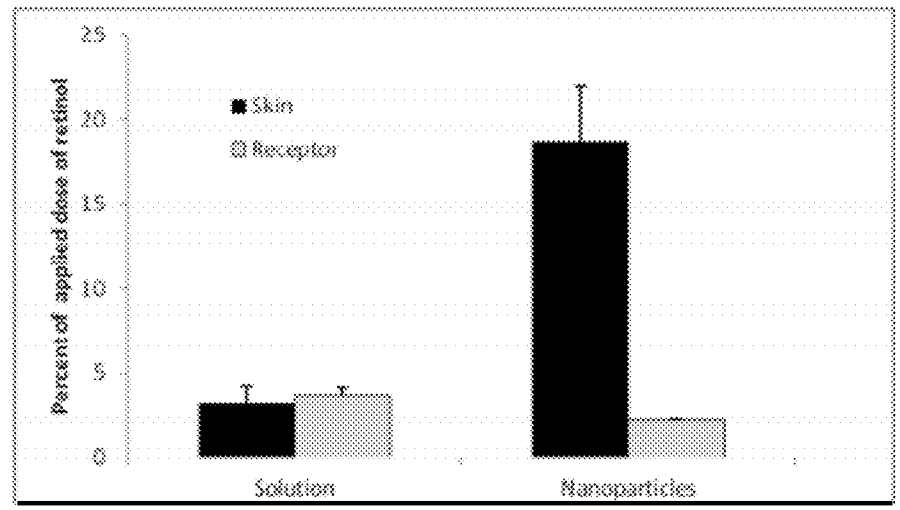
FIG. 27 illustrates the percentage of applied retinol at the end of 48 hours in porcine skin and in receptor medium after treatment with free retinol and retinol encapsulated in zein nanoparticles. Excised porcine skin was sandwiched between the two compartments of a vertical diffusion cell. The receptor medium consisted of phosphate buffer (pH 7.4) maintained at 37° C. and stirred using a magnetic bead. Free or encapsulated retinol dispersion in phosphate buffer (pH 7.4) was loaded in the donor chamber. At the end of the study, the retinol concentration in the skin and receptor compartment was measured by radiochemical method using $^3$H labeled retinol. The skin was digested using 0.1M sodium hydroxide to determine the retinol concentration. (mean±SD; n=6). The nanoparticles were prepared using the method as described in FIG. 19.

5. Skin penetration of retinol and encapsulated retinol. The skin penetration of retinol and encapsulated retinol was studied using excised porcine ear skin using a vertical diffusion cell. Radiolabeled ($^3$H) retinol along with 'cold' retinol was used in this study. The amount of retinol in the skin homogenate and receptor medium at the end of 48 hours was estimated using radiochemical analysis. The experiments were repeated 6 times (±SD). As can be seen in FIG. 27, the encapsulated retinol resulted in greater retention of retinol in the skin. The ratio of "retinol in skin to receptor" was 3 and 11, for free retinol and retinol nanoparticles respectively. The results show that nanoparticles resulted in greater retention of retinol in the skin.

In summary, zein nanoparticles significantly increased the aqueous solubility and dispersibility of retinol. Encapsulation of retinol in nanoparticles resulted in a free flowing colorless powder, unlike free retinol, which is a yellow, sticky and hygroscopic powder. Zein nanoparticles effectively sustained the release of retinol. Photostability and hydrolytic stability of retinol is significantly enhanced by encapsulating in zein nanoparticles, which was further enhanced by addition of BHT as an antioxidant, and zein nanoparticles resulted in higher skin retention of retinol. The nanoparticles can also reduce the skin irritation of retinol.

Example 8

Rhodamine 123 Loaded Non Cross Linked Zein Nanoparticles

The general steps for preparing rhodamine 123 (0.0296% and 0.0370% w/w) loaded non cross linked zein nanoparticles using a phase separation method are provided below in Table 8-1.

TABLE 8-1

Phase Separation Method For Preparing Rhodamine Nanoparticles.

| Procedure: | Followed by: |
|---|---|
| 1. Zein (13.5 mg) and Rhodamine 123 (0.4 mg/0.5 mg) are dissolved in 90% ethanol (2.2 mL) | Vortexing for 5 minutes and drop wise addition to the buffer solution |
| 2. Buffer solution: PLURONIC F68 (0.9% w/v) and lecithin (0.45% w/v) in Citrate buffer pH 7.4 (15 mL) | Probe sonication for 10 minutes at 10° C. with 37% amplitude; 10 seconds on and 1 second off cycle |
| 3. Precipitate due to the phase change | Evaporate alcohol using magnetic stirrer (300-400 rpm) for about 3 hours |
| 4. Separate encapsulated retinol nanoparticles using centrifugal filters (Mol. Wt. 5 kDa) at 4000 rpm for 60 minutes | Wash the nanoparticles 2 times with citrate buffer pH 7.4 |
| 5. Trehalose (30 mg) is added to nanoparticle dispersion; dispersion is frozen until it a solid forms | |
| 6. Lyophilize (for about 24 h) at −100° C. under 100 mTorr vacuum | |
| 7. Store in dessicator under refrigerated conditions at 2-8° C. | |

Figure 29:
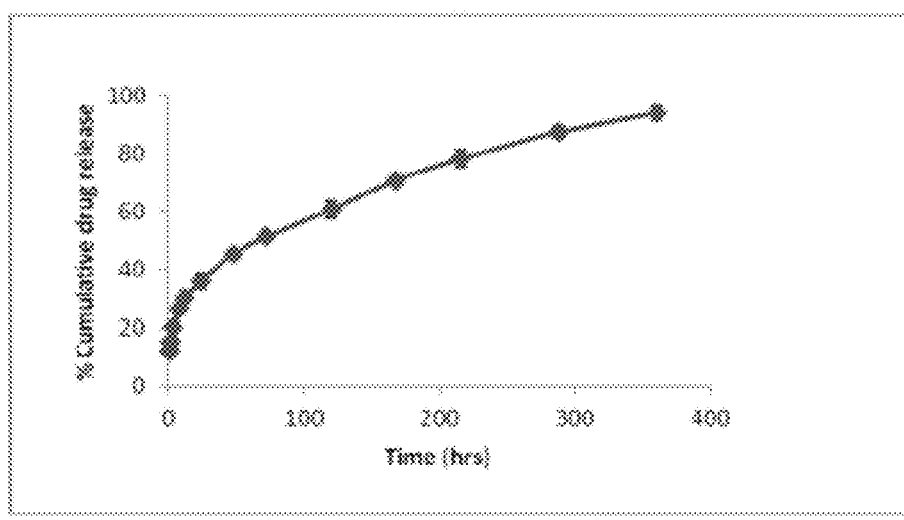
FIG. 29 illustrates the in vitro release of rhodamine 123 from zein nanoparticles in phosphate buffer (pH 7.4). The nanoparticles were prepared using the method described in Table 8-1.

FIG. 29 illustrates the in vitro release of rhodamine 123 from zein nanoparticles in phosphate buffer (pH 7.4). In these studies, 0.096% w/w rhodamine 123 loaded non-cross linked nanoparticles were used for the study. The rhodamine 123 concentration was measured by a spectrofluorimeter at the excitation wavelength of 485 nm and emission wavelength of 530 nm (mean±SEM; n=3).

Figure 30:
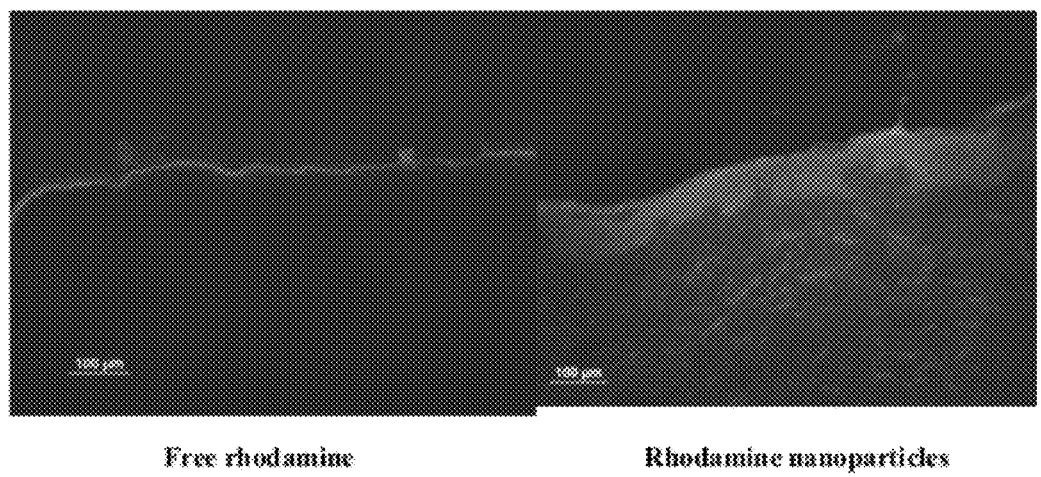
FIG. 30 illustrates the penetration of free rhodamine 123 (10 μg) and rhodamine nanoparticles (equivalent to 10 μg of rhodamine 123) in porcine dermatomed skin after 6 hours.

FIG. 30 illustrates the penetration of free rhodamine 123 (10 μg) and rhodamine nanoparticles (equivalent to 10 μg of rhodamine 123) into the porcine dermatomed skin after 6 hours. Excised porcine skin was sandwiched between the two compartments of a vertical diffusion cell. The receptor medium consisted of phosphate buffer (pH 7.4) maintained at 37° C. and stirred using a magnetic bead. Free rhodamine 123 and rhodamine nanoparticle dispersion in phosphate buffer (pH 7.4) was loaded in the donor chamber. At the end of the study, the skin was washed thoroughly to remove the surface adsorbed rhodamine 123 and the skin was placed in the OCT fluid and frozen in the liquid nitrogen. Later the skin was sectioned with cryotome and observed under a fluorescent microscope. As can be seen from FIG. 30, the rhodamine nanoparticles penetrated deeper into the skin compared to free rhodamine, which was restricted to the top layer of skin (SC).

Figure 31:
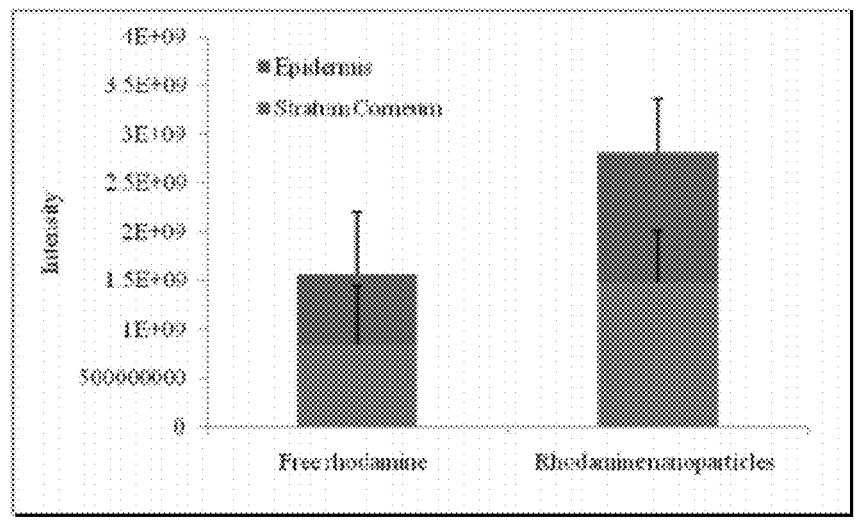
FIG. 31 illustrates the fluorescence pixels from free rhodamine 123 (10 μg) and encapsulated rhodamine 123 (equivalent to 10 μg of rhodamine 123) in zein nanoparticles in porcine dermatomed skin after 6 hours of treatment. For stratum corneum (SC) 0-20 μm and for epidermis 20-100 μm XZ optical sections from confocal microscopic images were used for quantifying the fluorescence pixels. The nanoparticles were prepared using the method described in Table 8-1.

FIG. 31 illustrates the penetration of free rhodamine 123 (10 μg) and encapsulated rhodamine 123 (equivalent to 10 mg of rhodamine 123) in zein nanoparticles into the porcine dermatomed skin after 6 hours. Excised porcine skin was sandwiched between the two compartments of a vertical diffusion cell. The receptor medium consisted of phosphate buffer (pH 7.4) maintained at 37° C. and stirred using a magnetic bead. Free or encapsulated rhodamine 123 dispersion in phosphate buffer (pH 7.4) was loaded in the donor chamber. At the end of the study, the skin was washed thoroughly and the rhodamine 123 fluorescence in the skin was measured using the confocal laser scanning microscopy and quantified using the fluorescence pixel intensity in different layers of the skin (mean±SE; n=3). As can be seen from FIG. 31, the fluorescence intensity is significantly higher for rhodamine nanoparticles.

Example 9

Fluoroisothiocyanate (FITC) Loaded Zein Nanoparticles

Fluoroisothiocyanate (FITC) has a molecular weight of 389.382 and a Log P of 5.03. FITC is a fluorescent dye slightly soluble in water (less than 0.1 mg/mL) and completely soluble in ethanol, methanol, dimethyl sulfoxide and dimethylformamide.

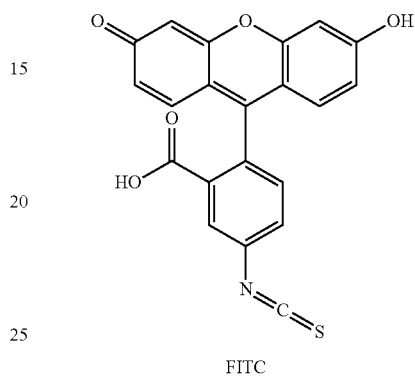

FITC

Characteristics of FITC-loaded zein nanoparticles prepared using an emulsion solvent evaporation method are shown in Table 9-1.

TABLE 9-1

| FITC (5 w/w) | Particle size (nm) | PDI | Encapsulation Efficiency (%) |
|---|---|---|---|
| 0.0296 | 304.8 ± 8.25 | 0.312 ± 0.112 | 27.1 ± 6.23 |

Figure 32:
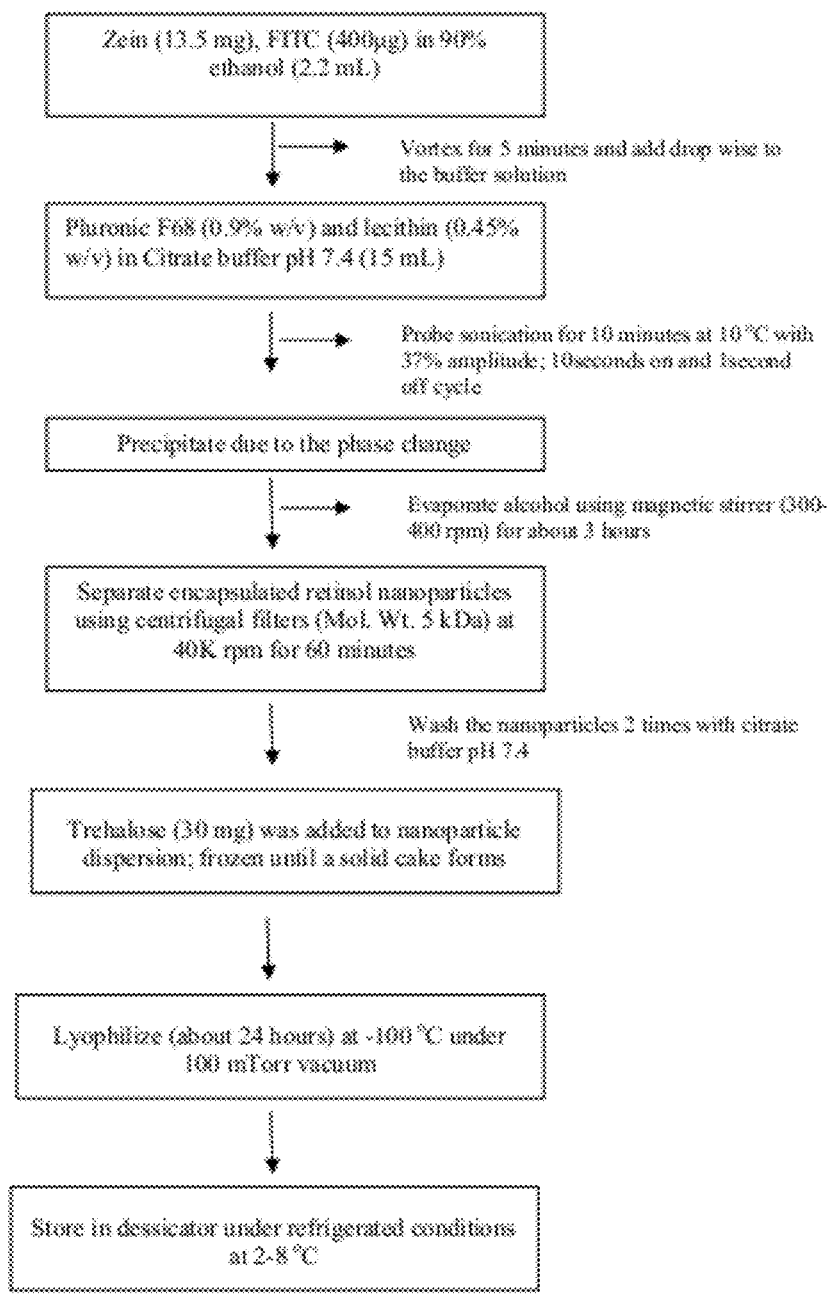
FIG. 32 illustrates by means of a flow chart the general steps of preparation of FITC loaded zein nanoparticles using a phase separation method, according to one embodiment.

FIG. 32 illustrates by means of a flow chart the general steps of preparation of FITC loaded zein nanoparticles using an emulsion solvent evaporation method, according to one embodiment.

Figure 33:
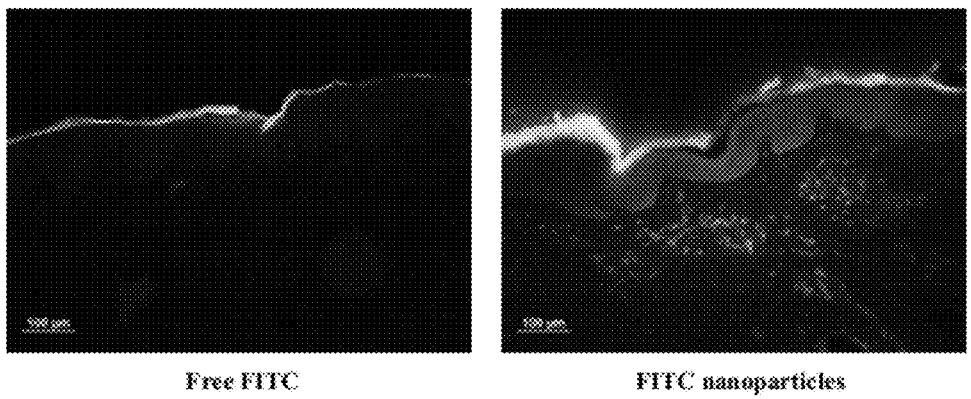
FIG. 33 illustrates the penetration of free FITC (10 μg) and FITC nanoparticles (equivalent to 10 μg) into porcine dermatomed skin after 6 hours. Skin was cryosectioned and observed under fluorescence microscope.

FIG. 33 illustrates the penetration of free FITC (10 μg) and FITC nanoparticles (equivalent to 10 μg) into porcine dermatomed skin after 6 hours. Excised porcine skin was sandwiched between the two compartments of a vertical diffusion cell. The receptor medium consisted of phosphate buffer (pH 7.4) maintained at 37° C. and stirred using a magnetic bead. Free FITC and FITC nanoparticle dispersion in phosphate buffer (pH 7.4) were loaded in separate donor chambers. At the end of the study, the skin was washed thoroughly to remove the surface adsorbed FITC and the skin was placed in the OCT fluid and frozen in liquid nitrogen. The skin was then sectioned with cryotome and observed under a fluorescent microscope. As can be seen from FIG. 33, the FITC nanoparticles penetrated deeper into the skin compared to free FITC, which was restricted to the top layer (SC) of skin.

Figure 34:
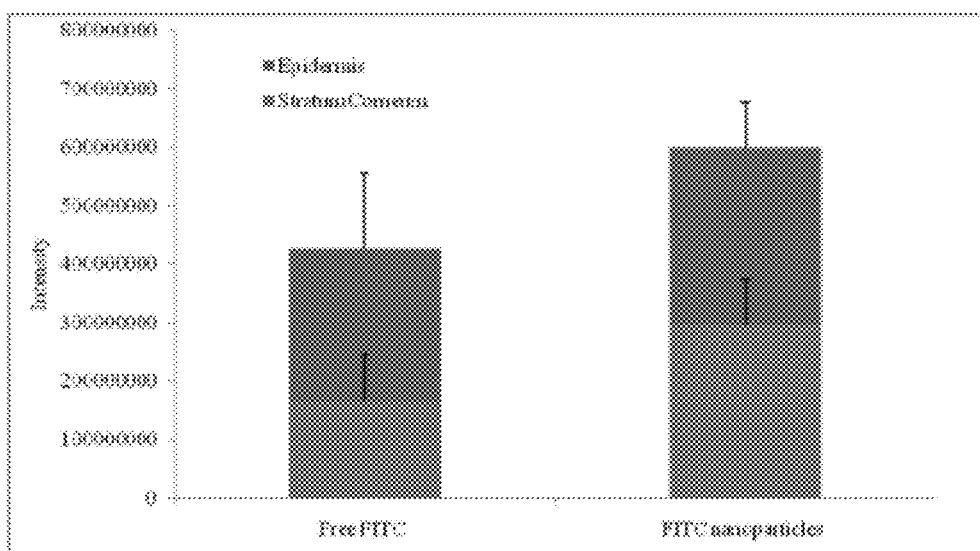
FIG. 34 illustrates the fluorescence pixels from free MC (10 μg) and encapsulated FITC (equivalent to 10 μg) in zein nanoparticles in porcine dermatomed skin after 6 hours of treatment. For stratum corneum (SC) 0-20 μm and for epidermis 20-100 μm XZ optical sections from confocal microscopic images were used for quantifying the fluorescence pixels.

FIG. 34 illustrates the penetration of free FITC (10 μg) and encapsulated FITC (equivalent to 10 μg) in zein nanoparticles into porcine dermatomed skin after 6 hours. Excised porcine skin was sandwiched between the two compartments of a vertical diffusion cell. The receptor medium consisted of phosphate buffer (pH 7.4) maintained at 37° C. and was stirred using a magnetic bead. Free or encapsulated FITC dispersion in phosphate buffer (pH 7.4) was loaded in the donor chamber. At the end of the study, the skin was washed thoroughly and the FITC concentration in the skin was measured using the confocal laser scanning microscopy and quantified using the fluorescence pixel intensity in different layers of the skin (mean±SE; n=3). As shown in FIG. 34, the fluorescence intensity is higher for FITC nanoparticles in the SC.

Example 10

5-Fluorouracil (5-FU) Loaded Zein Nanoparticles

5-Fluorouracil (5-FU) has a molecular weight of 130.077 and a Log P of −0.89. 5-FU is partially soluble in cold water and methanol, is completely soluble in dimethyl sulfoxide and dimethylformamide, and is insoluble in diethyl ether.

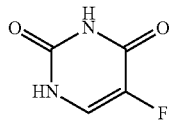

5-FU is a hydrophilic drug (log P=−0.89) and is poorly permeable through skin (Cornwell and Barry, Int J Pharm 94, 189-194, 1993). The drug is used in the treatment of, for example, psoriasis, premalignant (actinic keratosis) and malignant (skin cancer) skin conditions (Tsuji and Sugai, Arch Dermatol 105, 208-212, 1975; Goette, J Am Acad Dermatol 4, 633 649, 1981). Characteristics of 5-fluorouracil-loaded zein nanoparticles prepared using an emulsion solvent evaporation method are shown in Table 10-1.

TABLE 10.1

Characteristics of 5-Flurouracil-Loaded Zein Nanoparticles.

| 5-flurouracil (% w/w) | Particle size (nm) | PDI | Encapsulation Efficiency (%) |
|---|---|---|---|
| 0.370 | 300.5 ± 21.76 | 0.321 ± 0.144 | 17.8 ± 3.36 |

Figure 35:
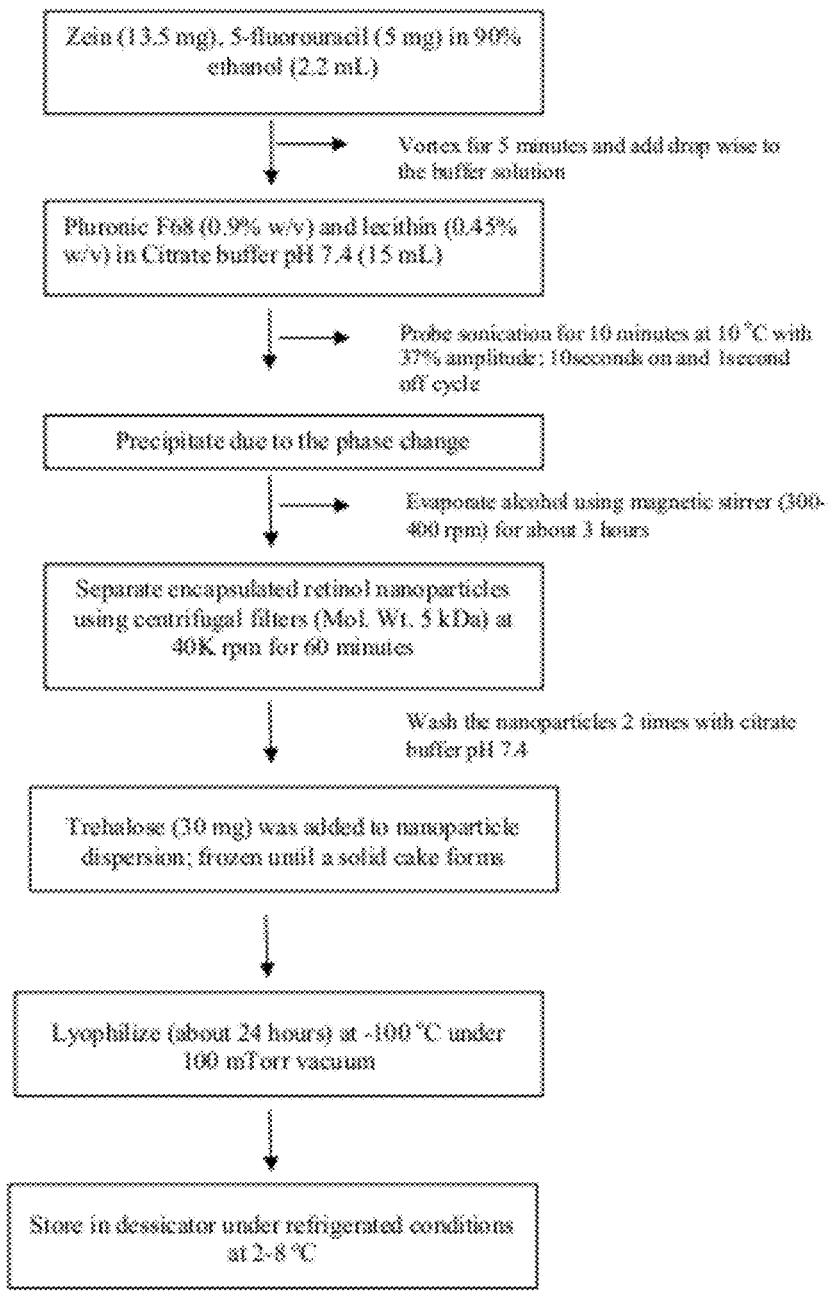
FIG. 35 illustrates by means of a flow chart the general steps for preparing 5-fluorouracil loaded zein nanoparticles using a phase separation method, according to one embodiment.

FIG. 35 illustrates by means of a flow chart the general steps for preparing 5-fluorouracil loaded zein nanoparticles using an emulsion solvent evaporation method, according to one embodiment.

Figure 36:
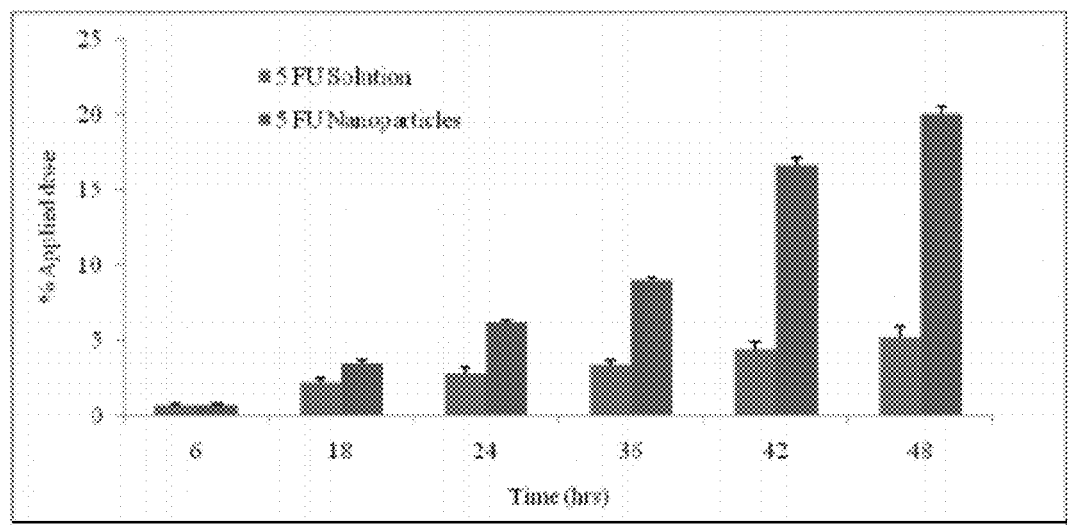
FIG. 36 illustrates the percentage of applied 5-fluorouracil (5 FU) in receptor medium.

FIG. 36 illustrates the percentage of applied 5-fluorouracil (5-FU) in receptor medium. Excised dermatomed porcine skin was sandwiched between the two compartments of a vertical diffusion cell. The receptor medium consisted of phosphate buffer (pH 7.4) maintained at 37° C. and stirred using a magnetic bead. Free or encapsulated 5-FU dispersion in phosphate buffer (pH 7.4) was loaded in the donor chamber. The 5-FU concentration in the receptor compartment was measured at various intervals by radiochemical method using $^{14}C$ labeled 5-FU (mean±SE; n=3). As can be seen from FIG. 36, the zein nanoparticles significantly enhanced the skin penetration of 5-FU. The results demonstrate that zein nanoparticles can act as a skin penetration enhancer due to the presence of PLURONIC® and lecithin.

Example 11

Zein-Casein Nanoparticles

Novel zein-casein core shell nanoparticles have been prepared, where the hydrophobic zein forms the core, while the hydrophilic milk protein β-casein forms the hydrophilic shell. Other hydrophobic prolamine such as gliadin, kafirin and hoferidin can also be used in place of zein, and other caseins such as kappa or gamma caseins or sodium caesinate may be used in place of casein. Advantages of this novel system include that both zein and casein are biodegradable and biocompatible food proteins. Casein is an amphiphilic surfactant that stabilizes zein nanoparticles, preventing aggregation, and forming smaller sized nanoparticles. Casein can help to increase the encapsulation efficiency, and can help to modulate the drug release characteristics of nanoparticles. Drugs can be loaded into the hydrophobic core, hydrophilic shell or both.

Because both zein and casein are proteins, they have numerous functional groups for surface modification or modification of the core. The core and shell can both be independently altered for various applications. For example, either the core and/or shell can be cross linked, as described herein. Similarly, drugs can be complexed and/or conjugated to core and/or shell.

Figure 37:
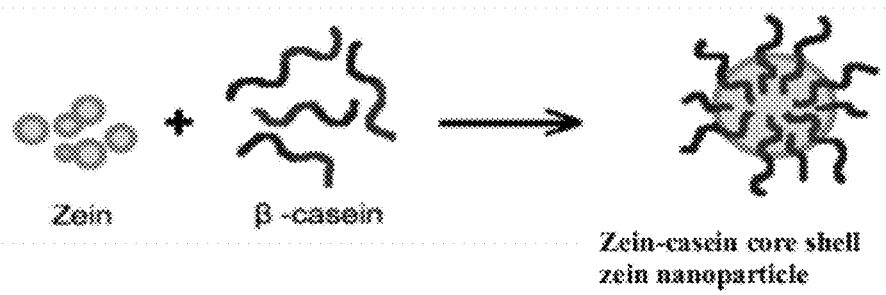
FIG. 37 schematically illustrates the formation of zein-casein core shell nanoparticles.
Figure 38:
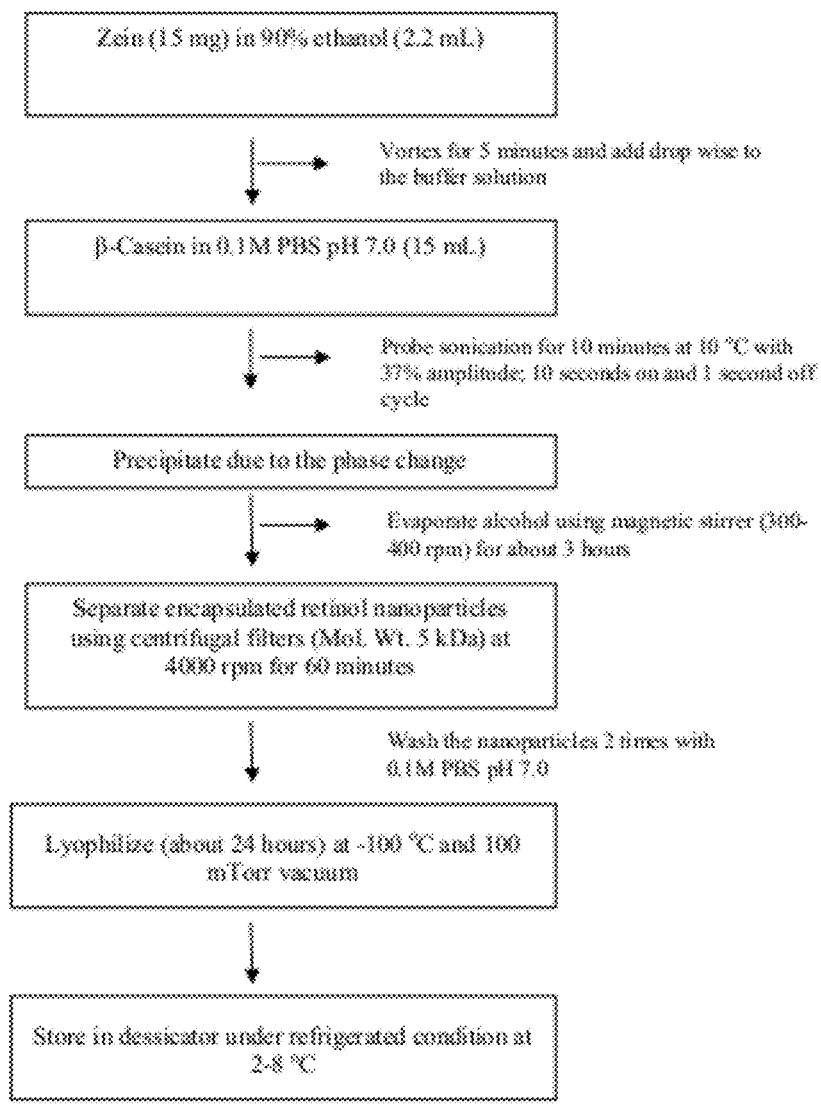
FIG. 38 illustrates by means of a flow chart the general steps for preparing zein nanoparticles stabilized with β-casein using a phase separation method, according to one embodiment.

Casein, being an amphiphilic protein, can interact with skin lipids to increase skin penetration of the nanoparticles. FIG. 37 schematically illustrates the formation of zein-casein core shell nanoparticles. FIG. 38 illustrates by means of a flow chart the general steps for preparing zein nanoparticles stabilized with β-casein using a phase separation method, according to one embodiment. Table 11-1 illustrates various characteristics of zein nanoparticles stabilized with β-casein, prepared using the phase separation method. For the preparation of zein nanoparticles, the β-casein concentration was used in the range of 0.05-1.0% w/v in citrate buffer (pH 7.4).

TABLE 11-1

Characteristics of Zein Nanoparticles Stabilized with β-Casein.

| β-casein (% w/v) | Particle size (nm) | PDI |
|---|---|---|
| 0.05 | 260.0 | 0.543 |
| 0.1 | 110.4 | 0.158 |
| 0.15 | 112.6 | 0.170 |
| 0.2 | 115.2 | 0.143 |
| 0.5 | 119.7 | 0.130 |
| 1.0 | 131.2 | 0.146 |

Figure 39:
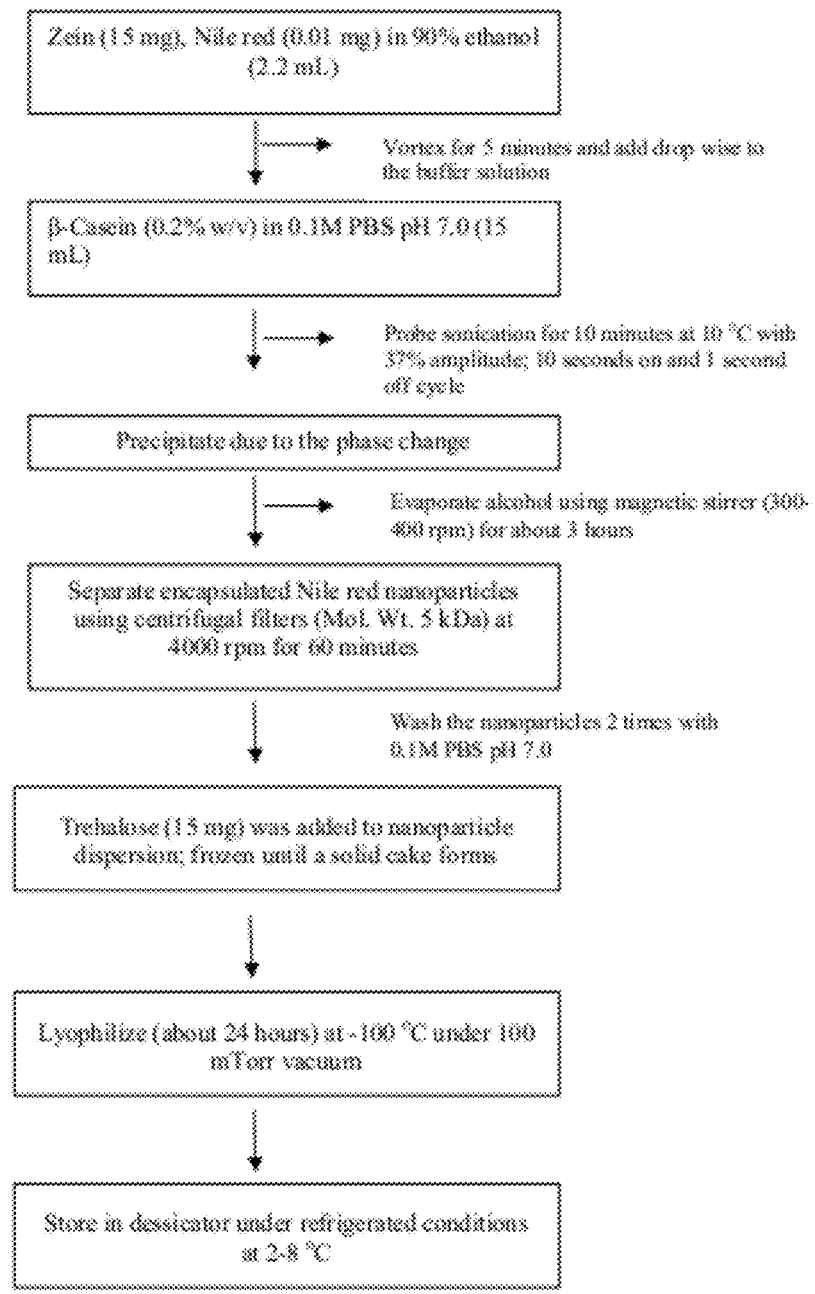
FIG. 39 illustrates by means of a flow chart the general steps for preparing Nile Red loaded zein nanoparticles stabilized with β-casein, using a phase separation method, according to one embodiment.

FIG. 39 illustrates by means of a flow chart the general steps for preparing Nile red loaded zein nanoparticles stabilized with β-casein, using a phase separation method, according to one embodiment. Table 11-2 illustrates various characteristics of Nile red-loaded zein nanoparticles stabilized with β-casein, prepared using a phase separation method. For the preparation of Nile red nanoparticles, the Nile red concentration ranged from 0.0066-0.066% w/w. The β-casein concentration used was 0.1%-0.2% w/v in a citrate buffer (pH 7.4).

TABLE 11-2

Characteristics of Nile red-Loaded Zein Nanoparticles.

| Nile red (% w/w) | Particle size (nm) | PDI | Encapsulation efficiency (%) |
|---|---|---|---|
| 0.0066 | 116.3 | 0.150 | 71.6 |

Figure 40:
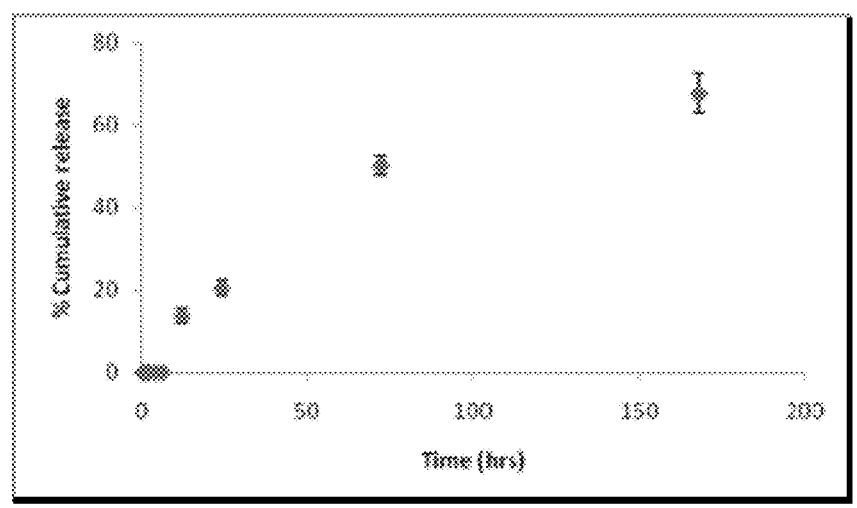
FIG. 40 illustrates the in vitro release of Nile red from zein-casein nanoparticles in phosphate buffer (pH 7.4).
Figure 41:
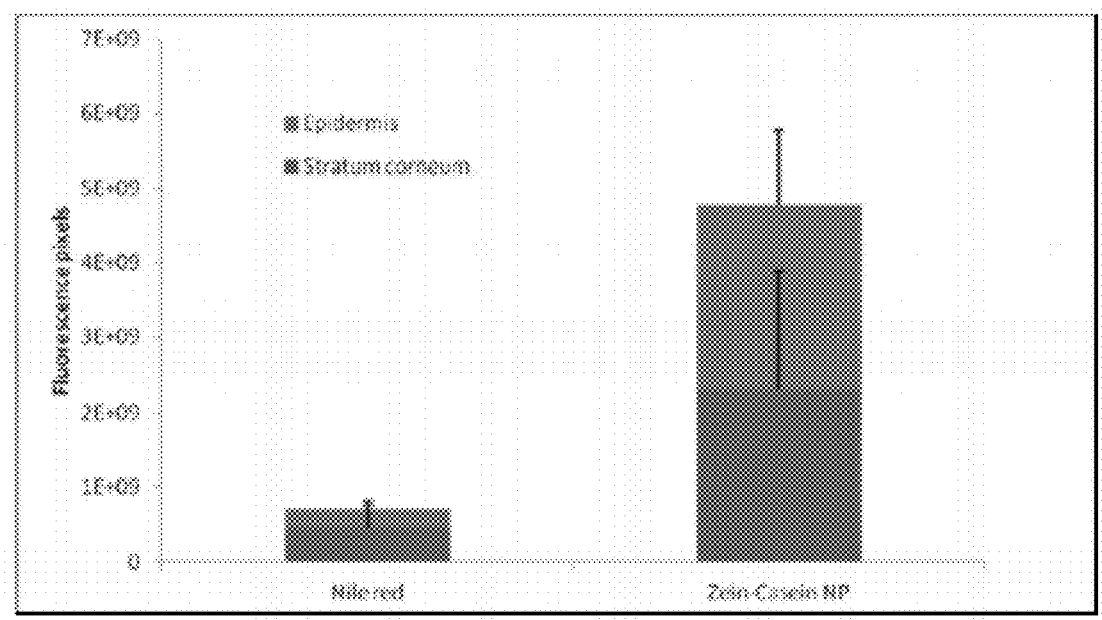
FIG. 41 illustrates by means of a flow chart the general steps for preparing retinol loaded zein nanoparticles stabilized with casein, using a phase separation method, according to one embodiment.
Figure 42:
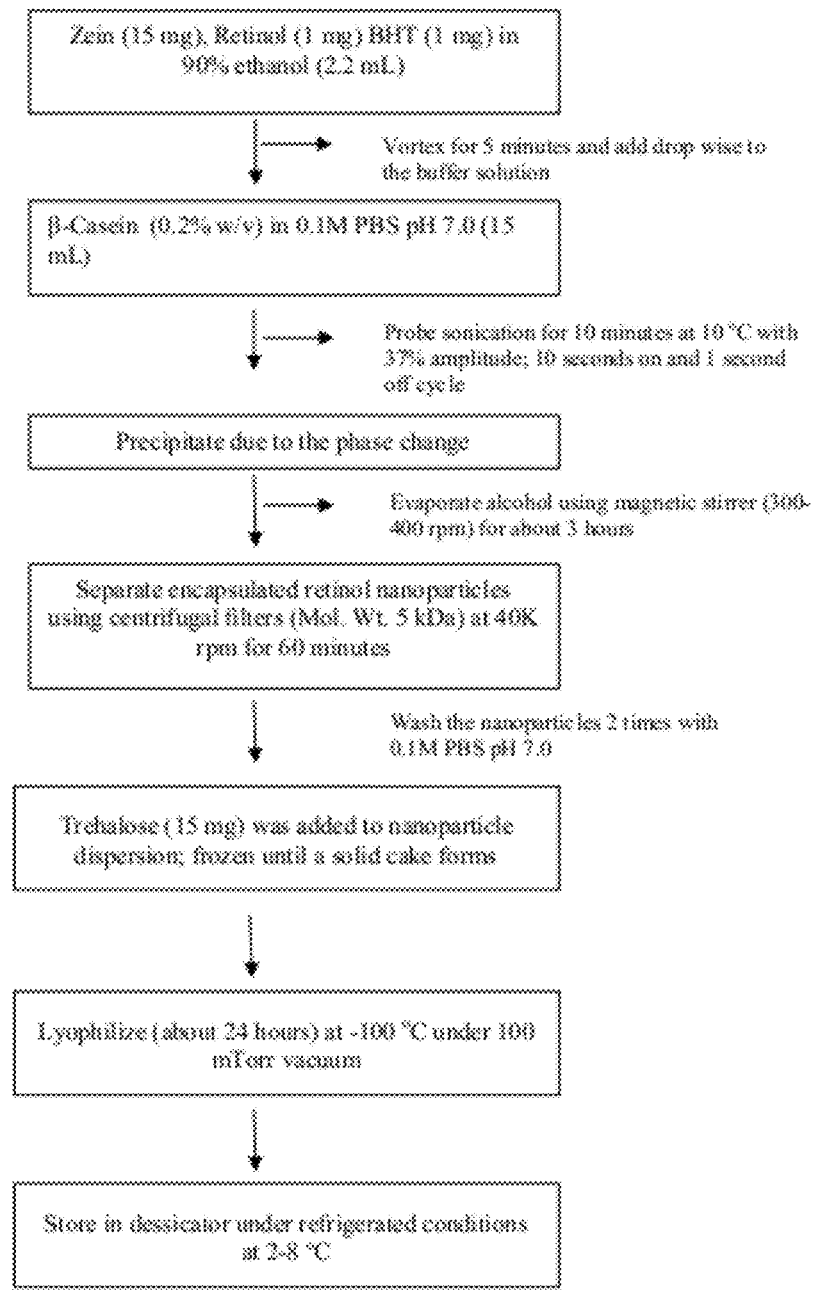

FIG. 40 illustrates the in vitro release of Nile red from zein-casein nanoparticles in phosphate buffer (pH 7.4). The Nile red concentration was measured by a spectrofluorimeter at the excitation wavelength of 559 nm and emission wavelength of 629 nm. (mean±SEM; n=3). FIG. 41 illustrates the skin penetration of free Nile red and Nile red encapsulated in zein-casein nanoparticles. FIG. 42 illustrates by means of a flow chart the general steps for preparing retinol loaded zein nanoparticles stabilized with casein, using a phase separation method, according to one embodiment. Table 11-3 illustrates various characteristics of retinol-loaded zein nanoparticles stabilized with β-casein prepared using phase separation method. For the preparation of retinol nanoparticles, retinol concentration ranges from 0.006-0.066% w/w with the equivalent BHT concentrations were considered. β-casein concentration was used in the range of 0.1-0.2% w/v in citrate buffer (pH 7.4).

TABLE 11-3

Characteristics of Retinol-Loaded Zein Nanoparticles.

| Sample No. | Retinol (% w/w) | BHT (% w/w) | Particle size (nm) | PDI | Encapsulation Efficiency (%) |
| --- | --- | --- | --- | --- | --- |
| 1 | 0.066 | — | 169.6 | 0.407 | 7.77 |
| 2 | 0.066 | 0.066 | 148.9 | 0.331 | 8.53 |

Example 12

Preparation of a Cream Formulation for Retinol Encapsulated in Zein Nanoparticles To demonstrate the feasibility of a skin formulation for delivery for commercial development, a commercial cream base (MEDCO Labs) was used to incorporate free retinol or retinol encapsulated in zein nanoparticles. Cream base contains stearyl alcohol (14%), cetyl ester waxes (3.5%), glyceryl monostearate (2%), polyethylene stearyl ether (3%), sorbitol (10%), isopropyl palmitate (2%), methyl paraben (0.16%), propyl paraben (0.4%) and purified water (65%). Retinol equivalent to 0.1% w/w was weighed and transferred to watch glass and mixed homogenously using a glass rod by geometric dilution. Other formulations; including, but not limited to, oil-water cream, water in oil cream, ointment, gel, and the like may be used. The mixture was spiked with 0.05 μCi of $^3$H retinol and mixed thoroughly in the cream. Finally, the prepared cream formulations were transferred to glass vials and stored until use.

TABLE 12.1

Retinol cream formulations

| Retinol (0.1% w/w) cream - 1 g | |
| --- | --- |
| Retinol | 0.001 g |
| Cream base | 0.800 g |
| Retinol (0.1% w/w) cream - 1 g | |
| Retinol nanoparticles | 0.200 g |
| Cream base | 0.800 g |

Figure 43:
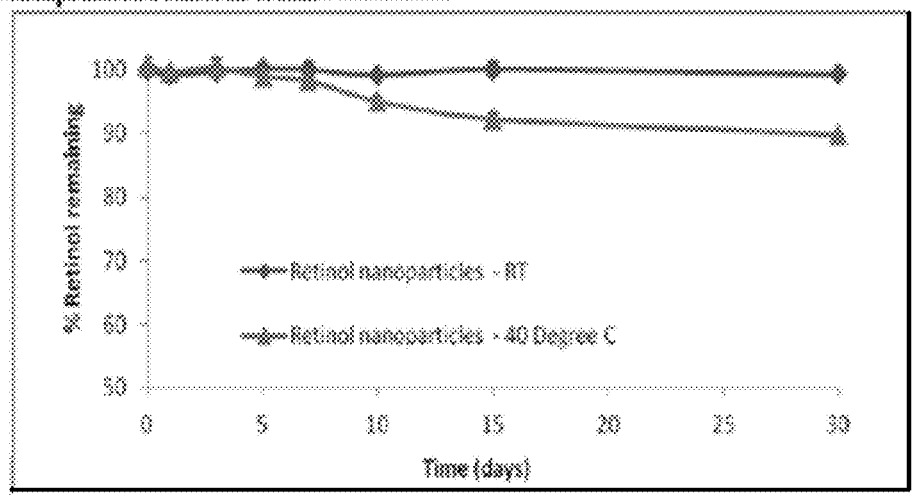
FIG. 43 illustrates the stability of a retinol nanoparticle cream formulation stored at room temperature and 40° C. for a period of one month in a glass vial covered with aluminum foil. At regular intervals an aliquot of the formulation was removed and the retinol content was analyzed using HPLC. The formulation remained stable and did not show any significant degradation at room temperature. Each value is mean±SD; n=3. The nanoparticles were prepared using the method described in FIG. 19.
Figure 44:
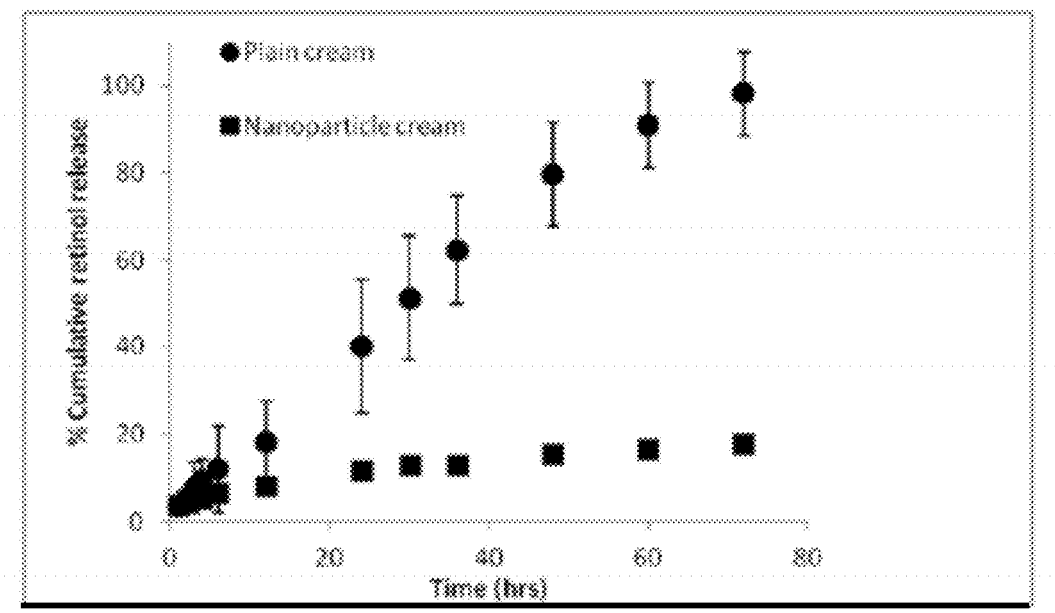
FIG. 44 demonstrates in vitro release of free retinol (filled circles) and retinol nanoparticles (filled squares) from cream formulation in pH 7.4. About 40 mg of the cream was placed in the vertical diffusion cell dialysis membrane (MWCO 8000-10000 Da) was used for the release study and the receptor medium consisted on pH 7.4 buffer. Samples were collected from the receptor medium and analyzed by radiochemical method using $^3$H retinol. Each data point represents mean±SD (n=3). The nanoparticles were prepared using the method described in FIG. 19.
Figure 45:
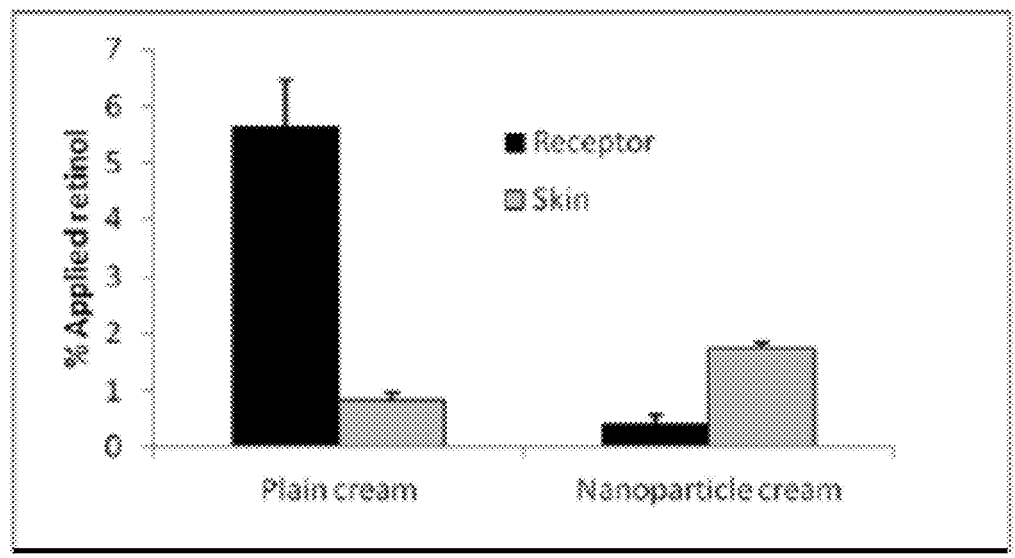
FIG. 45 illustrates the in vitro skin penetration of retinol cream formulations in human skin. Excised human skin was sandwiched between the two compartments of a vertical diffusion cell. The receptor medium consisted of phosphate buffer (pH 7.4) maintained at 37° C. and stirred using a magnetic bead. Free or encapsulated retinol in nanoparticle cream formulations were loaded in the donor chamber. The formulation was applied for 6 hours and then the formulation was removed and the penetration study was continued for 48 hours. At the end of the study, the retinol concentration in the skin and receptor compartment was measured by radiochemical method using $^3$H labeled retinol. The skin was digested using 0.1M sodium hydroxide to determine the retinol concentration. (Mean±SD; n=3). The nanoparticles were prepared using the method described in FIG. 19.

As can be seen in FIG. 43, the encapsulated formulation remained stable and did not show any degradation at room temperature. Further, as can be seen in FIG. 44 the release of retinol from nanoparticles was sustained. As is supported by the data in FIG. 45, much more retinol is retained in the skin with the encapsulated retinol compared to free retinol.

The skin irritation of standard vs. encapsulated formulations was tested in vivo in SKH-1 hairless mice using treatments groups as listed in Table 11-2.

TABLE 11-2

Treatment groups for a skin irritation study.

| Groups | Treatment |
| --- | --- |
| Group 1 | Control (no treatment) |
| Group 2 | Retinol cream |
| Group 3 | Blank zein nanoparticles cream |
| Group 4 | Retinol nanoparticles cream |
| Group 5 | Sodium lauryl sulfate (SLS) cream |

The retinol formulations (0.5 g of 0.1% w/v retinol equivalent) were applied to the backs of SHK-1 hairless mice every day for five (5) days. The transepidermal water loss (TEWL) values were measured using an TEWA meter (Delfin) every day before applying the formulation.

Figure 46:
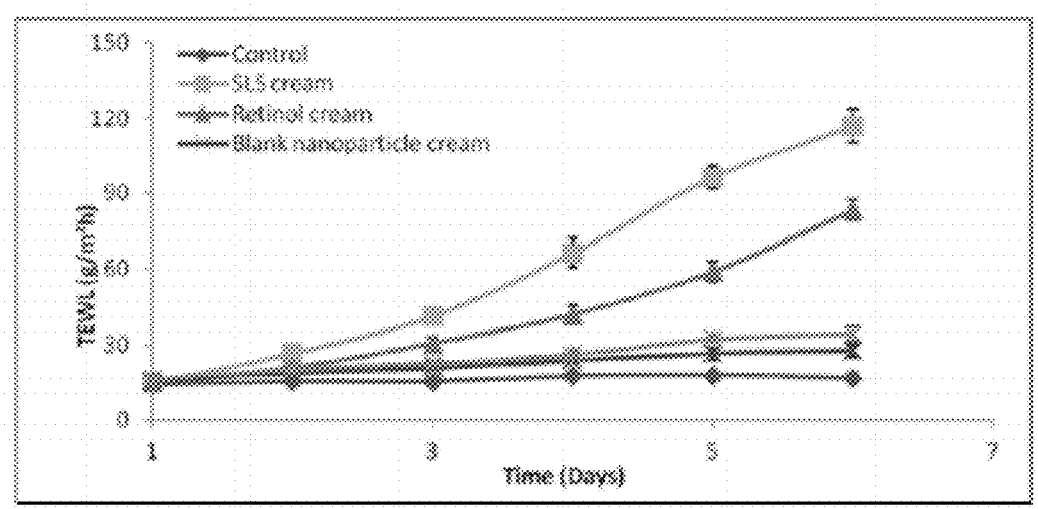
FIG. 46 illustrates the transepidermal water loss (TEWL) values in mice after application of free and nanoparticle encapsulated retinol formulations. Formulations were applied on the back of SKH-1 hairless mice everyday for 5 days. TEWL values were measured using an TEWA meter (Delfin) every day before applying the formulation. The increase in TEWL is a measure of skin irritation and as can be seen from the figure, the retinol encapsulated in the nanoparticle showed no skin irritation and was comparable to negative control (no treatment). On the other hand, the free retinol cream showed skin irritation. Sodium lauryl sulfate (SLS), a know skin irritant, was used as the positive control. Values are mean±SD (n=3). The nanoparticles were prepared using the method described in FIG. 19.

FIG. 46 demonstrates the transepidermal water loss (TEWL) data between the cream containing encapsulated retinol versus free retinol. The increase in TEWL is a measure of skin irritation and as can be seen in the Figure, the retinol encapsulated in nanoparticles showed no skin irritation and was comparable to negative control (no treatment). On the other hand, the free retinol cream showed skin irritation. Sodium lauryl sulfate (SLS), a known skin irritant, was used as the positive control.

Figure 47:
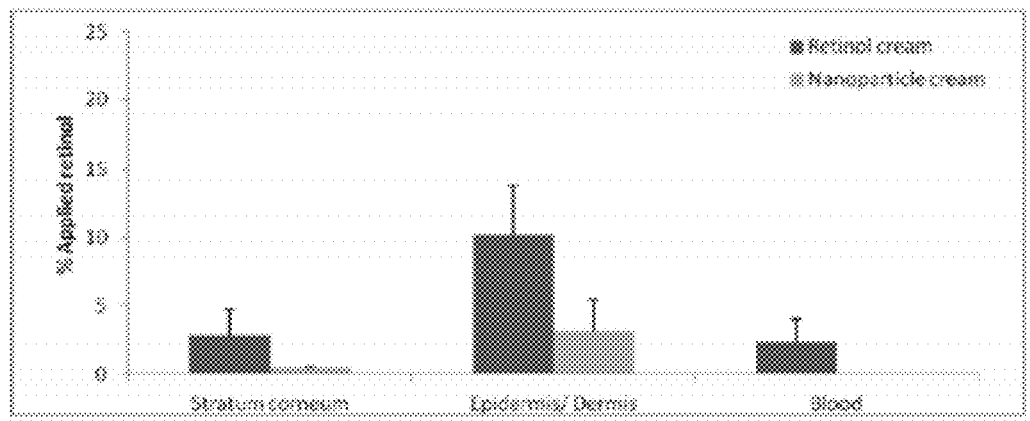
FIG. 47 illustrates the in vivo topical bioavailability of free and nanoparticle encapsulated retinol after treatment for 6 hours in SKH-1 hairless mice. The cream formulations were applied on the back of mice under isoflurane anesthesia. After euthanizing the animals, the skin was tape-stripped using SCOTCH TAPE to remove the stratum corneum (SC). The amount of retinol in the skin (SC and epidermis/dermis) and blood were determined using $^3$H retinol by radiochemical method of analysis. As can be seen, the nanoparticle encapsulated retinol was retained in the skin with no systemic absorption into blood. Values are mean±SD (n=3). The nanoparticles were prepared using the method described in FIG. 19.

In order to obtain bioavailability data for the cream formulations, in vivo topical bioavailability of free and nanoparticle encapsulated retinol was measured in SKH-1 hairless mice. As can be seen in FIG. 47, the nanoparticle encapsulated retinol was retained in the skin with no systemic absorption into the blood.

Example 13

Follicular Delivery of Zein Nanoparticles

In order to track the skin transport of zein nanoparticles, a fluorescent probe was chemically conjugated to zein. 2 mg of fluoroisothiocynate (FITC), 4 mg of 1-(3-dimethyl aminopropyl)-3-ethylcarbodiimide (EDC), and 2.94 mg of N-hydroxy succinimide was dissolved in 5 ml of 90% ethanol and incubated for 3 hours under stirring. Subsequently, zein (50 mg) was added and incubated for 3 hours. Later it the mixture was dialyzed against water for about 8 to 10 hours. Finally, the dispersion was lyophilized. Conjugation of Zein-FITC was confirmed by NMR spectroscopy. Further, nanoparticles were prepared using the method as illustrated in FIG. 1. Confocal studies of the zein-FITC conjugated nanoparticles were also carried out.

Figure 48:
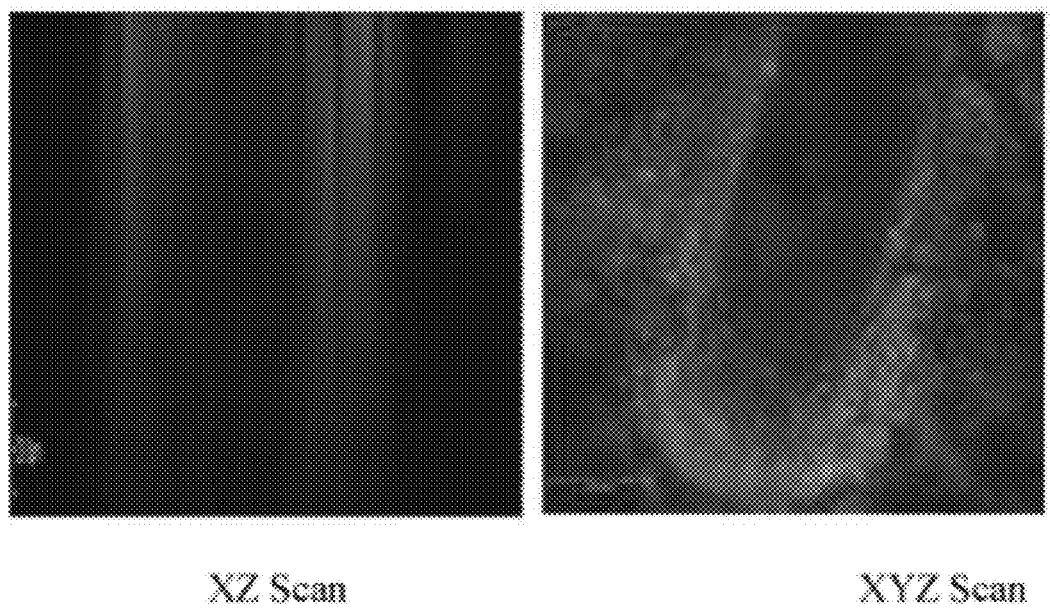
FIG. 48 illustrates the confocal XZ and XYZ images (0-100 μm depth) of porcine skin after 6 hours of treatment with FITC conjugated zein nanoparticles. As can be seen in this figure (right panel), the zein nanoparticles were mainly localized in the hair follicles. This is also evident form the left panel where the fluorescence is observed in streaks from the surface to 100 μm deep inside the skin.

Zein-FITC nanoparticles (equivalent to 5 μg of FITC) dispersed in 100 μl of PBS pH 7.4 were used for skin penetration studies. Excised porcine skin was sandwiched between the two compartments of a vertical diffusion cell. The receptor medium consisted of phosphate buffer (pH 7.4) maintained at 37° C. and stirred using a magnetic bead. FITC labeled nanoparticles was applied on the skin for 6 hours. At the end of the study, the skin was washed and observed under confocal fluorescence microscopy. As shown in FIG. 48, the zein nanoparticles are mainly localized to the hair follicles. Further, there was no autofluorescence from skin at the measured wavelength. This is also evident from the left panel where the fluorescence is observed in streaks from the surface to 100 μm deep inside the skin. The results in addition to demonstrating the skin transport pathway for zein nanoparticles also shows that it can be used to target the hair follicle to treat various follicular diseases. These include acne, hair loss, seborrhetic eczema, folliculitis and certain skin cancers. Given the use of retinol for treatment of acne, retinol encapsulated in zein nanoparticles can be targeted to the hair follicles for effective treatment of acne.

Figure 28:
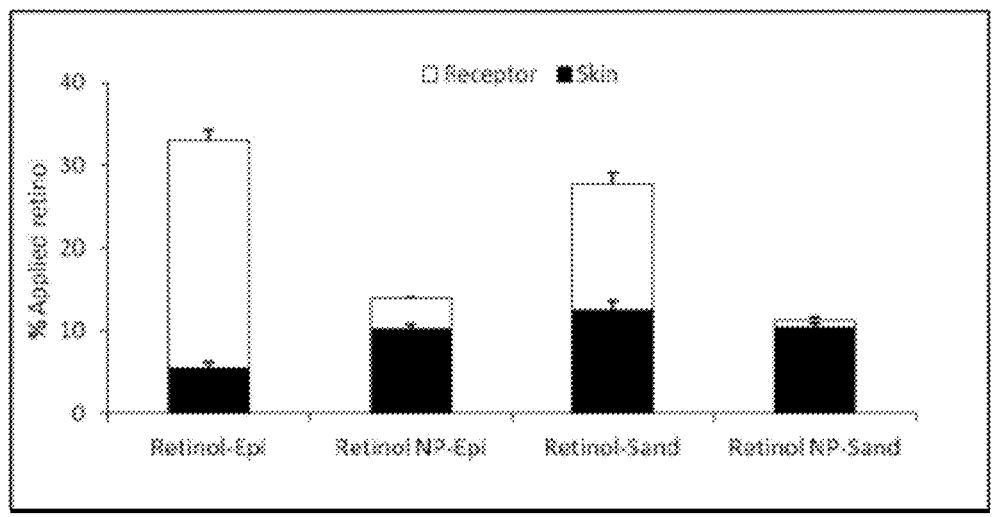
FIG. 28 illustrates the percentage of applied retinol at the end of 48 hours in porcine skin and in receptor medium after treatment with free retinol and retinol encapsulated in nanoparticles. Excised porcine epidermis (Epi) was placed between the two compartments of a vertical diffusion cell. In the second set of experiments, the stratum corneum (SC) was removed from the porcine epidermis and then was physically placed (sandwiched) over the porcine epidermis (Sand) and was used in the study. Free retinol or retinol nanoparticles were applied over the skin and the study was carried out for 48 hours. The receptor medium consisted of phosphate buffer (pH 7.4) maintained at 37° C. and stirred using a magnetic bead. Free or encapsulated retinol dispersion in phosphate buffer (pH 7.4) was loaded in the door chamber. At the end of the study, the retinol concentration in the skin and receptor compartment was measured by radiochemical method using $^3$H labeled retinol.

To demonstrate the follicular targeting of retinol, a skin sandwich model was used. In the sandwich skin (see FIG. 28), the follicular pathways are blocked by the SC sandwiched over the epidermis. In the sandwich skin model the amount of retinol transported into the receptor compartment was reduced both for free and nanoparticle encapsulated retinol compared to conventional skin epidermis penetration studies. However, there was significant reduction in the transport of retinol from the nanoparticles indicating that a significant fraction of retinol micelles is transported through hair follicles. Follicular targeting is an added advantage of nanoparticles to target retinol to the disease site in the hair follicles.

Example 14

Interaction of Zein Nanoparticles with Skin Lipids

To understand the interaction of zein nanoparticles with skin lipids and test whether it can act as skin penetration enhancer, infra-red spectroscopy studies were carried out. Porcine epidermis was mounted in a vertical diffusion cell and treated with zein nanoparticles for 24 hours at 37° C. The epidermis was blotted dry with WHATMAN filter paper before recording the spectrum. The spectrum was recorded before and after treatment. The spectrum was recorded on ZnSe at 2 cm$^{-1}$ resolution in NICOLET 380 ATR-FITR spectrophotometer (THERMO ELECTRON Corporation, Madison, Wis.). Each spectrum was an average of 100 scans. The peak position of the skin lipids were analyzed using OMNIC software.

TABLE 14-1

Shift in skin lipids after treatment with zein nanoparticles.

| Treatment | Wave number 2920 cm$^{-1}$ | | | Wave number 2850 cm$^{-1}$ | | |
|---|---|---|---|---|---|---|
| | Pre-treatment | Post-treatment | Shift | Pre-treatment | Post-treatment | Shift |
| Buffer solution | 2920 ± 0.02 | 2920.8 ± 0.15 | 0.46 | 2850.4 ± 0.15 | 2850 ± 0.96 | 0.50 |
| Zein nanoparticles | 2919.7 ± 0.37 | 2921.4 ± 0.35 | 1.66 | 2850.2 ± 0.25 | 2851.5 ± 0.26 | 1.26 |

Zein nanoparticles were prepared as described in FIG. 1.

As can be seen in Table 14-1, the lipid symmetric (2850 cm$^{-1}$) and asymmetric (2920 cm$^{-1}$) peaks were shifted to higher wave numbers. A shift in the lipid stretching peaks indicates the interaction with skin lipids. The shift was significant compared to the shift observed with buffer treatment. These results indicate that zein nanoparticles can act as penetration enhancers to increase skin penetration. Without being bound by theory, the penetration enhancement may be attributable to the lecithin and PLURONIC surfactants in the formulation.

Example 15

Encapsulation/Adsorption of Protein Drugs

Figure 49:
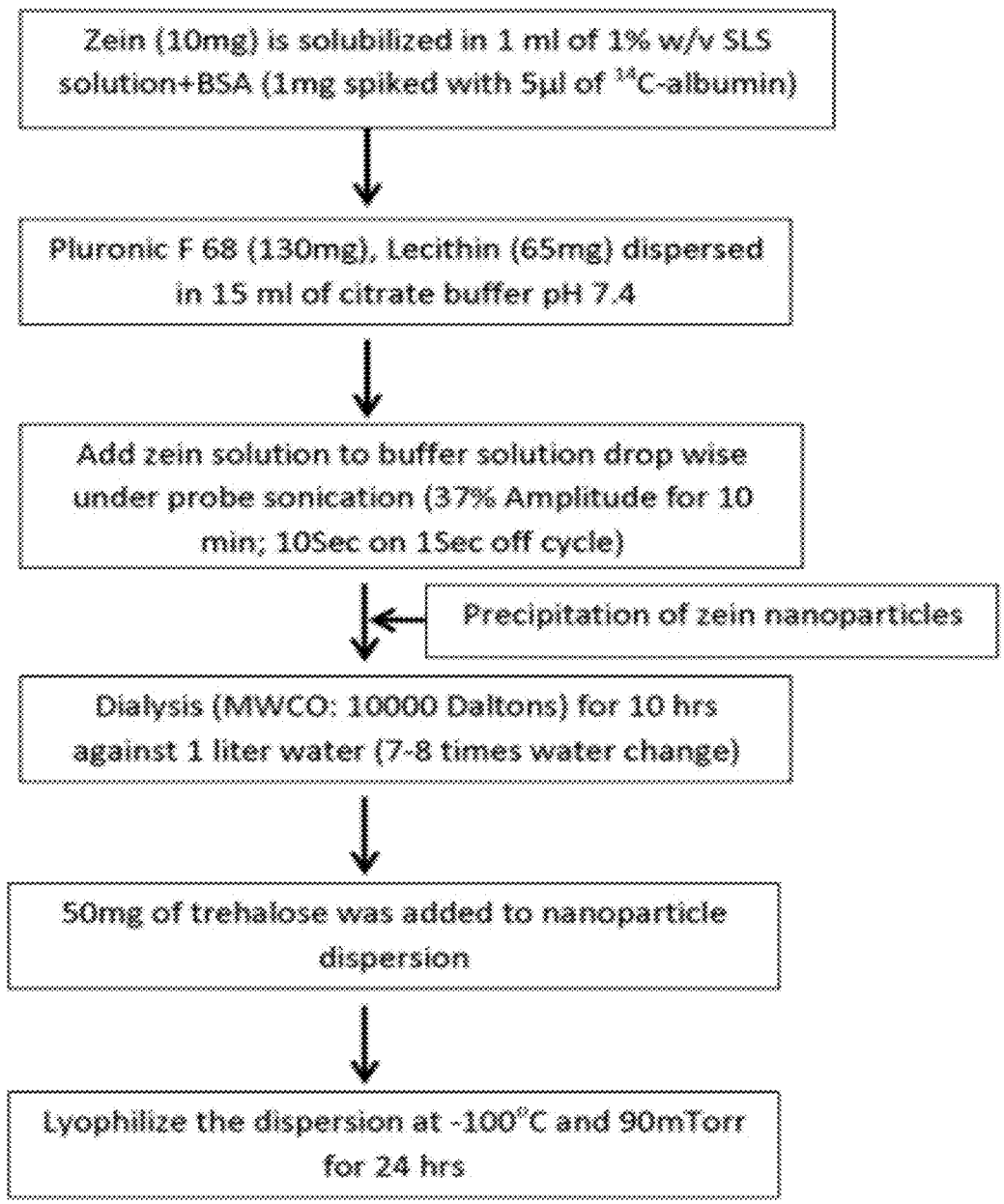
FIG. 49 illustrates by means of a flow chart the general steps for encapsulation of bovine serum albumin (BSA), according to one embodiment.
Figure 50:
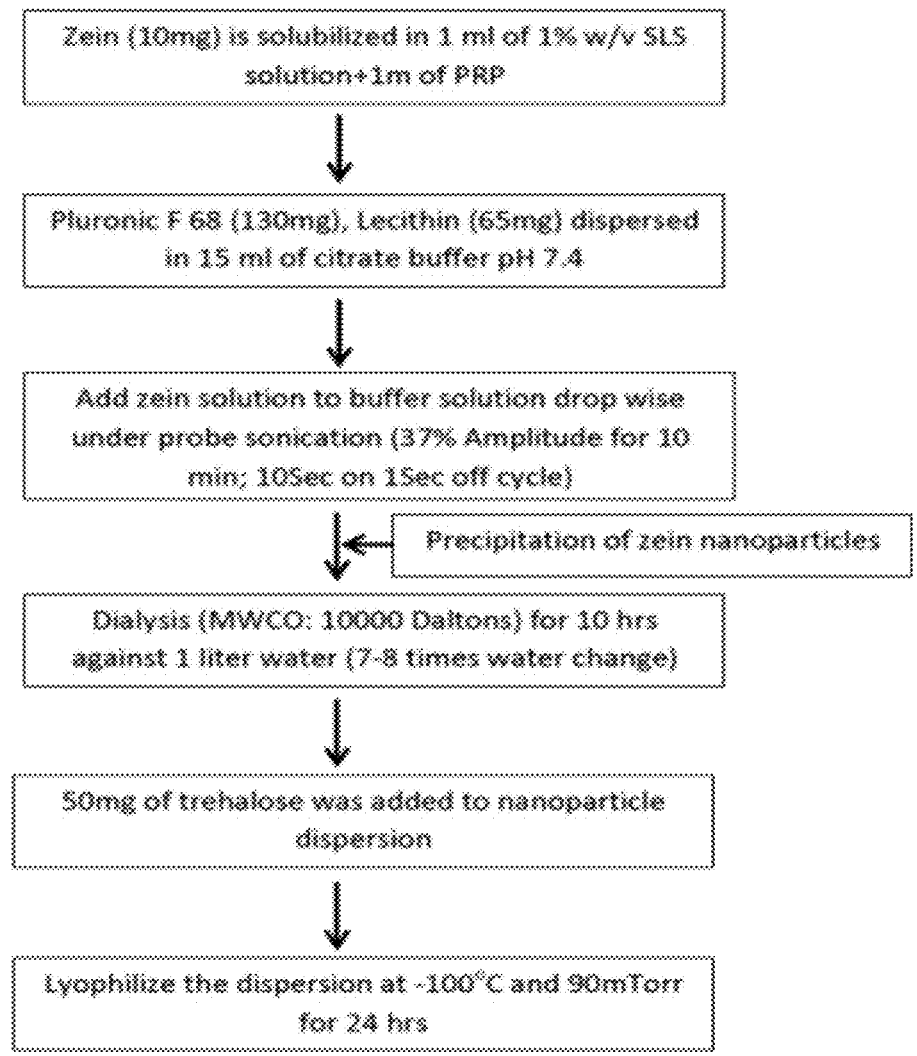
FIG. 50 illustrates by means of a flow chart the general steps for adsorption platelet rich plasma (PRP), according to one embodiment.

For encapsulation of protein drugs, the method of FIG. 1 was modified (see FIG. 49). Since ethanol in the first phase can precipitate the water soluble protein drugs, ethanol was replaced with sodium lauryl sulfate to solubilize zein. The method as shown in FIGS. 49 and 50 was used for encapsulation of model protein bovine serum albumin (BSA, 66 kDa) and platelet rich plasma (PRP).

Example 16

Preparation of Platelet Rich Plasma (PRP)

Fresh porcine/sheep blood was used to separate PRP. Blood was collected by adding EDTA as an anti-coagulant. Around 10 ml of blood was centrifuged at 2400 rpm for 10 min. at 20° C. Later, the supernatant (PRP and platelet poor plasma) was collected into another tube and centrifuged at 3600 rpm for 15 min. at 20° C. Platelet poor plasma was removed and the 1 ml plasma at the bottom of the tube was collected as PRP. Platelet count was carried out by diluting the plasma 100 times using water with an automatic cell counter.

Sheep blood PRP count: $2.4 \times 10^8$ platelets/ml

Porcine blood PRP count: $2.34 \times 10^8$ platelets/ml

TABLE 16-1

Characteristics of protein encapsulated zein particles.

| Sample | Particle size with PDI Before lyophilization | Particle size with PDI After lyophilization | % EE |
|---|---|---|---|
| Blank nanoparticles | 106.9 (0.157) | 196.6 (0.228) | — |
| PRP nanoparticles | 176.8 (0.266) | 198.3 (0.345) | 49 ± 3.5 |
| BSA nanoparticles | 113.9 (0.188) | 222.3 (0.283) | 70.5 ± 3.5 |

PDI—polydispersity index 1 mg of nanoparticles was dispersed in 1 ml of water using a bath sonicator for 1 minute. Samples were diluted 100 times with water and the particle size was measured using a NICOMP particle size analyzer.

Example 17

Adsorption of PRP onto Zein Nanoparticles

Zein nanoparticles were prepared using the same procedure as described in FIG. 1, with the exception that different stabilizers were used in the 2$^{nd}$ aqueous phase: 0.1% TWEEN 80 or PLURONIC F68 or casein was used alone. Particle sizes of the nanoparticles were measured using a NICOMP particle size analyzer.

TABLE 17-1

Particle size of zein nanoparticles prepared using different surfactants.

| Method of preparation | Size (nm) | PDI |
|---|---|---|
| Nanoparticles (TWEEN 80) | 715.6 | 0.654 |
| Nanoparticles (PLURONIC F68 + Lecithin) | 289.4 | 0.312 |
| Nanoparticles (PLURONIC F68) | 389.4 | 0.354 |
| Nanoparticles (Casein) | 153.4 | 0.239 |

The surfactants given in the parentheses were used in the second aqueous phase

Accurately weighed amounts of the zein nanoparticles (200 mg) were taken in the vials and added with 0.6 ml of PRP solution and 4.4 ml of citrate buffer (pH 7.4). Later the vials were incubated for 2 and 6 hours at 37° C. under 200 rpm. At the end of the study, the dispersion was centrifuged at 15,000 rpm for 10 min. and the adsorbed PRP from the pellet was assayed using an ELISA kit specific for platelet derived growth factor (PDGF).

TABLE 17-2

Percent PRP adsorbed onto zein nanoparticles as a function of incubation time.

| Method of preparation | % Adsorbed | |
|---|---|---|
| | 2 hrs | 6 hrs |
| Nanoparticles (TWEEN 80) | 8.7 ± 1.5 | 11.2 ± 1.3 |
| Nanoparticles (PLURONIC F68 + lecithin) | 10.3 ± 1.3 | 12.8 ± 0.9 |
| Nanoparticles (PLURONIC) | 10.7 ± 1.9 | 12 ± 1.3 |
| Nanoparticles (Casein) | 12.8 ± 1.6 | 14.1 ± 0.9 |

Although there was no significant difference in the adsorption capacity between the different zein nanoparticles, where zein-casein nanoparticles showed the highest adsorption. Similarly, the adsorption increased with incubation time but was not significant, thus 2 hours should be sufficient for PRP adsorption.

Example 18

PSA Cross-Linked ZC Nanoparticles

The objective of this work is to provide shell cross-linked nanoparticles based on a hydrophobic core zein and a hydrophilic shell casein. Polysialic acid (PSA) is a homopolymer negatively charged polysaccharide consisting of α-2,8-linked sialic acid units with M. wt of 11 kDa. Polysialic acid can be used to cross-linked the shell because of its biocompatibility compared to other cross-linking agents.

EDC and NHS is added to PSA and dissolved in 10 ml of deionized water. After stirring at room temperature for 3 min., zein-casein nanoparticles (prepared using the method as disclosed in FIG. 39) were added, and the reaction is allowed to proceed overnight. EDC is added to convert carboxyl groups on PSA to amine-reactive NHS esters which can then interact with primary amines of the protein. The solution is centrifuged and lyophilized to yield the desired cross-linked nanoparticles (zein-casein nanoparticles).

Example 19

PSA-Zein Nanocarriers

The objective in this study is to form core-shell nanocarriers using zein as the core and hydrophilic PSA as the shell. In this case, the PSA is chemically conjugated to zein. PSA is oxidized with sodium metaperiodate ($NaIO_4$). PSA and zein mixture was kept for 15 min. in the dark. The oxidized PSA is precipitated with alcohol followed by centrifugation and lyophilized for further use. The coupling reaction on aldehydic PSA with zein is carried out in a DMSO/water mixture in the presence of 2-picoline-borane as a reducing catalyst. To allow the conjugation reaction, the mixture is kept under a magnetic stirrer for 48 hours. The core-shell nanocarrier was dialyzed against water and lyophilized.

Example 20

Pharmaceutical Dosage Forms

The following formulations illustrate representative pharmaceutical dosage forms that may be used for the therapeutic or cosmetic administration of a nanoparticle formulation described herein, which can be an aqueous dispersion or a lyophilized powder (hereinafter referred to as 'Composition X'):

| (i) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (ii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (iii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (iv) Topical Ointment | wt. % |
|---|---|
| 'Composition X' | 5% |
| Propylene glycol | 1% |
| Anhydrous ointment base | 40% |
| Polysorbate 80 | 0.2% |
| Methyl paraben | 0.2% |
| Purified water | q.s. to 100 g |

| (v) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (vi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraban | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A nanoparticle comprising a prolamine protein, cargo or cargo molecule, an anionic surfactant, a non-ionic surfactant, and optionally a phospholipid, at least one protein polymer, at least one polysaccharide, or at least one synthetic polymer, wherein the nanoparticle is biodegradable, biocompatible, and non-immunogenic, and wherein the diameter of the nanoparticle is less than about 400 nm.

2. The nanoparticle of claim 1, wherein the prolamine protein comprises white zein, yellow zein, gliadin, hordein, or kafirin.

3. The nanoparticle of claim 2, wherein the cargo or cargo molecule is selected from the group consisting of a pharmaceutical material, a therapeutic material, a cosmetic material a diagnostic agent, agricultural material, an immuno-potentiating agent, a bioactive agent, and combinations thereof.

4. The nanoparticle of claim 1, wherein the cargo molecule is a retinoid selected from the group consisting of retinol, 13-trans-retinoic acid (tretinoin), 13-cis-retinoic acid (isotretinoin), 9-cis-retinoic acid (alitretinoin), retinaldehyde, etretnate, acitretin, $\alpha$-carotene, $\beta$-carotene, $\gamma$-carotene, $\beta$-cryptozanthin, lutein, zeaxanthin, and combinations thereof, and wherein the nanoparticle further comprises a phospholipid and a poloxamer nonionic surfactant.

5. The nanoparticle of claim 4, wherein the retinoid is retinyl acetate or retinyl palmitate.

6. The nanoparticle of claim 4, wherein the retinoid in the nanoparticle is about 0.01 wt. % to about 0.3 wt. % of the prolamine of the nanoparticle.

7. The nanoparticle of claim 1, wherein the cargo molecule is 5-fluorouracil.

8. The nanoparticle of claim 1, wherein the cargo is a cell, protein, nucleic acid, antibody, growth factor, or a combination thereof.

9. The nanoparticle of claim 8, wherein the cargo is platelet rich plasma (PRP), and wherein the cargo is adsorbed to the surface of the nanoparticle.

10. The nanoparticle of claim 1, wherein the nanoparticle is cross-linked.

11. The nanoparticle of claim 1, wherein the prolamine protein of the nanoparticle is PEGylated.

12. The nanoparticle of claim 1, wherein the nanoparticle is in the form of a dry free flowing, colorless or white, non-hygroscopic powder.

13. The nanoparticle of claim 1, further comprising a retinoid and a diluent, an excipient, or carrier to form a pharmaceutically or cosmetically acceptable composition.

14. The nanoparticle of claim 13, wherein the composition is topical and is in the form of a dispersion, an aerosol formulation, a gel, an ointment, a cream, a lotion, or a shampoo.

15. A kit comprising: a) a lyophilized powder or dispersion containing the nanoparticles of claim 1; b) one or more buffers; c) one or more labels; d) one or more containers; and e) an instruction manual, wherein the instruction manual discloses how to use the lyophilized powder or dispersion of said cargo loaded nanoparticles.

16. A method of preparing a nanoparticle comprising: dissolving a prolamine protein in a hydroalcoholic solvent and a buffer, an organic solvent, or an anionic surfactant and a buffer, wherein the buffer comprises a citrate anion and at least at one nonionic surfactant, at least one phospholipid, a phosphoprotein, at least one polysaccharide, a phosphoprotein-polysaccharide conjugate, at least one synthetic polymer, or a combination thereof, to form a precipitate; sonicating the precipitate; centrifuging the remaining aqueous phase to form a pellet; forming an aqueous dispersion from the pellet, and optionally adding a cryoprotectant; and lyophilizing the dispersion, wherein the resulting nanoparticle has a particle size of between less than about 100 nm to about 225 nm.

17. A method of preparing a nanoparticle comprising: dissolving a prolamine protein in a hydroalcoholic solvent and a buffer, an organic solvent, or an anionic surfactant and a buffer, wherein the buffer comprises a citrate anion and at least at one nonionic surfactant, at least one phospholipid, a phosphoprotein, at least one polysaccharide, a phosphoprotein-polysaccharide conjugate, at least one synthetic polymer, or a combination thereof, to form a precipitate; sonicating the precipitate; centrifuging the remaining aqueous phase to form a pellet; forming an aqueous dispersion from the pellet, and optionally adding a cryoprotectant; and lyophilizing the dispersion, wherein the resulting nanoparticle has a particle size of between less than about 100 nm to about 225 nm, and wherein the dissolving step comprises dissolving the prolamine protein in a hydroalcoholic solvent and a citrate anion containing buffer, and wherein the phosphoprotein is $\beta$-casein and the polysaccharide is dextran or gum *Arabica*.

18. The method of claim 17, wherein the dissolving step comprises dissolving the prolamine protein in a hydroalcoholic solvent and a citrate anion containing buffer, and wherein the phosphoprotein-polysaccharide conjugate is $\beta$-casein conjugated to dextran.

19. The method of claim 16, wherein the dissolving step comprises dissolving the prolamine protein in an anionic surfactant and a citrate anion containing buffer, wherein the anionic surfactant is selected from the group consisting of sodium dioctyl sulfosuccinate, sodium lauryl sulfate, benzalkonium chloride, cetyl trimethyl ammonium bromide, N-dodecyl trimethyl ammonium bromide, polyvinyl alcohol, polyvinyl pyrrolidone, and combinations thereof, and wherein the buffer comprises a nonionic surfactant and a phospholipid, wherein the nonionic surfactant is selected from the group consisting of poloxamers, polyoxyethylene alkyl ethers, sorbitan esters, polyoxyethylene sorbitan fatty acid esters, and combinations thereof, and the phospholipid is selected from the group consisting of egg lecithin, soy lecithin, phosphatidyl choline, phosphatidyl ethanolamine, and combinations thereof.

20. A method of treating a skin disorder comprising administering the nanoparticle of claim 1 to a subject in need thereof, wherein the skin disorder is selected from the group consisting of acne, hair loss, seborrhetic eczema, folliculitis, and cutaneous malignancies.

\* \* \* \* \*